US009505830B2

(12) United States Patent
Ordas et al.

(10) Patent No.: US 9,505,830 B2
(45) Date of Patent: Nov. 29, 2016

(54) RECOMBINANT ANTIBODIES TO THE VASCULAR ENDOTHELIAL GROWTH FACTOR (VEGF) WHICH ARE OBTAINED BY MEANS OF MUTAGENESIS OF VARIABLE REGIONS

(75) Inventors: Humberto Lamdan Ordas, Artemisa (CU); Jorge Victor Gavilondo Cowley, La Habana (CU); Marta Ayala Avila, La Habana (CU); Yasmiana Muñoz Pozo, La Habana (CU); Amaury Pupo Meriño, La Habana (CU); Gertrudis Rojas Dorantes, La Habana (CU); Lincidio Perez Sanchez, La Habana (CU)

(73) Assignees: Centro de Ingenieria Genetica y Biotecnologia, Havana (CU); Biorec S.A., Montevideo (UY)

( * ) Notice: Subject to any disclaimer, the term of this patent is extended or adjusted under 35 U.S.C. 154(b) by 231 days.

(21) Appl. No.: 13/976,060

(22) PCT Filed: Dec. 26, 2011

(86) PCT No.: PCT/CU2011/000009
§ 371 (c)(1),
(2), (4) Date: Oct. 1, 2013

(87) PCT Pub. No.: WO2012/089176
PCT Pub. Date: Jul. 5, 2012

(65) Prior Publication Data
US 2014/0086829 A1    Mar. 27, 2014

(30) Foreign Application Priority Data
Dec. 28, 2010   (CU) .................................. 2010-0264

(51) Int. Cl.
C07K 16/22    (2006.01)
A61K 39/395   (2006.01)
A61K 51/10    (2006.01)
A61K 39/00    (2006.01)

(52) U.S. Cl.
CPC ........... *C07K 16/22* (2013.01); *A61K 51/1021* (2013.01); *A61K 2039/505* (2013.01); *C07K 2317/21* (2013.01); *C07K 2317/55* (2013.01); *C07K 2317/565* (2013.01); *C07K 2317/622* (2013.01); *C07K 2317/64* (2013.01); *C07K 2317/73* (2013.01); *C07K 2317/76* (2013.01); *C07K 2317/92* (2013.01)

(58) Field of Classification Search
CPC .............. C07K 16/22; C07K 2317/21; C07K 2317/55; C07K 2317/56; C07K 2317/565; C07K 2317/73; C07K 2317/76; C07K 2317/92; C07K 2317/64; C07K 2317/622; C07K 2317/52; C07K 2319/00; C07K 2316/52; A61K 51/1021; A61K 2039/505
See application file for complete search history.

(56) References Cited

U.S. PATENT DOCUMENTS 5,730,977 A    3/1998   Ooka et al.

FOREIGN PATENT DOCUMENTS

EP    2093236       8/2009
WO    2008052489    5/2008

OTHER PUBLICATIONS

Rudikoff et al., Proc. Natl. Acad. Sci. USA, 79(6): 1979-1983, Mar. 1982.*
Winkler et al., J Immunology 165: 4505-4514, 2000.*
Casset et al., Biochemical and Biophysical Research Communications 307: 198-205, 2003.*
Vajdos et al., Journal of Molecular Biology 320: 415-428, 2002.*
Wu et al., Journal of Molecular Biology 294: 151-162, 1999.*
Stancovski et al., PNAS, 88: 8691-8695, 1991.*
Golay et al., Archives of Biochemistry and Biophysics 526: 146-153, 2012.*
Hay et al., Nature Biotechnology 32(1): 40-51, Jan. 2014.*
Dawood et al., Cancer 118: 2780-2786, 2012.*
Yu et al., Investigative Ophthalmology & Visual Science 49(2): 522-527, Feb. 2008.*
Muller et al., VEGF and the Fab fragment of a humanized neutralizing antibody: crystal structure of the complex at 2.4 A resolution and mutational analysis of the interface, Research ARticle, 6:1153-1167 (1998).
Asano et al., An anti-human VEGF monoclonal antibody, MV833, that exhibits potent anti-tumor activity in vivo, Hybridoma, vol. 17, No. 2 (1998).
Rojas et al., Efficient construction of a highly useful phage-displayed human antibody repertoire, Biochemical and Biophysical Research Communications, 336 (2005) pp. 1207-1213.
Brekken et al., VEGF-VEGF receptor complexes as markers of tumor vascular endothelium, Journal of Controlled Release, vol. 74, pp. 173-181 (2001).

(Continued)

*Primary Examiner* — Phuong Huynh
(74) *Attorney, Agent, or Firm* — Hoffmann & Baron, LLP

(57) ABSTRACT

The present invention reveals human recombinant antibodies that recognize the human Vascular Endothelium Growth Factor A (VEGF-A), block its interaction with the VEGFR2 receptor, and interfere with its proliferative effect in vitro and pro-angiogenic effect in vivo. The antibodies identify an epitope on human VEGF-A different from any other previously reported, and were obtained by combining one immunoglobulin light chain variable region with other three heavy chain ones. The antibodies were obtained by human immunoglobulin variable region mutagenesis, and can be employed for the immunotherapy of pathological entities associated with an increase in vasculature, such as age-related macular degeneration, cancer, and others.

17 Claims, 6 Drawing Sheets

(56) References Cited

OTHER PUBLICATIONS

Brekken et al., Selective inhibition of vascular endothelial growth factor (VEGF) receptor 2 (KDR/Flk-1) activity by a monoclonal anti-VEGF antibody blocks tumor growth in mice, Cancer Research, vol. 60, pp. 5117-5124 (2000).
Carmeliet et al., Angiogenesis in cancer and other diseases, Nature, vol. 407 (2000).
Ferrara et al., The biology of VEGF and its receptors, Nature Medicine, vol. 9, No. 6 (2003).
Fuh et al., Structure-Function studies of two synthetic anti-vascular endothelial growth factor fabs and comparison with the Avastin TM Fab, The Journal of Biological Chemistry, vol. 281, No. 10, pp. 6625-6631 (2006).
Morera et al., Biologically active vascular endothelial growth factor as a bacterial recombinant glutathione S-transferase fusion protein, Biotechnol. Appl. Biochem. vol. 44, pp. 45-53 (2006).
Morera et al., Anti-tumoral effect of active immunotherapy in C57BL/6 mice using a recombinant human VEGF protein as antigen and three chemically unrelated adjuvants, Angiogenesis, vol. 11 pp. 381-393 (2008).
Muller et al., Vascular endothelial growth factor: Crystal structure and functional mapping of the kinase domain receptor binding site, PNAS, vol. 94, pp. 7192-7197 (1997).
Balint et al., Antibody engineering by parsimonious mutagenesis, Gene, vol. 137, pp. 109-118 (1993).
Schlaeppi et al., Characterization of a new potent, in vivo neutralizing monoclonal antibody to human vascular endothelial growth factor, J Cancer Res. Clin. Oncol. vol. 125, pp. 336-342 (1999).
Vitaliti et al., Inhibition of tumor angiogenesis by a single-chain antibody directed against vascular endothelial growth factor, Cancer Research, vol. 60, pp. 4311-4314 (2000).
Lamdan et al., Isolation of a novel neutralizing antibody fragment against human vascular endothelial growth factor from a phage-displayed human antibody repertoire using an eptiope disturbing strategy, Journal of Biotechnology, vol. 151, pp. 166-174 (2011).
Allison et al., Avastin's commercial march suffers setback, Nature Biotechnology, vol. 28, No. 9 pp. 879-880 (2010).
Bottomley et al., Placenta growth factor (PlGF) induces vascular endothelial growth factor (VEGF) secretion from mononuclear cells and is co-expressed with VEGF in synovial fluid, Clin. Exp. Immunol., vol. 119, pp. 182-188 (2000).
Celletti et al., Vascular endothelial growth factor enhances atherosclerotic plaque progression, Nature Medicine, vol. 7, No. 4 pp. 425-429 (2001).
Detmar et al., Overexpression of vascular permeability factor/vascular endothelial growth factor and its receptors in psoriasis, J. Exp. Med., vol. 180, pp. 1141-1146 (1994).
Ferrara et al., Pituitary follicular cells secrete a novel heparin-binding growth factor specific for vascular endothelial cells, Biochemical and Biophysical Research Communications, vol. 161, No. 2, pp. 851-858 (1989).
Ferrara et al., Bevacizumab (Avastin), a humanized anti-VEGF monoclonal antibody for cancer therapy, Biochemical and Biophysical Research Communications, vol. 333, pp. 328-335 (2005).
Gaudreault et al., Preclinical pharmacokinetics of ranibizumab (rhuFabV2) after a single intravitreal administration, Investigative Opthalmology & Visual Science, vol. 46, No. 2 (2005).
Jayson et al., Molecular imaging and biological evaluation of HuMV833 anti-VEGF antibody: Implications for trial design of antiangiogenic antibodies, Journal of the National Cancer Institute, vol. 94, No. 19, pp. 1484-1493 (2002).
Grunstein et al., Tumor-derived expression of vascular endothelial growth factor is a critical factor in tumor expansion and vascular function, Cancer Research, vol. 59, pp. 1592-1598 (1999).
Grunstein et al., Isoforms of vascular endothelial growth factor act in a coordinate fashion to recruit and expand tumor vasculature, Mol. Cell. Biuol., vol. 20, pp. 7282-7291 (2000).
Hoshino et al., Expression of vascular endothelial growth factor, basic fibroblast growth factor, and angiogeninimmunoreactivity in asthmatic airways and its relationship to angiogenesis, J. Allergy Clin. Immunol., vol. 107, pp. 295-301 (2001).
Joukov et al., A novel vascular endothelial growth factor, VEGF-C, is a ligand for the Flt4 (VEGFR-3) and KDR (VEGFR-2) receptor tyrosine kinases, EMBO Journal, vol. 15, No. 2, pp. 290-298 (1996).
Kaipainen et al., The related FLT4, FLT1, and KDR receptor tyrosine kinases show distinct expression patterns in human fetal endothelial cells, J. Exp. Med., vol. 178, pp. 2077-2088 (1993).
Kanazawa et al., VEGF, basic-FGF, and TGF-B in Chrohn's disease and ulcerative colitis: A novel mechanism of chronic intestinal inflammation, The American Journal of Gastroenterology, vol. 96, No. 3, (2001).
Kaner et al., Lung overexpression of the vascular endothelial growth factor gene induces pulmonary edema, Am. J. Respir. Cell. Mol. Biol., vol. 22, pp. 657-664 (2000).
Kim et al., The vascular endothelial growth factor proteins: Identification of biologically relevant regions by neutralizing monoclonal antibodies, Growth Factors, vol. 7, pp. 53-64 (1992).
Leung et al., Vascular endothelial growth factor is a secreted angiogenic migoten, Science, vol. 246, pp. 1306-1309 (1989).
Marks et al., By-passing immunization human antibodies from V-gene libraries displayed on phage, J. Mol. Biol., vol. 222, pp. 581-597 (1991).
J. McLaren, Vascular endothelial growth factor and endometriotic angiogenesis, Human Reproduction Update, vol. 6, No. 1, pp. 45-55 (2000).
Murata et al., The relation between expression of vascular endothelial growth factor and breakdown of the blood-retinal barrier in diabetic rat retinas, Laboratory Investigation, vol. 74, No. 4, pp. 819-825 (1996).
Nagura et al., Expression of vascular endothelial growth factor (VEGF) and VEGF receptor-1 (Flt-1) in graves disease possibly correlated with increased vascular density, Hum. Pathol., vol. 32, pp. 10-17 (2001).
Neufeld et al., Similarities and differences between the vascular endothelial growth factor (VEGF) splice variants, Cancer and Metastasis Reviews, vol. 15, pp. 153-158 (1996).
Ogawa et al., A novel type of vascular endothelial growth factor, VEGF-E (NZ-7 VEGF), preferentially utilizes KDR/Flk-1 receptor and carries a potent mitotic activity without heparin-binding domain, vol. 273, pp. 31273-31282 (1998).
Olofsson et al., Vascular endothelial growth factor B, a novel growth factor for endothelial cells, Proc. Natl. Acad. Sci. USA, vol. 93, pp. 2576-2581 (1996).
Pufe et al., Splice variants VEGF121 and VEGF165 of the angiogenic peptide vascular endothelial cell growth factor are expressed in the synovial tissue of patients with rheumatoid arthritis, The Journal of Rheumatology, vol. 28, pp. 1482-1485 (2001).
James D. Reynolds, The management of retinopathy of prematurity, Paediatr Drugs, vol. 3, pp. 263-272 (2001).
Masabumi Shibuya, Role of VEGF-FLT receptor system in normal and tumor angiogenesis, Advances in Cancer Research, vol. 67, pp. 281-316 (1995).
Thickett et al., Vascular endothelial growth factor may contribute to increased vascular permeability in acute respiratory distress syndrome, Am. J. Respir. Crit. Care Med., vol. 164, pp. 1601-1605 (2001).
Tonello et al., Role of sympathetic activity in controlling the expression of vascular endothelial growth factor in brown fat cells of lean and genetically obese rats, FEBS Letters, vol. 442, pp. 167-172 (1999).
Vasir et al., Gene expression of VEGF and its receptors Flk-1/KDR and Flt-1 in cultured and transplanted rat islets, Transplantation, vol. 71, No. 7, pp. 924-935 (2001).
Wells et al., Levels of vascular endothelial growth factor are elevated in the vitreous of patients with subretinal neovascularisation, Br J Opthalmol, vol. 80, pp. 363-366 (1996).
S. Wizigmann-Voos et al., Pathology, genetics and cell biology of hemangioblastomas, Histol. Histopathol, vol. 11, pp. 1049-1061 (1996).
Yamada et al., Molecular cloning of a novel vascular endothelial growth factor, VEGF-D, Genomics, vol. 42, pp. 483-488 (1997).

* cited by examiner

A

B

A

B

A

B

RECOMBINANT ANTIBODIES TO THE VASCULAR ENDOTHELIAL GROWTH FACTOR (VEGF) WHICH ARE OBTAINED BY MEANS OF MUTAGENESIS OF VARIABLE REGIONS

CLAIM OF PRIORITY

This application is the U.S. National Phase of, and Applicants claim priority from, International Application Number PCT/CU2011/000009 filed Dec. 26, 2011 and Cuban Patent Application No. 2010-0264 filed Dec. 28, 2010, which are incorporated herein by reference.

TECHNICAL FIELD

The present invention is related to the fields of biotechnology and pharmaceutical industry, in particular with the development and application of human recombinant antibodies that specifically recognize the human Vascular Endothelial Growth Factor-A (abbreviated VEGF-A) (Ferrara, N. et al. 2003. Nature Medicine 9: 669-676). The different types of recombinant antibodies contained in this invention were developed combining one same immunoglobulin light chain variable region (VL) with other three heavy chain variable regions (VH), using genetic engineering techniques. The recombinant antibodies recognize in VEGF-A an epitope not previously described, block the interaction of VEGF-A and its VEGFR2 receptor, and in consequence, interfere with the stimulatory and proangiogenic effects of VEGF-A in vitro and in vivo. Because of these properties, the new human recombinant antibodies can be employed for the immunotherapy of pathological entities associated with an increase in vasculature, such as age-related macular degeneration, cancer, rheumatoid arthritis and others.

STATE OF THE ART

The process of formation of new blood vessels from pre-existing ones (angiogenesis) is regulated by the equilibrium of pro and anti-angiogenic factors that act on the vascular endothelium and its bone marrow precursors. The vascular endothelium growth factors are a family of molecules that induce in a direct and specific manner the formation of new vessels (Leung, D. et al. 1989. Science 246:1306-1309). This family comprehends the Vascular Permeability Factor (abbreviated VPF), that is also known as the Vascular Endothelial Growth Factor A (VEGF-A), the Placental Growth Factor" (abbreviated PLGF), the Platelet-Derived Growth Factors (abbreviated PDGF) A and B, and other molecules structurally and biochemically related to VEGF-A, that have been denominated VEGF-B, VEGF-C, VEGF-D, and VEGF-E (Olofsson, B. et al. 1996. Proc Natl Acad Sci USA 93: 2576-2581; Joukov, V. et al. 1996. EMBO J 15:290-298; Yamada, Y. et al. 1997. Genomics 42:483-488; Ogawa, S. et al. 1998. J Biol Chem 273:31273-31282). VEGF-A is a homodimeric glycoprotein formed by two subunits of 23 kDa (Ferrara, N. et al. 1989. Biochem Biophys Res Comun 161: 851-858). Five isoforms exist, derived from differential splicing of one same ribonucleic acid (RNA). These include two cell membrane bound isoforms (VEGF 189 and VEGF 206) and three secreted as soluble factors (VEGF 121, VEGF 145, and VEGF 165). VEGF 165 is the most abundant in mammal tissues, exception made of heart and lungs where VEGF 189 predominates (Neufeld G et al. 1995. Canc Met Rev 15:153-158). In placenta, expression of VEGF 121 is higher (Shibuya, M. 1995. Adv Cancer Res 67: 281-316). The VEGF family molecules exert their functions and effects by binding to tyrosine kinase class III cell receptors, that include VEGFR1 (Flt1), VEGFR2 (KDR/Flk1) and VEGFR3 (Flt4) (Kaipainen, A. 1993. J Exp Med 178: 2077-2088).

VEGF-A is the most studied and characterized protein of this family and a number of diseases have been described where this protein is related to the pathogenic process (Carmeliet, P. y Jain, R K. 2000. Nature 407: 249-257; Kuwano M, et al. 2001. Intern Med 40: 565-572). Over expression of VEGF-A is related to the growth of tumors of different origin and localization, as well as with their dissemination (Grunstein, J. et al. 1999. Cancer Res 59: 1592-1598). In the particular case of tumors, the cells that express the three basic isoforms of VEGF-A (121, 165 and 189) are the ones with faster in vivo growth (Grunstein, J. 2000. Mol Cell Biol 20: 7282-7291).

VEGF-A has been also related to chronic inflammatory processes as ulcerative colitis and Crohn's disease (Kanazawa, S. et al. 2001. Am J Gastroenterol 96: 822-828), psoriasis (Detmar, M. et al. 1994. J Exp Med 180: 1141-1146), respiratory distress (Thickett, D R. et al. 2001. Am J Respir Crit Care Med 164: 1601-1605), atherosclerosis (Celletti, F L. et al. 2001. Nat Med 7: 425-429), endometriosis (McLaren, J. 2000. Hum Reprod Update 6: 45-55), asthma (Hoshino, M. et al. 2001. J Allergy Clin Immunol 107: 295-301), rheumatoid arthritis and osteoarthritis (Pufe, T. et al. 2001. J Rheumatol 28: 1482-1485), thyroiditis (Nagura, S. et al. 2001. Hum Pathol 32: 10-17), diabetic and newborn retinopathies (Murata, T. et al. 1996. Lab Invest 74: 819-825; Reynolds, J D. 2001. Paediatr Drugs 3: 263-272), macular degeneration and glaucoma (Wells, J A. et al. 1996. Br J Ophthalmol 80: 363-366), tissue edema (Kaner, R J. et al. 2000. Am J Respir Cell Mol Biol 22: 640-641), obesity (Tonello, C. et al. 1999. FEBS Lett 442: 167-172), hemangioma (Wizigmann, S. and Plate, K H. 1996. Histol Histopathol 11: 1049-1061), inflammatory arthropathies (Bottomley, M J. et al. 2000. Clin Exp Immunol 119:182-188) and transplant rejection (Vasir, B. et al. 2001. Transplantation 71: 924-935).

An attractive therapeutic procedure for many of these diseases is based on the inhibition of the activity of the pro-angiogenic factors that stimulate anomaly blood vessel formation, using molecules able to neutralize their effect. Many of the new therapeutic strategies based on angiogenesis inhibition, especially for cancer, are based on the blockade of VEGF-A and/or its receptors. Among the products approved or in clinical trial we can find: (1) monoclonal antibodies that block VEGF-A or the KDR receptor, (2) metalloproteinase inhibitors, such as Neovastat and Prinomastat, (3) VEGF inhibitors as Thalidomide, Suramin, Troponina I, and IFN-α, (4) VEGF receptor blockers as SU5416, FTK787 and SU6668), (5) tumor endothelium apoptosis inducers as Endostatin and CA4-P, and (6) ribozymes that diminish the expression of VEGF or its receptors (Angiozyme).

From all the above mentioned, the antibodies and antibody y fragments that neutralize the pro-angiogenic effects of VEGF-A are the most advanced, in terms of application and acceptance as therapeutic products. In the medical practice, the humanized recombinant antibody Bevacizumab, commercially known as Avastin (Ferrara, N. et al. 2005. Biochem Biophys Res Comun 333: 328-335; Kim, K J. et al. 1992. Growth Factors 7: 53-64), that recognizes human VEGF-A and neutralizes its pro-angiogenic effect, has been approved in several countries for the treatment of different cancers (Allison, M. 2010. *Nature Biotechnology*, 28(9): 879-880). Recently, several countries have approved the use of Ranibizumab (Gaudreault, J. et al. 2005. *Invest Ophthalmol Visual Sci* 46: 726-733), commercially known Lucentis, for the treatment of age-related macular degeneration, in its wet form. Ranibizumab is a recombinant antibody fragment of the Fab type, developed by manipulation of Bevacizumab using genetic engineering. The intravitreal injection of Ranibizumab neutralizes the locally produced VEGF-A, and affects neo-angiogenesis in the deeper layers of the retina, that is the base of this disease. In addition to the examples of Bevacizumab and Ranibizumab, that have already been registered by sanitary authorities, there are reports of other antibodies and antibody fragments that recognize and neutralize human VEGF (Muller, Y. et al. 1997. *Proc Natl Acad Sci USA* 94: 7192-7197; Asano, M. et al. 1998. *Hybridoma* 17:185-190; Vitaliti A. et al. 2000. *Cancer Res* 60: 4311-4314; Brekken, R A. and Thorpe, P E. 2001. *J Controlled Release* 74:173-181; Jayson, G. et al. 2002. *JNCI* 94: 1484-1493; Brekken, R A. et al. 2000. *Cancer Res* 60: 5117-5124; Fuh, G. et al. 2006. *J Biol Chem* 281: 6625-6631; U.S. Pat. No. 5,730,977; WO2008/052489 A1).

2H1 is a human antibody fragment of the single-chain Fv type (abbreviated scFv) that specifically recognizes human VEGF (WO2008/052489 A1). 2H1 was obtained from a human origin scFv filamentous phage display library. The 2H1 scFv is specific for human VEGF-A, but exhibits a low affinity for this molecule. This can be explained considering that the library from which it originated was constructed with naïve variable regions obtained from human lymphoid cells from different sources (peripheral blood, spleen, tonsils, bone marrow) and different healthy individuals (Rojas G., et al. 2005. *Biochem Biophys Res Comun* 336:1207-1213). As it is known in the state of the art, the phage displayed scFv from naive variable region libraries can produce antibodies of medium and low affinity for their specific antigens. This can be more notorious in the case of self antigens, as it is this case (Marks J. D., et al, 1991. *J. Mol. Biol.* 222: 581-597). The medium or low affinity antibody generally corresponds with the presence of a low amount of mutations in the variable regions, with respect to the immunoglobulin germline sequences from which they originated. Low affinity recombinant antibodies have insufficient performance in immunochemical applications and in vivo therapeutic procedures, when compared to similar molecules that have a higher affinity for the same antigen.

Presently, it continues to be a subject of interest the development of new antibodies that neutralize the effects of human VEGF, and that can be used in the therapy of entities that develop with an excessive angiogenesis.

DESCRIPTION OF THE INVENTION

The invention solves the aforementioned problem, as it provides new human recombinant antibodies that specifically recognize human VEGF-A.

The different recombinant antibodies described in this invention exhibit superior immunochemical, biological, and therapeutic performances, when compared to similar molecules derived from the 2H1 scFv antibody fragment. To develop such antibodies, mutations were done in the complementarity determining regions 3 (CDR3) of the VL and VH variable regions of the scFv antibody fragment 2H1. The new mutated variable regions, selected for a better recognition of human VEGF-A using filamentous phage display technology, were combined using genetic engineering techniques to obtain new antibody binding sites with the desired enhanced and novel immunochemical and biological properties. For this work, an analysis of the sequences of the genes encoding for the scFv antibody fragment 2H1 was first made, that indicated that the VL and VH CDR3 had very little changes with respect to the V, D and/or J human original germinal gene regions. This finding explained the low affinity of 2H1 for the antigen.

A particular mutagenesis strategy was then designed, exclusively directed to the gene sequences encoding the CDR3 domains of the VL (8 amino acid residues) and VH (7 amino acid residues) regions of the 2H1 scFv antibody fragment. The *Parsimonius Mutagenesis* technique (abbreviated PM) (Balint, R. y Larrick J. W. 1993. *Gene*, 137: 109-118) was used to induce the mutations. In PM, an analysis of the sequences to mutate is done and the minimum changes that could modify the characteristics of an antibody binding site is done by computer, taking into account existing information on known immunoglobulin sequences available in public databases. Using degenerated synthetic oligonucleotides and the polymerase chain reaction (PCR), PM produces millions of new mutants for the desired gene region, in a very short time.

PM was applied independently on the CDR3 domains of the VL and VH regions of the 2H1 scFv antibody fragment and, using the cloning of the new variable regions in an appropriate phagemid vector, two large scFv antibody fragment libraries were produced (ca. $5 \times 10^8$ individuals), in which the binding sites had been mutated in the aforementioned amino acid sequences (Example 1). In the library denominated #1, the original 2H1 scFv antibody fragment VL region was conserved, associated with millions of new VH regions mutated in CDR3. In the library denominated #2, the original 2H1 scFv antibody fragment VH region was conserved, associated with millions of new VL regions mutated in CDR3.

Phage that displayed the new scFv antibody fragments representative of the two libraries were selected against human VEGF-A, simultaneously using increasing concentrations of soluble 2H1 scFv, to favor the isolation of new scFv antibody fragments with higher affinity for VEGF-A (Example 2).

Starting with the new clones of scFv fragments selected from each of the two libraries, an experimental estimation of their relative recognition of VEGF-A was done by ELISA, with respect to the 2H1 scFv also displayed on phage (Example 2). These experiments indicated which of the mutated VL and VH variable regions delivered superior antigenic recognition characteristics and affinity to the new fragments.

The new variable regions identified were sequenced to determine the nucleotide composition of the new CDR3. In the case of the new CDR3 domains of the VH region, from the best scFv antibody fragments selected from library #1, all these domains had different amino acid sequences, both among them, and with respect to the original VH of the 2H1 scFv antibody fragment (Example 2, Table 2). The scFv antibody fragments with best antigen recognition were denominated 3F3, 3E3 and 4D8, and contain new VH regions. The 3F3 scFv contains the VH denominated by us H6 (SEQ ID NO: 1 for the base sequence and SEQ ID No. 4 for the amino acid deduced sequence). The 3E3 scFv contains the VH denominated by us H5 SEQ ID NO: 2 for the base sequence and SEQ ID No. 5 for the amino acid deduced sequence). The 4D8 scFv contains the VH denominated by us H7 SEQ ID NO: 3 for the base sequence and SEQ ID No. 6 for the deduced amino acid sequence).

In the case of the new CDR3 domains of the VL region, from the best scFv antibody fragments selected from library #2 (Example 2, Table 3), we identified that the mutations in the new scFv antibody fragments were clustered in several positions with respect to the original domain. In 3 out of 4 scFv fragments with the best recognition of human VEGF, 7 of the 8 CDR3 residues were conserved, with the one in position five being the amino acid that varied from one case to other. The results of this analysis indicated that a possibility to increase the contacts between the binding site and the antigen could be further explored by producing additional substitutions in this particular position five. New scFv antibody fragments displayed in phage were then constructed taking as basis a typical VL CDR3 of this group of best binders, where the CDR3 nucleotide encoding for the fifth amino acid was substituted in order to produce the amino acids P, E or D. The new VL region clones that were in this way produced where denominated L1, L2, and L3, respectively. From these substitutions, the one that included the amino acid D was the one that gave as a result a phage displayed scFv antibody fragment with the best antigen recognition, with respect to the other two new mutants, all precedent VL mutants and, of course, the original 2H1 scFv (Example 3, Table 4).

To continue increasing antigen recognition characteristics, we then combined the VH regions H6, H5 and H7, identified as best from library #1, with the new L3 VL region (SEQ ID NO: 7 for the bases and SEQ ID No. 8 for the deduced amino acid sequence). Once displayed on phage these three new scFv antibody fragments, denominated L3H6, L3H5 and L3H7, a comparison of affinity for VEGF-A was conducted, with respect to the 2H1 scFv antibody fragment, and other phage displayed scFv selected from libraries #1 and #2 (Example 4, Table V). This study showed that the three new scFv antibody fragments L3H6, L3H5 and L3H7 displayed on phage, are superior to all other scFv. Among these three, L3H6 is the one exhibiting a better IC50 in the inhibition assay, indicating that it is necessary to add more amount of soluble 2H1 scFv fragment in the assay to inhibit the mean binding of L3H6 to human VEGF.

In different embodiments of this invention, the genes encoding for the variable regions H6 (SEQ ID NO: 1), H5 (SEQ ID NO: 2), H7 (SEQ ID NO: 3) and L3 (SEQ ID NO: 7) were used to produce different types of recombinant antibodies: (a) the soluble scFv fragments denominated scFv L3H6, scFv L3H5 and scFv L3H7, (b) the soluble Fab fragments denominated Fab L3H6, Fab L3H5 and Fab L3H7, and (c) the bivalent antibody-type molecules scFv$_2$-Fc L3H6, scFv$_2$-Fc L3H5 and scFv$_2$-Fc L3H7.

To produce the recombinant antibody fragments scFv L3H6, scFv L3H5 and scFv L3H7, the genes encoding for the VHs regions H6 (SEQ ID NO: 1), H5 (SEQ ID NO: 2) and H7 (SEQ ID NO: 3) were combined with the VL region L3 (SEQ ID NO: 7), interspaced by a linker segment, and in the order VH-linker-VL, using the pACR.1 vector (Example 5). The pACR.1 vector is designed for the expression of recombinant proteins to the bacterial periplasm, and add to the C-terminus end of the molecules a c-myc peptide domain, useful as a tag for analytical purposes, followed by a six histidine domain to facilitate the purification using metal ion affinity chromatography (abbreviated IMAC) (Porath J. 1992. *Prot. Expr. Purif.* 3: 263-281). The antibody fragments scFv L3H6 (SEQ ID NO: 9 for the base sequence and SEQ ID No. 10 for the amino acid sequence), scFv L3H5 (SEQ ID NO: 11 for the base sequence and SEQ ID No. 12 for the amino acid sequence) and scFv L3H7 (SEQ ID NO: 13 for the base sequence and SEQ ID No. 14 for the amino acid sequence), with apparent molecular weight of ca. 29 kDa in sodium dodecylsulfate polyacrylamide gel electrophoresis (abbreviated SDS-PAGE), can be recovered from the culture medium of transformed bacteria and are easily purified using IMAC.

To produce the Fab recombinant antibody fragments Fab L3H6, Fab L3H5 and Fab L3H7, the genes encoding for the sequences contained in variable regions H6 (SEQ ID NO: 1), H5 (SEQ ID NO: 2), H7 (SEQ ID NO: 3) and L3 (SEQ ID NO: 7) were cloned in the pFabHum-1 vector (Example 9). The pFabHum-1 plasmid is a bi-cistronic vector constructed for the expression of Fab fragment with human immunoglobulin CH1 and C Lambda constant regions, to the bacterial periplasm. The vector adds 6 histidines and a c-myc domain to the C-terminus of the cloned molecule. In this plasmid, the H6, H5 or H7 regions were associated genetically to the constant CH1 region, while the L3 was associated to the constant C Lambda region, giving as result the Fab antibody fragments Fab L3H6 (with nucleotide sequences SEQ ID No. 15 and SEQ ID No. 16, that encode the amino acid sequences SEQ ID No. 17 and SEQ ID No. 18), Fab L3H5 (with nucleotide sequences SEQ ID No. 19 and SEQ ID No. 20, that encode the amino acid sequences SEQ ID No. 21 and SEQ ID No. 22), and Fab L3H7 (with nucleotide sequences SEQ ID No. 23 and SEQ ID No. 24, that encode the amino acid sequences SEQ ID No. 25 and SEQ ID No. 26).

The antibody fragments Fab L3H6, Fab L3H5 and Fab L3H7 are expressed in *Escherichia coli* and purified by IMAC from the culture medium of transformed bacteria using IMAC and have apparent molecular weight of ca. 50 kDa in SDS-PAGE, under non denaturing conditions.

The bivalent recombinant antibodies scFv$_2$-Fc L3H6, scFv$_2$-Fc L3H5 and scFv$_2$-Fc L3H7 comprehend the sequences of the antibody fragment scFv L3H6, L3H5 and L3H7, associated in each case with a 3'sequence that encodes for a 10 amino acid linker, followed by a nucleotide sequence that encodes for the hinge, CH2 and CH3 domains of a human IgG1 immunoglobulin. The mentioned antibodies were obtained by cloning the PCR products of the genes that encode for the aforementioned scFv fragments, in the pVSJG-HucFc vector (Example 10). The pVSJG-HucFc vector has been designed for the expression of molecules of the antibody type that comprehend two identical scFv, associated to a human IgG1 type immunoglobulin Fc, in mammalian cells. The molecules scFv$_2$-Fc L3H6 (SEQ ID NO: 27 for nucleotide sequence and SEQ ID No. 28 for the amino acid sequence), scFv$_2$-Fc L3H5 (SEQ ID NO: 29 for nucleotide sequence and SEQ ID No. 30 for the amino acid sequence), and scFv$_2$-Fc L3H7 (SEQ ID NO: 31 for nucleotide sequence and SEQ ID No. 32 for the amino acid sequence), were produced in the supernatant of CHO cells transfected with the corresponding plasmids. The scFv$_2$-Fc molecules purified using protein A or protein G affinity chromatography exhibit apparent molecular weights between 100 and 120 kDa in SDS-PAGE.

The recombinant antibodies object of the present invention are novel with respect to other antibodies and antibody fragments that recognize or neutralize human VEGF-A, including those derived from the original variable regions of the 2H1 scFv antibody fragment. This is because the recombinant antibodies object of the present invention:
(a) Have novel DNA sequences in their variable region CDR3. This makes them different from other antibodies against VEGF-A reported by other authors, as those derived from hybridomas (Kim, K J. et al. 1992. *Growth Factors* 7:53-64; Muller, Y. et al. 1997. *Proc Natl Acad Sci USA* 94:

7192-7197; Asano, M. et al. 1998. *Hybridoma* 17:185-190; Schaeppi, J M. et al. 1999. *J Cancer Res Clin Oncol* 125: 336-342; Brekken, R A. et al. 2000. *Cancer Res* 60: 5117-5124; Brekken, R A. and Thorpe, P E. 2001. *J Controlled Release* 74:173-181), or obtained alter viral transformation of human cells (U.S. Pat. No. 5,730,977), the modification of pre-existing antibodies by genetic engineering (Jayson, G. et al. 2002. *JNCI* 94: 1484-1493; Ferrara, N. et al. 2005. *Biochem Biophys Res Comun* 333: 328-335), and those derived from human antibody fragment libraries (Vitaliti, A. et al. 2000. *Cancer Res* 60: 4311-4314; Fuh, G. et al. 2006. *J Biol Chem* 281: 6625-6631).

With respect to the VL and VH regions of the 2H1 scFv antibody fragment (WO2008/052489 A1), the antibodies described in the present invention are also different. The VH regions H6 (SEQ ID NO: 4), H5 (SEQ ID NO: 5) and H7 (SEQ ID NO: 6) are different in all 7 CDR3 amino acids, with respect to 2H1. The VL region L3 (SEQ ID NO: 8) is different in 3 out of the 8 CDR3 amino acids, with respect to 2H1.

(b) Have immunochemical specificity for human VEGF-A different to those of human Fab antibody fragments obtained from other libraries (Fuh G. et al. 2006. *J. Biol Chem* 281: 6625-6631), and also with that of Bevacizumab. Different from the antibodies described in this invention, Bevacizumab is not capable of recognizing mouse VEGF. Also, Bevacizumab identifies reduced VEGF-A, while the antibodies described in this invention cannot. In examples 6, 7 and 9 of the present invention, it is described how the new recombinant antibodies have also a different and superior recognition of human VEGF-A, with respect to the 2H1 scFv antibody fragment, and the recombinant antibodies derived from 2H1 (WO2008/052489 A1).

(c) The antibody fragment scFv L3H6 and the recombinant antibodies derived from it (Fab L3H6 and scFv$_2$-Fc-L3H6) recognize a functional epitope in human VEGF-A that is different from all others identified by other antibodies that neutralize the effects of human VEGF-A (Muller, Y. et al. 1997. *PNAS USA* 94: 7192-7197; Muller, A Y. et al. 1998. *Structure* 6: 1153-1167; Schaeppi, J M. et al. 1999. *J Cancer Res Clin Oncol* 125: 336-342; Brekken, R A. et al. 2000. *Cancer Res* 60: 5117-5124; Fuh, G. et al. 2006. *J Biol Chem* 281: 6625-6631; WO2005012359; WO2008/052489 A1).

The new functional epitope defined in human VEGF-A by the new recombinant antibodies scFv L3H6, Fab L3H6 and scFv$_2$-Fc-L3H6, described in the present invention, has as critical amino acids the residues K101, E103, R105 and Y25 (Example 11). If these amino acids are substituted, the recognition of the antibodies described in the present invention is severely affected.

The new recombinant antibodies described in the present invention can bind to soluble human VEGF-A, human VEGF-A adsorbed to solid surfaces, or human VEGF-A associated or near to human cells that produce this factor, among the latter, cells present in human tumors that grow in nude (athymic) mice.

The new recombinant antibodies described in the present invention specifically recognize human VEGF-A isoforms 121 and 165, identified mouse VEGF, and block the interaction of VEGF-A with the VEGFR2 receptor, but not with the VEGFR1 receptor. The latter two properties distinguish the new recombinant antibodies described in the present invention from Bevacizumab and Ranibizumab.

The new recombinant antibodies described in the present invention have higher affinity for human VEGF-A that those derived from the 2H1 scFv antibody fragment, as shown in Example 8. In consequence, these new antibodies have a superior performance, with respect to scFv 2H1 and the antibodies derived from 2H1, in tests that measure: (a) the blockage of the association of VEGF and VEGFR2 (Example 7), (b) the inhibition of the proliferation of endothelial cells in culture, under the stimulation of human VEGF-A (Example 12), (c) the inhibition of subcutaneous angiogenesis in mice, induced by Matrigel pellets that contain VEGF (Example 13), and the inhibition of the growth of human tumors transplanted to nude mice (Example 14).

DEFINITION OF TERMINOLOGIES EMPLOYED IN THE PRESENT INVENTION

Antigen Binding Site

The term describes the part of an antibody that interacts specifically with an antigen (or part thereof). An antibody binding site is mainly formed by two antibody variable regions, the light chain (VL) and the heavy chain (VH) variable regions. The antibody binding site is formed by non covalent interactions of the variable regions. The antibody binding site can be artificially stabilized through the linkage of the two variable regions with a peptide that will not interfere with the specific antigen binding properties. This is the case of a fragment of the scFv type. In nature, the antibody binding sites are assembled by the non covalent interaction of the variables regions, reinforced by the non covalent interaction of the CH1 and CL (kappa o lambda) constant domains, and by a disulfide bond established between a cysteine present in CL and another located in the hinge region of the antibody heavy chain. Full native antibodies have two or more identical antigen binding sites.

Recombinant Antibodies

The term describes an immunoglobulin or parts thereof produced fully or in part in a synthetic form, via recombinant DNA techniques or artificial gene synthesis, with specific recognition of an antigen by way of one or more antigen binding sites (Gavilondo, J. and Larrick. J. W. 2000. *Biotechniques* 29: 128-136). Examples of recombinant antibodies are the so-called chimeric and humanized antibodies, in which genetic engineering is used to associate the variable region genes (or parts thereof) obtained from one specie, with immunoglobulin constant regions of another specie. Among recombinant antibodies we can also find the antibody fragments produced by genetic engineering that comprehend one or more antigen binding sites. Examples of recombinant antibody fragments are: (i) the Fab fragment, which included the VL, VH, CL and CH1 immunoglobulin domains; (ii) the Fd fragment, which consists in of the VH and CH1 domains; (iii) the Fv fragment, that consists of the VL and VH of a single antibody; (iv) the scFv fragment, where the VH and VL domains of a given antibody are combined in different order (VH-VL or VL-VH) with a peptide linker that allows the two variable regions to associate and form an antigen binding site (Bird et al. 1988. *Science* 242: 423-426; Huston et al. 1988. *PNAS USA* 85: 5879-5883); (v) "diabodies", that are multivalent or multispecific fragments constructed in a similar fashion to scFv, but with a short peptide linker that does not allow the VH and VL domains of one same molecule to assemble into a binding site, and the latter has to be created by the association of two or more scFv, thus providing for the multivalency (WO94/13804; Holliger P et al. 1993. *PNAS USA* 90: 6444-6448); (vi) other fragments as the dAb (Ward S E et al. 1989. *Nature* 341: 544-546), isolated CDRs, F(ab')$_2$ fragments, nanobodies, and bi-specific scFv dimers (PCT/US92/09965; Hoffiger P and Winter G. 1993. *Current Opinion*

Biotechnol. 4: 446-449; de Haard, H et al. 1998. *Adv. Drug Delivery Rev.* 31:5-31). Some types of fragments, as the scFv and Fab, can be obtained from antibody libraries, where a large synthetic or natural gene repertoire of the variable regions of a specie combine randomly to produce particular associations of variable regions, that are then displayed as antibody fragments in the surface of filamentous phage.

Also considered recombinant antibodies are the "antibody-type" molecules produced by genetic engineering where antibody fragments are assembled to antibody constant regions. For example, it is possible to construct a bivalent "antibody-type" molecule (denominated here scFv$_2$-Fc) by joining a scFv to a region formed by the hinge, CH2, CH3 and in occasions CH4 domains of an immunoglobulin Fc. Depending on the parts involved in its construction, and the presence of glycosilation, the said molecule can exhibit all effector functions associated to the immunoglobulin Fc. Once it is expressed in a suitable host, the scFv$_2$-Fc molecule has two binding sites, represented by two identical scFv.

Finally, recombinant antibodies are also molecules in which the variable regions of the light and heavy chains obtained from one source (i.e. scFv or Fab), are assembled to the constant regions of a human immunoglobulin, for example, CH1, hinge, CH2, CH3 and in occasions CH4, for the heavy chain variable region, and C Kappa or C Lambda for the light chain variable region.

Equivalent Variants of an Antibody

Equivalent variants of an antibody are polypeptide molecules derived from associations and manipulations of the exact sequences of its variable regions that retain the capacity of specifically recognizing the antigen and developing effects on it, and on its biological properties. These polypeptide molecules can take the form of other recombinant antibody fragments, like that in which the VL domain is located before the linker and the VH scFv domains, or other linker segments known in the state of the art are employed, or produced as F(ab')2, Fabc, Facb, dimeric, trimeric or tetrameric scFv fragments (Winter G, Milstein C. 1991. *Nature* 349: 293-299; WO94/13804; de Haard, H et al. 1998. *Adv. Drug Delivery Rev.* 31:5-31). Also, when multivalent molecules are produced through the addition of immunoglobulin derived sequences (Bestagno M et al. 2001. Biochemistry 40: 10686-10692). Equivalent variants of an antibody are also produced when the exact sequences of its variable regions are contained in bispecific antibodies, or in the form of full size antibodies, associated to the constant domains of a human immunoglobulin or from other specie. All these genetic engineering manipulations are known to those skilled in the art in this technical field.

Equivalent variants of an antibody are also considered those molecules or variants produced by the so-called CDR transplant, in which the CDR sequences of the variable regions are placed artificially in a foreign immunoglobulin framework, and this manipulation does not affect the capacity to recognize the original antigen and provoke biological and biochemical effects.

Specificity of an Antibody or its Variant

Refers to a situation in which an antibody or fragment thereof will not significantly bind other molecules different from its specific binding pair (antigen). This term is also applicable to the case where an antigen binding site is specific for a particular epitope that appears in a number of related or unrelated antigens, in which case the antibody binding site will be able to identify the several antigens that bear the mentioned epitope.

Epitope. Functional Epitope

When the antigen is large, an antibody can bind exclusively to a particular portion of the antigen that is denominated epitope. The epitope recognized by an antibody binding site, in the case that the antigen is a protein, can be formed by a lineal amino acid sequence, or can be conformational, that is, that the amino acids in the antigen that interact with the antibody binding site are structurally close in the tertiary structure of the protein, but are not necessarily sequential in its primary structure. In the case of proteins, a given epitope is by nature discrete, defined by a group of specific amino acids that interact with those of the antibody by non covalent bonds. Functional epitope is that one that is determined experimentally through the substitution of specific amino acid in the antigen, and the effect on the loss of antibody recognition (or that of its variants) is assessed by immunochemical methods.

The new antibodies described in the present invention are useful for the prevention of choroideal neovascularization in a non human primate experimental model where the eye damage is caused by laser photocoagulation (Example 16).

Because they block the interaction between VEGF and VEGFR2 receptor, the new antibodies described in the present invention affect the ability of activated endothelial cells and their bone marrow precursors to proliferate, as well as the maintenance of the physiologic stability of the new blood vessels that are formed pathologically in different diseases. This blockade can also affect other biological functions described for human VEGF, as for example its role as negative regulator of the immune response (Chouaib S et al. 1997. *Immunology Today* 18:493-497).

The latter that the new recombinant antibodies described in the present invention are useful for the development of novel therapeutic procedures for diseases that evolve with abnormal or excessive angiogenesis, among which we can find:

(a) Cancer, meaning primary solid tumors and its metastases; these therapeutic possibilities include, and are not limited to: epidermoid tumors, squamous head and neck tumors, colorectal tumors, prostate cancer, breast tumors, lung small cell and non small cell cancers, pancreatic tumors, thyroid cancer, ovary cancer, liver tumors, Kaposi sarcoma, central nervous system neoplasia (neuroblastoma, hemangioblastoma, meningioma, and brain metastasis), melanoma, renal and gastrointestinal carcinoma, rhabdomiosarcoma, glioblastoma and leiomiosarcoma. The recombinant antibodies scFv$_2$-Fc L3H6, scFv$_2$-Fc L3H5 and scFv$_2$-Fc L3H7, described in this invention, showed effect on the growth of human tumors transplanted to nude mice (Example 14). Because the recombinant antibodies described in the present invention posses a novel epitope recognition of human VEGF-A, these are different from other antibodies and anti-angiogenic molecules in their ways to interfere the union of human VEGF-A and its VEGFR2 receptor, that could lead to different in vivo therapeutic effects. It is well documented that it is possible to produce different therapeutic effects in vivo, including a diminution of collateral effects in a human being with cancer, with antibodies produced against the same antigen, but that recognize different epitope or have different affinity (Allan D. G. P. 2005. *The Oncologist* 10: 760-761; Boland, W. K y Bebb, G. 2009. *Expert Opin. Biol. Ther.* 9(9): 1-8).

(b) Eye diseases as age-related macular degeneration in its wet form, the neovascular glaucoma, and the diabetic and newborn retinopathies. The scFv L3H6 and scFv$_2$-Fc L3H6 molecules described in the present invention showed preventive and therapeutic effect (Example 16) on choroidal neovascularization induced by laser burns in a non human primate experimental model, indicating the usefulness of this antibodies for the treatment of age-related macular degeneration (AMD) (Gaudreault, J. et al. 2005. *Invest Ophthalmol Visual Sci* 46:726-733; Costa, R A et al. 2006. *Investig Ophthalmol Visual Sci* 47:4569-4578), and other eye diseases that share similar pathological basis.

(c) Chronic and acute inflammatory processes like asthma, respiratory distress, endometriosis, and atherosclerosis and tissue edema.

(d) Infectious diseases like Hepatitis and Kaposi sarcoma.

(e) Autoimmune diseases like diabetes, psoriasis, rheumatoid arthritis and thyroiditis.

(f) Other several diseases and states, as organ transplant rejection, hemangioma, and angiofibroma.

The recombinant antibodies described in the present invention can be coupled or conjugated to an enzyme or its fragments, to a biological response modifier (BRM), to a toxin or drug, or to radioactive isotopes, that would add to the original molecule a functional characteristics different from its binding to human VEGF-A. The scFv L3H6 molecule described in the present invention was radio labeled and injected to athymic nude mice bearing human tumors (Example 15). It was demonstrated that the molecule lodges in the tumor and remains in the anatomical area even three days after injected. In this way, the recombinant antibodies described in the present invention, coupled to other therapeutic agents, can be the basis of treatment methods that comprehend their administration as medicaments or pharmaceutical compositions. The antibodies chemically or genetically coupled to therapeutic radionuclides, toxins, drugs or BRM, can target the therapeutic effect of the coupled element to anatomical areas with anomalous human VEGF-A concentration, as can be a tumor and its immediate vicinity, and exert a therapeutic effect. The amount to administer, the frequency and treatment intervals depend on the nature and severity of the disease and these decisions are a responsibility of specialists and medical doctors that are based on what is already known in the field.

Another aspect of the present invention is the use of the described recombinant antibodies to produce a pharmaceutical composition that can inhibit angiogenesis and can be used for the treatment of pathological conditions associated to it. Such treatment comprehends the administration of an effective quantity of the described molecules to a human being.

The compositions produced with the recombinant antibodies described in the present invention can be administered individually or in combination with other treatments, being this simultaneous or sequential, all of which depends of the disease to be treated. The pharmaceutical compositions comprehend, in addition to the active ingredient, an accepted pharmaceutical excipient, buffer, stabilization agent or carrier, and other materials well known for those skilled in this technical field. These materials are not toxic, do not interfere with the efficacy of the active ingredient, and their nature depend on the administration route, being this oral, mucosal, or parenteral, for example, by intravenous injection. In a particular embodiment, the compositions in the invention are compositions for controlled release of the recombinant antibodies of the invention, and of the other active ingredients in the composition.

The recombinant antibodies described in the present invention, or its equivalent variants, are produced by expression of the encoding nucleic acid. In consequence, the nucleic acid sequences that encode for any of the described recombinant antibodies are also part of the present invention, as well as the procedures for the expression of said nucleic acid. In a preferred embodiment, the nucleic acid encodes preferentially but not exclusively for the base sequences exemplified in SEQ ID No. 9, SEQ ID No. 11, SEQ ID No. 13 (scFv L3H6, scFv L3H5 and scFv L3H7, respectively); SEQ ID. No. 15, SEQ ID No. 16, SEQ ID. No. 19, SEQ ID. No. 20, SEQ ID. No. 23, SEQ ID. No. 24 (Fab L3H6, Fab L3H5 and Fab L3H7, individual chains, respectively); SEQ ID. No. 27, SEQ ID. No. 29, SEQ ID. No. 31 ($scFv_2$-Fc L3H6, $scFv_2$-Fc L3H5 and $scFv_2$-Fc L3H7, respectively).

For the recombinant expression of the molecules described in the present invention, or its equivalent variants, appropriate vectors can be constructed or chosen, that contain the necessary regulatory sequences, including promoter, terminator, enhancer, polyadenylation sequences, marker genes and other deemed pertinent. The vectors can be plasmids.

EXAMPLES

Example 1

Figure 1:
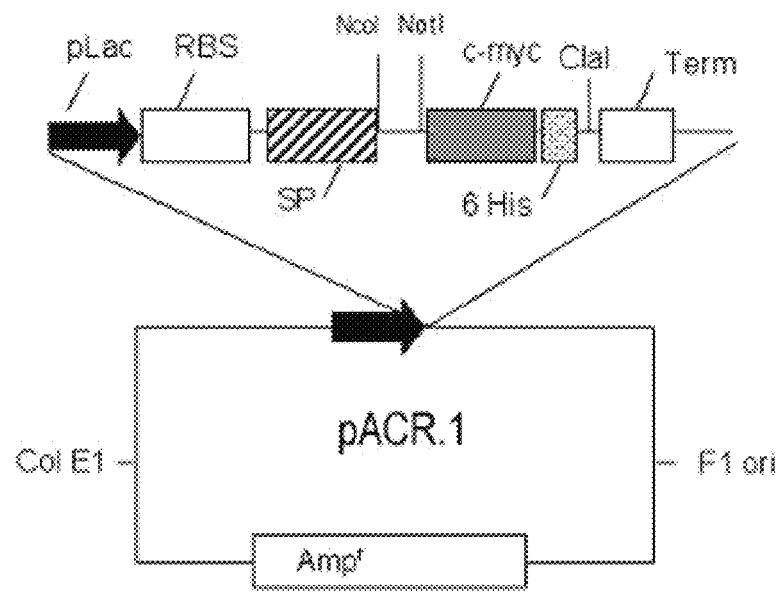
FIG. 1. Schematic representation of the pACR.1 plasmid used for the production of soluble scFv fragments in the *E. coli* periplasm and culture supernatant. The vector has a LacZ promoter, a ribosomal binding site (RBS), and the pelB signal peptide (SP).

Construction of scFv Antibody Fragments Phage Display Libraries Containing Mutated Variable Regions (a) Preparation of Mutated Variable Regions by Polymerase Chain Reaction (PCR)

Sequences LVVRDTE (SEQ ID NO: 33) and LLSYSGAR (SEQ ID NO: 34), corresponding to the CDR3 of VH and VL domains of 2H1 scFv antibody fragment (WO2008/052489 A1), respectively, were used as target for mutagenesis. A set of synthetic oligonucleotides (Table 1) were designed following the principle for *Parsimonius mutagenesis* (P M, Balint, R. and Larrick, J. W. 1993. *Gene*, 137:109-118).

TABLE 1

Design and composition of synthetic oligonucleotides used for mutagenesis of 2H1 VH and VL variable regions by PCR.

| Name | Sequence | |
|---|---|---|
| VH (*) | CATTGTCCCTTGGCCCCAGATT$_{12}$G$_{41}$G$_{12}$A$_{24}$A$_{32}$A$_{32}$C$_{34}$TCTCGCACAGTAATACATGG | (SEQ ID NO: 35) |
| VH-B | GACCACTCGAGTGCACAGCAGGTCCAGCTG | (SEQ ID NO: 36) |
| VH-F | CAGGTGCACAGGCCTGAGGGGCCGAAGAGACGGTGACCATTGTCCCTTGGCCCCAG | (SEQ ID NO: 37) |
| VL (**) | GTCCCTCCGCCGAACACCGGA$_{24}$A$_{42}$A$_{22}$A$_{43}$A$_{13}$A$_{43}$C$_{34}$C$_{34}$GCAGTAATACTCAGCCTCATC | (SEQ ID NO: 38) |
| VL-B | GACCACTCGAGTCGACCAGGCTGTGGTGAC | (SEQ ID NO: 39) |
| VL-F | CAGGTGCACAGCGGCCGCACCTAGGACGGTCAGCTTGGTCCCTCCGCCGAACACC | (SEQ ID NO: 40) |

(*) mix of phosphoroamidites:
| Mix | T | C | A | G |
|---|---|---|---|---|
| 1 | 40% | 20% | 20% | 20% |
| 2 | 20% | 40% | 20% | 20% |
| 3 | 20% | 20% | 40% | 20% |
| 4 | 20% | 20% | 20% | 40% |

(**) mix of phosphoroamidites:
| Mix | T | C | A | G |
|---|---|---|---|---|
| 1 | 46% | 18% | 18% | 18% |
| 2 | 18% | 46% | 18% | 18% |
| 3 | 18% | 18% | 46% | 18% |
| 4 | 18% | 18% | 18% | 46% |

A two-step PCR procedure was performed. In the first PCR step, primers VH-B and VH were used to produce and amplify the mutated scFv VH regions, and primers VL-B and VL for the mutated scFv VL regions (See Table 1).

Phagemid vector pHG-1m (Rojas, G. et al. 2004. *J. Immunol. Meth.* 293: 71-83), bearing the "wild-type" 2H1 scFv antibody fragment gene (denominated 2H1-F; WO2008/052489 A1) was used as template DNA in both cases and KOD thermostable enzyme (Novagen), according to the manufacturer's instructions. In this first PCR 20 amplification cycles were done. Later the reaction products were independently purified from agarose gels using QIAQuick columns (Qiagen) and eluted in water. The DNA concentration was estimated by electrophoresis using DNA standards (NEB). Then, the second PCR step was carried out using primers VH-B and VH-F for VH regions amplification and primers VL-B and VL-F for VL regions amplification (see Table 1). In both cases, 10 ng of purified DNA from the respective first PCR reaction were used. The same thermostable enzyme (Novagen) was used according to the manufacturer's instructions and 15 amplification cycles were done. Later the reaction products were independently purified from agarose gels using QIAQuick columns (Qiagen) and eluted in water. The DNA concentration was estimated by electrophoresis using DNA standards (NEB).

(b) Cloning of the PCR-Mutated Variable Regions in Phagemid Vector.

Samples of the 2H1-F vector and the purified DNA product from mutated VH regions were digested with Sfi I and ApaL I (Fermentas and NEB), purified from agarose gels using QIAQuick columns (Qiagen) and ligated 1:1.5, respectively, using T4 DNA ligase (NEB). The ligation product was purified using QIAquick colums (Qiagen) and eluted in water.

Similarly, the 2H1-F vector and the purified DNA product from mutated VL regions were digested with Sal I and Not I (Fermentas and NEB), purified and ligated as described above.

XL 1-Blue MRF" electrocompetent cells ($1 \times 10^9$/µg, Stratagene) were transformed independently with each ligation in 50 different reaction for each one, plated also independently in 2xYT/ampicillin large dishes, and incubated for 24 hours at 37° C. Reference plates to calculate the library size show that both libraries contained about $5 \times 10^8$ members. The library containing mutated CDR3 VH regions and maintaining the wild-type VL from 2H1 scFv was denominated library #1 while the one with the mutated CDR3 VL regions and the wild-type VH from 2H1 scFv was denominated library #2.

(c) DNA Purification from the Libraries Containing Mutated Variable Regions

Bacterial colonies were scrapped from the plates, pooled according to their origin, and cells pelleted. High purity DNA was obtained from the cell pellets using the MaxiPrep kit (Qiagen), according to the manufacturer's instructions.

Example 2

Selection of scFv Antibody Fragments Displayed on Phage Bearing Mutant Heavy and Light Variable Regions, with Higher Affinity for Human VEGF The DNA of the mutated variable regions libraries was used to independently electroporate TG1 *E. coli* cells, which were then infected with the helper phage M13K07 to produce phages. Phages were purified and conserved in aliquots at −20° C. until used for selection experiments.

For selection, $2 \times 10^{12}$ phages of each library were diluted in PBS-4% skimmed milk with 50 µg/ml of the soluble scFv 2H1 (WO2008/052489 A1), the latter to favor the isolation of scFv on phage with a high affinity for human VEGF-A, higher that scFv 2H1. These mixtures were incubated independently for 5 hours with human GST-VEGF humano (Morera, Y et al. 2006. *Biotechnol. Appl. Biochem.* 44:45-53), immobilized in Maxisorp immunotubes (Nunc). The immunotubes were previously coated with 10 µg/mL of the protein in PBS, at 4° C. during 16 hours, and then blocked with PBS-4% skimmed milk. The unbound phages were eliminated with 20 washes using PBS-0.1% Tween, followed by two PBS additional washes. Then, bound phages were eluted with a 100 mmol/L triethylamine solution for 10 min, and immediate neutralized with 0.5 mol/L Tris (pH 7.5). The eluted phages were amplified in *E. coli* TG1 cells and used as starting material for another selection cycle. This procedure was repeated 2 times under similar conditions. Phages eluted from the first and second selection cycles were used to infect TG1 cells, which are plated. Representative randomly selected bacterial colonies were isolated and infected to produce phage at a 96-well plate scale (Marks, J. et al. 1991, *J. Molec. Biol.* 222:581-587). The capacity of these phage clones that display scFv on their protein III to bind GST-VEGF was evaluated by ELISA. Maxisorp 96-well plates (Nunc) were coated with 10 µg/mL of human GST-VEGF, and then blocked with PBS-4% skimmed milk during 1 hours at 22° C., followed by several washes with a PBS-0.1% Tween 20 solution. Bound phages were detected with and anti-M13 antibody, conjugated to peroxidase (Amersham-Pharmacia) for 1 hour at 22° C. After several washings, the reactions were developed with substrate solution. Absorbance was measured at 492 nm in a microplate reader.

A wide sample (19 or more) of the clones isolated from each library that produced higher absorbance values in ELISA were processed independently to obtain the nucleotide sequences encoding for the scFv (Macrogen, Korea).

Table 2 shows the amino acid sequences deduced from the nucleotide sequences of the heavy chain (VH) variable region CDR3 from clones isolated from of library #1. All obtained sequences (19) were different. In the same Table, for each phage, the IC50 values describe the concentration of soluble scFv 2H1 fragment that is necessary to inhibit the binding of the phage in an ELISA with the solid phase coated with VEGF. For this, Maxisorp 96-well plates (Nunc) were coated with 10 µg/mL GST-VEGF, followed by blocking with PBS-4% skimmed milk. The same amount of phages from each clone to evaluate was mixed with serial dilutions of soluble scFv 2H1 and incubated in the plates for 1 hour at 22° C. After several washes with PBS-0.1% Tween 20, VEGF-bound phages were detected using an anti-M13 antibody, conjugated to peroxidase (Amersham-Pharmacia) for 1 hour at 22° C. Following several washes, the reactions were developed with substrate solution. Absorbance was read at 492 nm in a microplate reader. The absorbance values obtained, versus the concentrations of soluble scFv 2H1 were ploted and the concentration necessary to block 50% (IC50) of the binding of the phage displayed scFv to the immobilized VEGF was calculated in µg/ml. This value is a relative indicator of the affinity of the different clones for the antigen. Higher IC50 values correspond with higher affinity. Table 2 also shows the IC50 value for the original phage displayed scFv 2H1, for comparison purposes. Of the new clones of phage displayed scFv with mutated CDR3 sequences in the heavy chain, those denominated 3F3, 3E3 and 4D8 had the highest relative affinity for human VEGF. These values are between 6 and 10 times higher than that obtained for the original phage displayed scFv 2H1. The VH sequences of these clones were denominated H6 (SEQ ID No. 1 for the base sequence and SEQ ID No. 4 for the deduced amino acid sequence), H5 (SEQ ID No.2 for the base sequence and SEQ ID No. 5 for the deduced amino acid sequence), and H7 (SEQ ID No.3 for the base sequence and SEQ ID No. 6 for the deduced amino acid sequence).

TABLE 2

VH CDR3 sequences and IC50 values of the different mutants selected from the library #1.

| Clone | VH CDR3 sequence | IC50 (µg/ml) | |
|---|---|---|---|
| 2H1 original | LVVRDTE | 5.08 | SEQ ID NO: 33 |
| 3F3 | QGTHNRK | 48.86 | SEQ ID NO: 41 |
| 3E3 | LVHRYRA | 35.08 | SEQ ID NO: 42 |
| 4D8 | PYATDTR | 31.98 | SEQ ID NO: 43 |
| 3C4 | MVNRIPT | 28.97 | SEQ ID NO: 44 |
| 3E1 | PSARDSQ | 21.16 | SEQ ID NO: 45 |
| 3H2 | LTDPGHR | 19.62 | SEQ ID NO: 46 |
| 2B12 | RSSRNAL | 21.05 | SEQ ID NO: 47 |
| 3E12 | LTPTATK | 18.26 | SEQ ID NO: 48 |
| 3D4 | LANGGNK | 16.26 | SEQ ID NO: 49 |
| 3E2 | RVSPDTL | 15.30 | SEQ ID NO: 50 |
| 2A7 | AIRGRGE | 15.79 | SEQ ID NO: 51 |
| 3E10 | LLHSHGK | 15.07 | SEQ ID NO: 52 |
| 3E9 | VNHGYSR | 15.02 | SEQ ID NO: 53 |
| 3E4 | LAVRNPA | 13.51 | SEQ ID NO: 54 |
| 4H3 | SAASGNA | 12.17 | SEQ ID NO: 55 |
| 3E5 | WRFRDDP | 9.06 | SEQ ID NO: 56 |
| 3B10 | LFDTNNL | 7.94 | SEQ ID NO: 57 |
| 4E11 | PGDNDTL | 5.28 | SEQ ID NO: 58 |
| 4F2 | MTAPNIQ | 4.98 | SEQ ID NO: 59 |

Table 3 shows the amino acid sequences deduced from the CDR3 nucleotide sequences of the light chain variable region (VL) from the clones isolated from library #2. The sequence analysis of 21 clones revealed that 13 were different, and 3 repeated patterns that grouped 5, 3 and 3 clones, respectively were seen. Table 3 also shows the IC50 values that describe the concentration of the original soluble scFv 2H1 that is necessary to inhibit the binding of the phage to a solid surface coated with human VEGF, in an ELISA test as that described above. The Table displays the IC50 value for the original phage displayed scFv 2H1, for comparison purposes. The highest IC50 values correspond to clones denominated 1B1, 1H2, 2F6 and 1H3. These values are between 23 and 30 times higher than that obtained for the original phage displayed scFv 2H1.

TABLE 3

VL CDR3 sequences and IC50 values for the different mutants selected from the library #2.

| Clone | IC50 (µg/ml) | VL CDR3 sequence | |
|---|---|---|---|
| 2H1 (original) | 5.08 | LLSYSGA | SEQ ID NO: 60 |
| 1B1 | 151.22 | RLSYALA | SEQ ID NO: 61 |
| 1H2 | 123.59 | RLSYSLA | SEQ ID NO: 62 |
| 2F6 | 119.38 | RLSYNLA | SEQ ID NO: 63 |
| 1H3 (other 2 clones with the same sequence) | 117.11 | ALSYNFS | SEQ ID NO: 64 |
| 2D10 | 65.71 | RLYTSDS | SEQ ID NO: 65 |
| 1D12 | 58.88 | LLSYDRV | SEQ ID NO: 66 |
| 1G4 | 57.68 | LLSYDRS | SEQ ID NO: 67 |
| 2H8 | 46.56 | RLYTAAS | SEQ ID NO: 68 |
| 1E9 (other 2 clones with the same sequence) | 46.24 | LLSYDFS | SEQ ID NO: 69 |
| 1C9 (other 4 clones with the same sequence) | 38.28 | LLAYPLS | SEQ ID NO: 70 |
| 2A10 | 35.81 | LLSYPFS | SEQ ID NO: 71 |
| 2H10 | 10.23 | LLSPDNH | SEQ ID NO: 72 |
| 2F5 | 4.21 | ALSHDFS | SEQ ID NO: 73 |

Example 3

New Mutants of the Light Chain Variable Region CDR3

Taking into consideration the sequences and the IC50 reported in the two tables of example 2, an analysis was done of the possible new mutations to make in the VL CDR3, in order to increase further the relative affinity for the antigen. It was decided to preserve the sequence RLSY(x)LAR due to its conservation in 3 of the 4 best IC50 clones, and to concentrate mutations on the fifth position of this sequence. Planned new amino acids for the mutations in this position were P, D or E, taking into account the characteristics of these particular residues, and whether they appeared in this position or not in other clones.

A two-step PCR similar to that described in Example 1a, was used to fabricate these new mutants, using DNA from clone 2F6 as template and synthetic oligonucleotides as primers.

For the cloning of the new fragments, a sequential digestion of the phagemid vector 2H1-F and the new PCR bands was done, in a procedure similar to what was described in Example 1b. The three new recombinant vectors were transformed independently and five colonies representative of each transformation were selected. DNA was purified from each sample and the presence of the desired mutation was verified. High purity DNA was obtained and used to electroporate independently E. coli TG1 cells that were then infected with M13 helper phage. The resulting phages were purified and tested to determine the IC50, as described above in this same example.

The IC50 values describing the concentrations of the original soluble scFv 2H1 needed to inhibit 50% of the binding of the phages to a solid phase coated with human VEGF, determined in an ELISA test similar to that used above in this same example, are shown in Table 4 for each new phage clone. The value for the original phage displayed scFv 2H1 is also included for comparison purposes. Other previously described clones are also shown. The highest IC50 value corresponds to the new clone L3, that is 73 times higher than that of the original phage displayed scFv 2H1.

TABLE 4

VL CDR3 sequences and IC50 for different phage clones.

| Clone | IC50 (µg/ml) | VL CDR3 sequence | |
|---|---|---|---|
| 2H1(original) | 4.89 | LLSYSGAR | SEQ ID NO: 60 |
| L1 | 11.67 | RLSYPLAR | SEQ ID NO: 74 |
| L2 | 126.20 | RLSYELAR | SEQ ID NO: 75 |
| L3 | 358.10 | RLSYDLAR | SEQ ID NO: 76 |
| 1B1 | 148.73 | RLSYALAR | SEQ ID NO: 61 |
| 1H2 | 119.61 | RLSYSLAR | SEQ ID NO: 62 |
| 2F6 | 114.88 | RLSYNLAR | SEQ ID NO: 63 |
| 1H3 | 109.66 | ALSYNFTR | SEQ ID NO: 64 |

Example 4

Construction of scFv Antibody Fragments Combining Mutated VH and VL Variable Regions for a High Affinity to Human VEGF Restriction digestion and cloning procedures were performed as described above, to obtain 3 new antibody fragments that combine the VL encoding gen from clone L3 (equally denominated L3; SEQ ID No.7 for the nucleotide sequence and SEQ ID No.8 for the deduced amino acid sequence) with those genes, already mentioned in Example 2, encoding the heavy chains: H6 (SEQ ID No.1 for the nucleotide sequence and SEQ ID No. 4 for the deduced amino acid sequence), H5 (SEQ ID No.2 for the nucleotide sequence and SEQ ID No. 5 for the deduced amino acid sequence) and H7 (SEQ ID No.3 for the nucleotide sequence and SEQ ID No.6 for the deduced amino acid sequence). XL 1-Blue MRF'" electrocompetent cells were independently transformed with these 3 new recombinat plasmids and 5 independent colonies from each one were picked and grown to obtain DNA. After confirm the correct sequences, these plasmids were used to independently electroporate TG1 *E. coli* cells, which were then infected with the helper phage M13K07 to produce phages. Phages were purified and used to evaluate the IC50 in ELISA as described in Example 2.

Table 5 shows the IC50 value for each new phage clon that describe the concentration of soluble scFv 2H1 antibody fragment that is necessary to inhibit the binding of the phage in an ELISA with the solid phase coated with VEGF, as described above. The high IC50 value and therefore better antigen recognition correspond to the new clone L3H6.

TABLE 5

CDR 3 sequences and IC50 values for new scFv phage-displayed clones, derived from combinations, respect to corresponding parental clones.

| Combination of mutated variable regions | CDR3 VL sequence | CDR3 VH sequence | Denomination of the new clone | IC50 (µg/ml) |
|---|---|---|---|---|
| L3 + H6 | RLSYDLAR SEQ ID NO: 76 | QGTHNRK SEQ ID NO: 41 | L3H6 | 978.43 |
| L3 + H5 | RLSYDLAR SEQ ID NO: 76 | LVHRYRA SEQ ID NO: 42 | L3H5 | 940.24 |
| L3 + H7 | RLSYDLAR SEQ ID NO: 76 | PYATDTR SEQ ID NO: 43 | L3H7 | 890.11 |
| Parentals clones | CDR3 VL sequence | CDR3 VH sequence | | |
| L3 | RLSYDLAR SEQ ID NO: 76 | LVVRDTE SEQ ID NO: 33 | — | 350.45 |
| 3F3 | LLSYSGAR SEQ ID NO: 34 | QGTHNRK SEQ ID NO: 41 | — | 49.67 |
| 3E3 | LLSYSGAR SEQ ID NO: 34 | LVHRYRA SEQ ID NO: 42 | — | 34.56 |
| 4D8 | LLSYSGAR SEQ ID NO: 34 | PYATDTR SEQ ID NO: 43 | — | 33.01 |

Example 5

Bacterial Expression and Purification of the Antibody Fragments scFv L3H6, scFv L3H5 and scFv L3H7

(a) Cloning of the Antibody Fragments scFv L3H6, scFv L3H5 and scFv L3H7 in the pACR.1 Vector Vector pACR.1 is a plasmid designed for the expression of antibody fragments to the periplasm of *E. coli* (FIG. 1). As principal elements it has a LacZ promoter, a signal peptide, NcoI and Not I restriction sites for the insertion of the fragment encoding gene, a domain encoding for the c-myc peptide, and a sequence that encodes for 6 histidines, the latter for IMAC purification. The DNA corresponding to the phagemids that encode for the displayed scFv antibody fragments L3H6, L3H5 and L3H7 was used as template for three individual PCR reactions. These procedures were done using ProofStart (Stratagene) enzyme and following the instructions of the manufacturer. The synthetic oligonucleotides in Table 6 were used as primers.

TABLE 6

Synthetic oligonucleotides for the amplification and modification of the scFv L3H6 contained in a phagemid vector, for its cloning in the pACR.1 plasmid.

| Oligonucleotide | Sequence | |
|---|---|---|
| Oligo 5' | 5' . . . CTATTCTCCCATG-GCACAG . . . 3' | SEQ ID NO: 77 |
| Oligo 3' | 5' . . . TTCTGTATGAGGTTTTGC . . . 3' | SEQ ID NO: 78 |

Bands of the expected size (700 bp), were obtained from the three amplifications, which were purified from 1% agarose gels using a QIAquick Gel Extraction Kit (QIAGEN). The different DNA were digested with the Nco I and Not I (Promega) restriction enzymes, and repurified for ligation. The pACR.1 vector was similarly digested and repurified, and the digested bands were ligated independently to the vector using T4 DNA ligase (Promega). The ligation reaction products were used to transform E. coli competent cells (XL-1 Blue; Stratagene) by electroporation. The transformed cells were plated in solid selective medium and grown at 37° C. The methods used are widely known (Sambrook, Fritsch y Maniatis. 1989 *Molecular Cloning, A Laboratory Manual, Second Edition*).

Plasmid DNA was purified from colonies of the different transformations (QIAGEN DNA Plasmid MiniPrep kit), checked for the inserted genes by restriction enzyme digestion, and the plasmids of several colonies per transformation were sent for automatic DNA sequencing using primers that hybridize out of the pACR.1 vector cloning region. The consensus sequences were SEQ ID No. 9 for scFv L3H6, SEQ ID No. 11 for scFv L3H5 and SEQ ID No. 13 for scFv L3H7. These sequences describe the fragments as encoding for VH-linker-VL-c myc-histidines. The plasmids representative of these constructions were denominated pACR.1-scFv L3H6, pACR.1-scFv L3H5 and pACR.1-scFv L3H7.

(b) Expression of scFv L3H6, scFv L3H5 and scFv L3H7 in E. coli and Purification BL21 E. coli competent cells were transformed with the plasmids pACR.1-scFv L3H6, pACR.1-scFv L3H5 and pACR.1-scFv L3H7.

The transformations were plated in selective solid medium and allowed to grow for 16 hours at 37° C. A colony representative of each construction was grown in liquid medium and at a 600 nm OD equivalent to 1 induced for 12 hours adding 1 mM of isopropyl-beta-D-thiogalactopiranoside (IPTG) to the medium. The cells were centrifuged and the culture supernatants dialyzed in the coupling buffer ($NaH_2PO4$ 50 mM, 300 mM NaCl, pH 7-8) and applied directly and independently to Agarose-NTA (QIAGEN). After elimination the contaminants with washes with imidazole 10 mM, the bound proteins were eluted with 250 mM imidazole.

Figure 2:
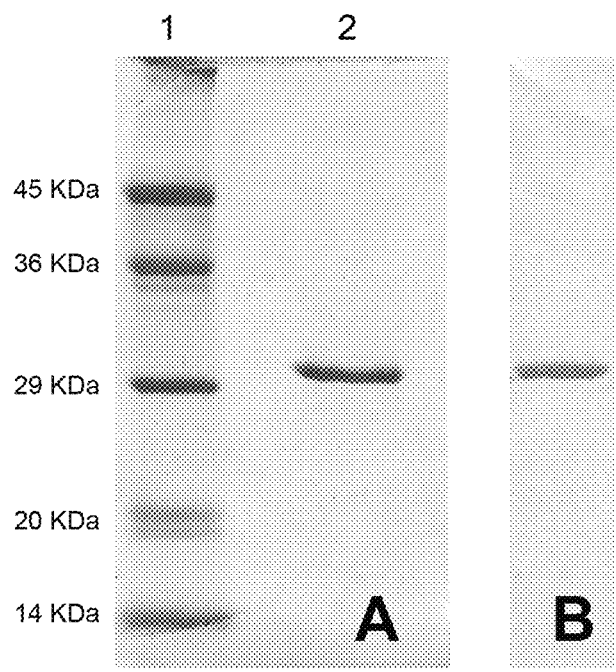
FIG. 2. (A) 12% SDS-polyacrylamide gel electrophoresis with results of the purification of the scFv L3H6 antibody fragment using IMAC, starting from the supernatant of *E. coli* BL-21 cells transformed with the plasmid pACR.1 scFv L3H6; samples prepared in loading buffer with beta-mercaptoethanol. Lane 1: molecular weight markers; Lane 2: elution with 250 mM Imidazole showing the band that corresponds to the fragment, with ca. 29 kDa. (B) Western blot of a replica of the electrophoresis, developed using the anti c-myc antibody 9E10.

The obtained fractions were evaluated by 12% SDS-PAGE and Western Blot, using in the latter the 9E10 monoclonal antibody conjugated to peroxidase that recognizes the c-myc derived peptide that these proteins have. FIG. 2 illustrates, with the case of the antibody fragment scFv L3H6, the results of these procedures. FIG. 2A, Lane 2, shows the high purity of the elution that contains the antibody fragment, which migrates close to 29 kDa. FIG. 2B shows that the purified protein is immunochemically recognized by the 9E10 monoclonal antibody.

Example 6

Characterization by ELISA of the Immunochemical Recognition of Different VEGF Variants by the scFv L3H6, scFv L3H5 and scFv L3H7 Antibody Fragments, in Comparison with scFv 2H1

Nunc 96-well Maxisorp immunoplates were coated with isoforms 121 and 165 of human VEGF-A (Peprotech), mouse VEGF (Peprotech) and P64K-$VEGF_{KDR-}$ (Morera, Y., et al. 2008. *Angiogenesis* 11(4): 381-393), at a concentration of 1 µg/ml in PBS, for 16 hours at 4° C. P64K-$VEGF_{KDR-}$ is a recombinant protein produced in E. coli that is representative of human VEGF mutated in residues 82, 84 and 86 to reduce its interaction with the VEGFR2 receptor (KDR). After blocking the plates with PBS-skimmed milk 4%, the scFv L3H6, L3H5, L3H7 and 2H1 antibody fragments diluted in PBS-skimmed milk 4% were added at a concentration of 10 µg/mL and incubated for 1 h at 22° C. After several washes, 9E10 monoclonal antibody conjugated to peroxidase was added for 1 hour. After washing, the fragments bound to the solid phase were detected by the addition of substrate solution. The absorbance was read at 492 nm in a microplate reader. An unrelated anti-HBsAg scFv was used a negative control (Ayala, M. et al. 1995. *Biotechniques* 18: 832-842).

Table 7 shows that the antibody fragments scFv L3H6, scFv L3H5 and scFv L3H7 have a different recognition pattern, with respect to scFv 2H1 and deliver higher absorbance values (at 492 nm) (average of three wells, taking as reference that produced by the negative control). This is indicative of a higher affinity for the human antigen.

TABLE 7

Absorbance values (at 492 nm) indicative of the recognition of human and mouse VEGF-A by the scFv L3H6, L3H5, L3H7 and 2H1 antibody fragments.

| Fragment | Isoform 121 of human VEGF-A | Isoform 165 of human VEGF-A | Mouse VEGF | P64K-$VEGF_{KDR-}$ |
|---|---|---|---|---|
| scFv 2H1 | 0.691 | 0.665 | 0.090 | 0.764 |
| scFv L3H6 | 2.840 | 2.889 | 1.430 | 2.765 |
| scFv L3H5 | 2.776 | 2.801 | 1.390 | 2.611 |
| scFv L3H7 | 2.541 | 2.512 | 1.125 | 2.467 |
| anti-HBsAg scFv | 0.072 | 0.078 | 0.075 | 0.086 |

Example 7

Blockade of VEGF-Receptor Interaction by the Antibody Fragments scFv L3H6, scFv L3H5, scFv L3H7 and scFv 2H1

Figure 3:
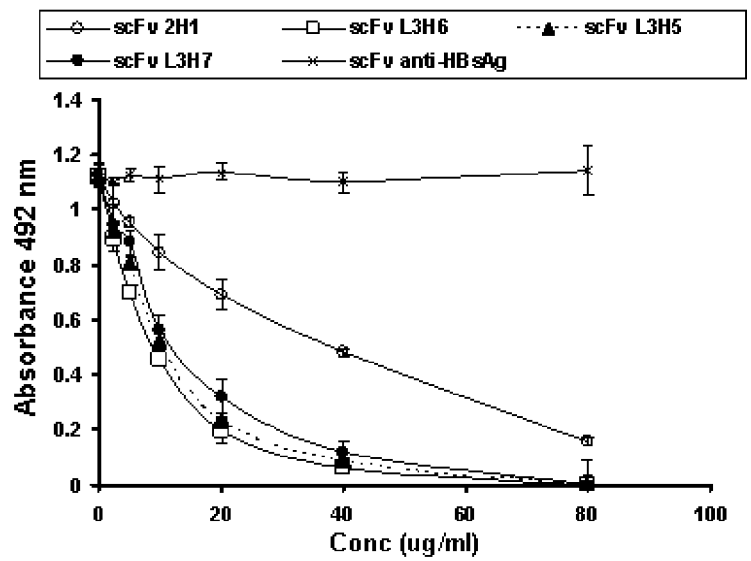
FIG. 3. Competition ELISA to evaluate the capacity of different concentrations of antibody fragments scFv L3H6, scFv L3H5 and scFv L3H7 to block the access of soluble forms of the receptors VEGFR2 (KDR-Fc) and VEGFR1 (FLT-1-Fc) to human VGF-A adsorbed to a solid phase. Detection of bound soluble receptors was made using anti human IgG antibodies conjugated with HRPO. (A) Blocking KDR-Fc. The scFv 2H1 fragment was used as reference and an anti-HBsAg unrelated scFv as negative control. (B) Blockade of FLT-1-Fc. The anti-HBsAg unrelated scFv was used as negative control and the Fab fragment Lucentis® (Ranibizumab) as inhibition control.
Figure 3:
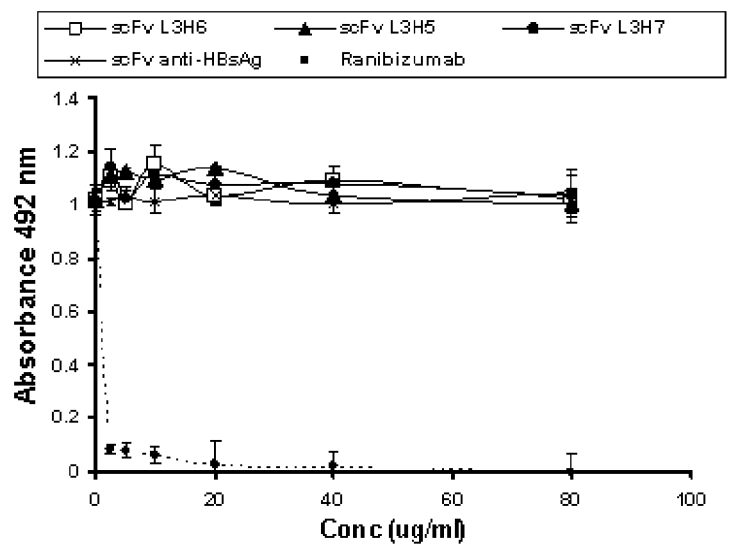

Using an ELISA competition system, we evaluated the ability of purified antibody fragments scFv L3H6, scFv L3H5, scFv L3H7 and scFv 2H1 to block the interaction between human VEGF-receptor and the VEGF recombinant receptors VEGFR2 (KDR) and VEGFR1 (FLT-1). The assays were based in the inhibition of the binding of the soluble receptors KDR-Fc and FLT-1-Fc to human VEGF-A adsorbed to a solid surface, by the addition of increasing concentrations of fragments. Nunc 96-well Maxisorp plates were coated with isoform 121 of human VEGF-A (Peprotech) at a concentration of 1 μg/mL in PBS for 16 hours at 4° C. The plates were blocked, washed, and the wells incubated with increasing concentrations (up to 70 μg/mL) of the purified antibody fragments scFv L3H6, scFv L3H5, scFv L3H7 and scFv 2H1, or PBS-leche al 4%, as well as with 0.5 μg/mL of soluble receptor KDR-Fc (R&D) or FLT-1-Fc (R&D). An unrelated anti-HBsAg scFv was used a negative control (Ayala, M. et al. 1995. *Biotechniques* 18: 832-842), and the Fab fragment Lucentis® (Ranibizumab) as inhibition control. The KDR-Fc or FLT-1-Fc soluble receptors bound to human VEGF-A in the solid phase, were detected with anti-human IgG antibodies conjugated to peroxidase (Sigma). In the case of KDR-Fc (VEGFR2), as shown in FIG. 3A, the antibody fragments scFv L3H6, scFv L3H5 and scFv L3H7 block the binding of the receptor to the human VEGF-A bound to the solid phase, with a clear dose-dependence. The inhibition values for the antibody fragments scFv L3H6, scFv L3H5 and scFv L3H7 are much higher that those observed in the same experiment with the reference scFv 2H1 antibody fragment.

In the case of FLT-1-Fc (VEGFR1), as shown in FIG. 3B, the antibody fragments scFv L3H6, scFv L3H5, scFv L3H7 and scFv 2H1 do not block the binding of the receptor to the human VEGF-A, while Ranibizumab does.

Example 8

Affinity Measurements of the Antibody Fragments scFv L3H6, scFv L3H5, scFv L3H7 and scFv 2H1 for Human VEGF The binding affinity of the antibody fragments scFv L3H6, scFv L3H5, scFv L3H7 and scFv 2H1 for human VEGF was measured using a BIAcore-X (BIAcore, Sweden). A CM5 sensor chip was activated via the covalent binding of human VEGF using N-Ethyl-N'-(3-dimethylaminopropyl) carbodihimide hydrochloride (EDC) and N-hidroxysuccinimide (NHS), according to the manufacturer's instructions. The isoform 165 of human VEGF (PeproTech) was diluted to 5 μg/ml in 10 mmol/l sodium acetate buffer (pH 5.5), and injected at a flow rate of 5 μl/min to obtain approximately 290 response units of coupled protein.

For the kinetic measurements, serial dilutions of the preparations of purified fragments scFv L3H6, scFv L3H5, scFv L3H7 and scFv 2H1, were injected in HBS buffer (10 mmol/l HEPES, 150 mmol/l NaCl, 3 mmol/l EDTA, 0.005% of P20 surfactant, pH 7.4) at 25° C. and at a flow rate of 25 μl/min.

The kinetic parameters and the equilibrium dissociation constants ($K_D$) were calculated using the BIA Evaluation 3.2 software. The binding data were globally adjusted to a Langmuir 1:1 binding model. The obtained $K_D$ are shown in Table 8.

TABLE 8

Equilibrium dissociation constants ($K_D$).

| scFv | $K_D$ |
|---|---|
| 2H1 | 4.57 ± 0.13 × $10^{-7}$ M |
| L3H6 | 2.61 ± 0.11 × $10^{-8}$ M |
| L3H5 | 4.21 ± 0.18 × $10^{-8}$ M |
| L3H7 | 8.73 ± 0.09 × $10^{-8}$ M |

These results demonstrate that the antibody fragments scFv L3H6, scFv L3H5 and scFv L3H7 recognize human VEGF-A with an affinity between 5 and 20 times higher than antibody fragment scFv 2H1.

Example 9

Production and Characterization of the Antibody Fragments Fab L3H6, Fab L3H5 and Fab L3H7

(a) Cloning in the DFabHum-1 Vector and Sequencing

Figure 4:
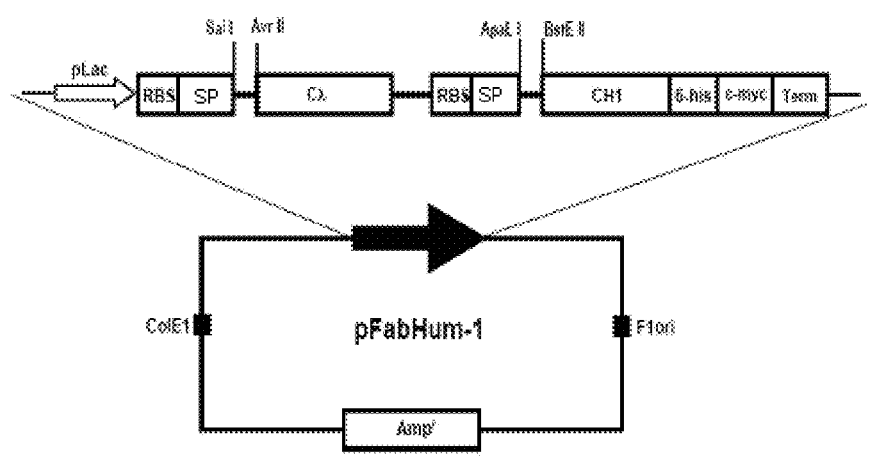
FIG. 4. Schematic representation of plasmid pFabHum-1, used for the production of soluble Fab fragments in the *E. coli* periplasm and culture supernatant. The vector has a LacZ promoter, a ribosomal binding site (RBS), and the pelB and p3M13 signal peptides (PS) in each expression cassette, together with either the constant human immunoglobulin domains CH1 and C Lambda.

FIG. 4 is a schematic representation of plasmid pFab-Hum-1, used to produce soluble Fab antibody fragments in the periplasm and culture medium of transformed *E. coli*. The vector has a LacZ promoter, a RBS, a SP sequence, cloning sites for the light chain variable region (Sal I y Avr II), and the sequence encoding for a human immunoglobulin CA domain, followed by another RBS, SP, and cloning sites for the heavy chain variable region (Apa LI y Bst EII), followed by the sequence encoding for a human immunoglobulin CH1 domain that has been extended to include the first cisteine of the human IgG1 Fc hinge region. The heavy chain variable region-CH1 is expressed associated to a 6 histidine domain for IMAC purification, and a c-myc peptide for analytical purposes, both in the C-terminus, supplied in the vector.

The phagemid DNA that encode for the antibody fragments scFv L3H6, scFv L3H5 and scFv L3H7 were first digested with the Apa LI and Bst EII enzymes to obtain the corresponding VH regions. After verifying gel sizes in 1.5% agarose, the three VH were cloned separately in pFabHum-1, predigested with the same enzymes. Once the clonings were verified by restriction enzyme analysis, the intermediate plasmids (denominated pFab-RVH6, pFab-RVH5 and pFab-RVH7) were replicated, purified and submitted to a new digestion with the Sal I and Avr II enzymes. After verifying gel sizes in 1.5% agarose, the phagemid that encoded for the antibody fragment scFv L3H6 was digested with the Sal I and Avr II enzymes to obtain the unique VL region L3, which was then cloned in the digested plasmids pFab-RVH6, pFab-RVH5 and pFab-RVH7. Once the clonings were verified by restriction enzyme analysis, the three resulting plasmids (denominated pFab L3H6, pFab L3H5 and pFab L3H7) were replicated, purified and submitted to automatic DNA sequencing. The DNA sequence encoding for the two mature protein chains (without the 6 histidine and c-myc domains in the heavy chain) that compose the antibody fragments Fab L3H6, Fab L3H5 and Fab L3H7 correspond to SEQ ID No. 15 and SEQ ID No. 16, SEQ ID No. 19 and SEQ ID No. 20, and SEQ ID No. 23 and SEQ ID No. 24, respectively. The deduced amino acid sequences of these Fab antibody fragments are described in SEQ ID No. 17 and SEQ ID No. 18, SEQ ID No. 21 and SEQ ID No. 22, and SEQ ID. No. 25 and SEQ ID No. 26, respectively.

(b) Expression of Fab L3H6, Fab L3H5 and Fab L3H7 in *E. coli* and Purification

BL21 *E. coli* competent cells were transformed with pFab L3H6, pFab L3H5 and pFab L3H7. The transformations were plated in selective solid medium and allowed to grow for 16 hours at 37° C. A colony representative of each construction was grown in liquid medium and at a 600 nm OD equivalent to 1, induced for Fab expression by adding IPTG to the medium. The cells were centrifuged and the culture supernatants dialyzed in the coupling buffer and applied directly and independently to Agarose-NTA (QIAGEN). After elimination the contaminants with washes, the bound proteins were eluted with 250 mM imidazole.

Figure 5:
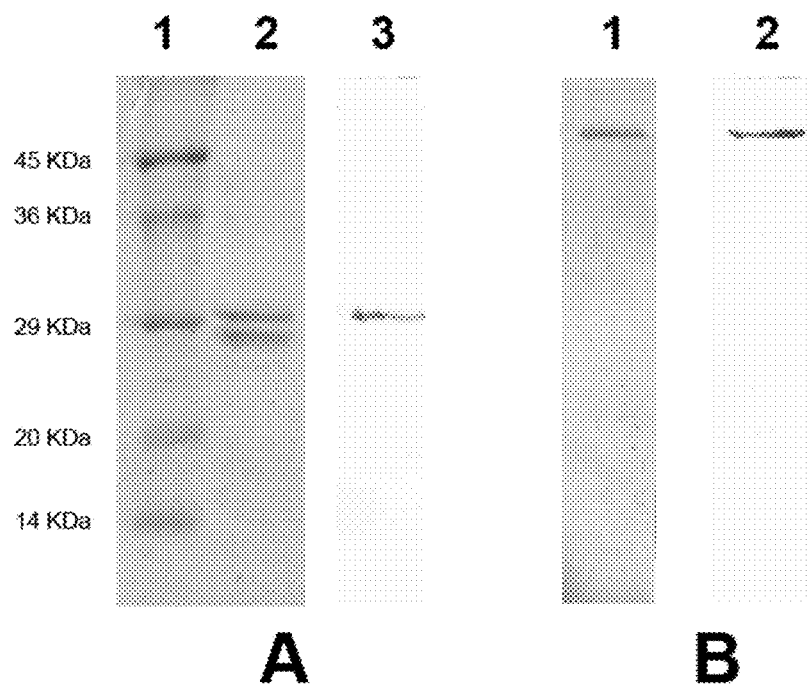
FIG. 5. (A) 12% SDS-polyacrylamide gel electrophoresis with results of the purification of the Fab L3H6 antibody fragment using IMAC, starting from the supernatant of *E. coli* BL-21 cells transformed with the plasmid pFabHum-1 Fab scFv L3H6; samples prepared in loading buffer with beta-mercaptoethanol. Lane 1: molecular weight markers. Lane 2: The two chains of the Fab are visible, with ca. 28-30 KDa. Lane 3: Western blot of a replica of the electrophoresis, developed using the anti c-myc antibody 9E10. Only the heavy chain of the Fab, that contains the c-myc domain, is recognized. (B) Samples prepared in loading buffer without beta-mercaptoethanol (no reduction) Lane 1: The Fab band is apparent, with ca. 50 kDa. Lane 2: Western blot of a replica of the electrophoresis, developed using the anti c-myc antibody 9E10.

Two conditions were employed for the electrophoretic studies. In one case, the samples were incubated in electrophoresis buffer with beta-mercaptoethanol, to produce reduction. In the second case, no beta-mercaptoethanol was used. FIG. 5A shows the results of the purification and Western blot (with the reduced samples and anti c-myc 9E10 antibody for development). In the SDS-PAGE both chains of the Fab can be seen (lane 2) with approximately 28-30 KDa. In Western blot, only the Fab heavy chain is detected, because it contains the c-myc (Lane 3). In FIG. 5B, the samples submitted to no reduction can be seen. The SDS-PAGE shows the band corresponding to the Fab, with approximately 50 kDa (Lane 1), that is recognized in Western blot using the 9E10 conjugated monoclonal antibody (Lane 2).

(c) Characterization of the Recognition of Human VEGF in ELISA, for the Antibody Fragments Fab L3H6, Fab L3H5 and Fab L3H7

The purified antibody fragments Fab L3H6, Fab L3H5 and Fab L3H7 were evaluated for recognition of human VEGF-A in ELISA, using as reference Fab 2H1-32 (WO2008/052489 A1). Nunc 96-well Maxisorp immunoplates were coated with isoforms 121 and 165 of human VEGF-A (Peprotech), mouse VEGF (Peprotech) and P64K-VEGF$_{KDR-}$ (Morera, Y., et al. 2008. *Angiogenesis* 11(4): 381-393), at a concentration of 1 µg/ml in PBS for 16 hours at 4° C. After blocking the plates with PBS-skimmed milk 4%, the Fab antibody fragments diluted in PBS-skimmed milk 4% were added at a 10 µg/mL concentration, and incubated for 1 h at 22° C. After several washes, 9E10 monoclonal antibody conjugated to peroxidase was added for 1 hour. After washing, the fragments bound to the solid phase were detected by the addition of substrate solution. The absorbance was read at 492 nm in a microplate reader. An unrelated Fab, derived from the enzymatic digestion of the anti human EGF receptor antibody Nimotuzumab, also denominated hR3 (Boland, W. K y Bebb, G. 2009. *Expert Opin. Biol. Ther.* 9(9): 1-8).

Table 9 demonstrates that the antibody fragments Fab L3H6, Fab L3H5 and Fab L3H7 have a pattern of recognition different from that of Fab 2H1-32, and exhibit higher absorbance values (492 nm; average of three wells), taking as a reference those produced by the negative control, all which is indicative of a better affinity for the human antigen.

TABLE 9

Absorbance values (492 nm) indicative of the recognition of human and mouse VEGF-A by the antibody fragments Fab L3H6, Fab L3H5, Fab L3H7 and Fab 2H1-32.

| Fragment | Isoform 121 of human VEGF-A | Isoform 165 of human VEGF-A | Mouse VEGF-A | P64K-VEGF$_{KDR-}$ |
|---|---|---|---|---|
| Fab 2H1-32 | 0.589 | 0.601 | 0.091 | 0.704 |
| Fab L3H6 | 2.563 | 2.456 | 1.185 | 2.601 |
| Fab L3H5 | 2.245 | 2.345 | 1.087 | 2.507 |
| Fab L3H7 | 2.221 | 2.201 | 1.096 | 2.417 |
| Fab of hR3 | 0.081 | 0.075 | 0.079 | 0.083 |

Example 10

Generation and Characterization of the Recognition of Dimeric Molecules scFv$_2$-Fc L3H6, scFv$_2$-Fc L3H5 and scFv$_2$-Fc L3H7

(a) Generation of Transfectomas Producing Antibody-Like Molecules scFv$_2$-Fc L3H6, scFv2-Fc L3H5 and scFv$_2$-Fc L3H7

To obtain the antibody-like molecules scFv$_2$-Fc L3H6, scFv$_2$-Fc L3H5 and scFv$_2$-Fc L3H7, a PCR was performed using the plasmids pACR.1-scFv L3H6, pACR.1-scFv L3H5 and pACR.1-scFv L3H7 as templates and the synthetic oligonucleotides shown in Table 10, to modify DNA sequences encoding these antibody fragments make it compatible with the following cloning. This procedure was performed with KOD DNA polymerase (Novagen) according to the manufacturer's instructions.

TABLE 10

Synthetic oligonucleotides for PCR amplification to obtain scFv$_2$-Fc L3H6, scFv$_2$-Fc L3H5 and scFv$_2$-Fc L3H7.

| Oligonucleotide | Sequence | |
|---|---|---|
| Oligo 5' | 5' . . . ACAGGGCTTAAGGAGGTGCAGCTGGTGCAGTCTGG . . . 3' | SEQ ID NO: 79 |
| Oligo 3' | 5' . . . TGTTGTTCTAGAACCTAGGACGGTGACCTTG-GTCCC . . . 3' | SEQ ID NO: 80 |

Figure 6:
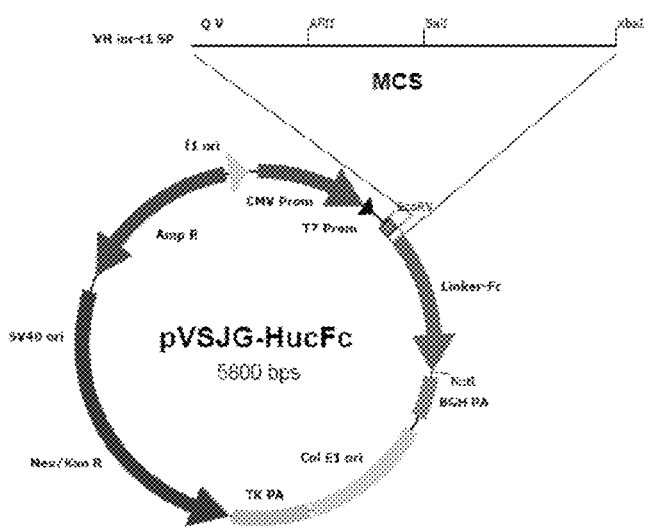
FIG. 6. (A) Schematic representation of plasmid pVSJG-HucFc, used for the production of "antibody-like" bivalent molecules by cloning the scFv fragment gene between the Afl II and Xba restriction sites. (B) Schematic representation of the type of molecule produced by mammalian cells after transfection with this plasmid, once the scFv gene has been cloned in the vector.
Figure 6:
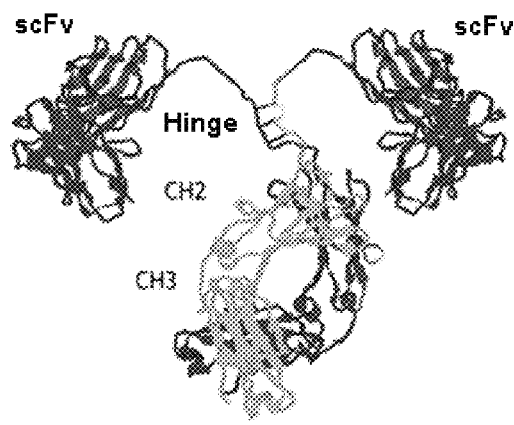
Figure 7:
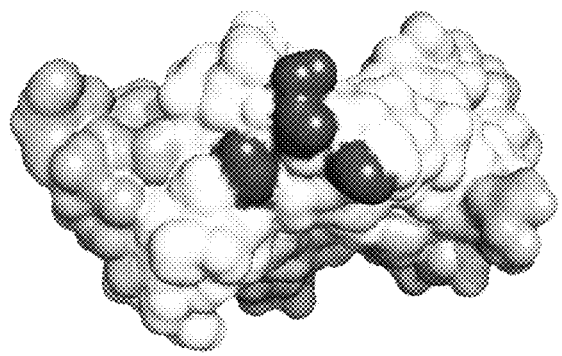
FIG. 7. Representation of the solvent exposed (surface) residues of human VEGF-A, using the PyMol program. The two homodimer chains are represented in white and light grey. In the white chain, the critical amino acid K101, E103, R105 and Y25 related with the epitope recognized by the recombinant antibodies described in the present invention have been highlighted in dark grey. It can be seen that these define a "cluster" or conformational grouping in a zone of the molecule that shows good solvent exposure.

The PCR amplified DNA sequences were cloning into pVSJG-HucFc vector. This vector (FIG. 6A) was designed for the expression in mammalian cells of a polypetide chain containing, in this order: heavy chain signal peptide from a murine monoclonal antibody, followed by the scFv encoding sequence, separated by 10 amino acids (which act as a spacer) consensus sequences encoding for hinge, CH2 and CH3 domains from a human IgG1 immunoglobulin. Due to the signal peptide this polypeptide chain is directed to endoplasmic reticulum where dimerization ocurrs through the formation of covalent disulfide bonds in hinge region and the complementary association of CH2 and CH3 domains. Hinge, CH2 and CH3 domains form a human immunoglobulin Fc region, which is associated by its N-terminal with two identical scFv making a bivalent antibody-like molecule (FIG. 6B).

PCR amplified fragments were digested with Afl II and Xba I restriction enzymes and independently cloned into pVSJG-HucFc vector. Automatic DNA sequencing confirmed the identity of the cloned products. Nucleotide sequences encoding the resulting three mature proteins scFv$_2$-Fc L3H6, scFv$_2$-Fc L3H5 and scFv$_2$-Fc L3H7 are described in SEQ ID No. 27, SEQ ID No. 29, SEQ ID No. 31, respectively, while the deduced amino acid sequences are described in SEQ ID No. 28, SEQ ID No. 30, SEQ ID No. 32, respectively.

The plasmids pVSJG-HucFc L3H6, pVSJG-HucFc L3H5 and pVSJG-HucFc L3H7 were purified under endotoxin free conditions using Pure Yield Plasmid Midiprep kit (Promega). CHO cells (EACC Cat. No. 85050302) were transfected with these plasmids using SuperFect (QIAGEN). Transfectomas were selected in medium containing G418 as a resistance marker. Cell culture supernatants obtained from transfectoma colonies growing with G418 were evaluated by ELISA. Maxisorp 96-well plates (Nunc) were coated with human $VEGF_{121}$ (Peprotech). Supernatants diluted in PBS-2% skimmed milk were added to the plates and $scFv_2$-Fc anti-VEGF molecules were detected with anti-human Fc antibodies conjugated to peroxidase (Sigma). Transfectoma cell colonies with higher secretion levels of $scFv_2$-Fc anti-VEGF molecules detected by ELISA were repeatedly cloned by limiting dilution in medium containing G418 and always testing its secretion capacity by ELISA. After at least two consecutive clonings, three stable clones producing antibody-like molecules were obtained, denominated $scFv_2$-Fc L3H6, $scFv_2$-Fc L3H5 and $scFv_2$-Fc L3H7.

(b) Purification of $scFv_2$-Fc L3H6 $scFv_2$-Fc L3H5 and $scFv_2$-Fc L3H7 Molecules and Evaluation of the Binding Activity to Human VEGF by ELISA Transfectoma clones producing $scFv_2$-Fc L3H6, $scFv_2$-Fc L3H5 and $scFv_2$-Fc L3H7 molecules were cultivated in 162 $cm^2$ flasks in medium containing 0.5% fetal bovine serum. After a high cellular density was obtained the supernatant was collected, 1:1 diluted in 0.1 M sodium phosphate buffer, pH 7.0 and then $scFv_2$-Fc molecules were purified by affinity cromatography using protein A sepharose fast flow 4 (Amersham). Different $scFv_2$-Fc molecules were independently eluted with 0.2 M Glycine buffer, pH 4.0 and immediately neutralized with 1 M Tris, pH 10.0. After dialisis in PBS, protein concentration was calculated by absorbance measurement at 280 nm. The purity was estimated by 12% SDS-PAGE. A sample of purified molecules was tested by ELISA as described in (a), in comparison with unpurified supernatant, showing a proper recognition activity to human VEGF-A.

Example 11

Identification of Functional Epitope on Human VEGF Recognized by scFv L3H6, scFv L3H5 and scFv L3H7 Antibody Fragments To obtain and display human $VEGF_{121}$ mutants were first selected the residues to mutate based on tridimensional structure analysis of the molecule (PDB: 1FLT), location of the zones where recognition by others antibodies are reported and differences between human and murine VEGF. The residues to mutate are shown in Table 11.

TABLE 11

Residues to mutate on human $VEGF_{121}$.

| Mutant | residue | position | substitute |
|---|---|---|---|
| M1 | THR | 31 | TYR |
| M2 | ARG | 56 | GLU |
| M4 | GLN | 37 | ALA |
| M5 | GLU | 38 | ALA |
| M7 | GLU | 73 | LYS |
| M8 | LEU | 97 | THR |
| M9 | THR | 31 | ARG |
| M10 | ARG | 56 | ALA |
| M11 | LYS | 101 | ARG |
| M13 | GLY | 58 | ALA |
| M14 | HIS | 27 | ARG |
| M15 | GLU | 72 | SER |
| M16 | GLY | 88 | SER |
| M17 | ASN | 100 | SER |
| M18 | VAL | 15 | ILE |
| M19 | GLY | 65 | ALA |
| M20 | THR | 71 | ALA |
| M21 | GLU | 73 | ALA |
| M22 | GLU | 103 | ALA |
| M23 | ARG | 105 | ALA |
| M24 | TYR | 25 | ALA |
| M25 | GLN | 22 | ALA |

The mutations were produced by PCR using synthetic oligonucleotides (Table 12) hybridizing on N- and C-terminal encoding sequences to human $VEGF_{121}$ and in specific zones where desired mutations are to be introduced.

TABLE 12

Synthetic oligonucleotides used to produce human $VEGF_{121}$ mutants

| | | |
|---|---|---|
| VEGF-FOR: | tctcacagtgcacaggcacccatggcagaaggaggagggc | SEQ ID NO: 81 |
| VEGF-BAK: | tatttaaagcggccgcccgcctcggcttgtcacattttct | SEQ ID NO: 82 |
| M1-BAK: | ctggaagatgtccaccagatactcgattggatggcagta | SEQ ID NO: 83 |
| M1-FOR: | tactgccatccaatcgagtatctggtggacatcttccag | SEQ ID NO: 84 |
| M2-BAK: | attgcagcagcccccgcattccatcaggggcacacagga | SEQ ID NO: 85 |
| M2-FOR: | tcctgtgtgcccctgatggaatgcggggctgctgcaat | SEQ ID NO: 86 |
| M4-BAK: | gatctcatcagggtactccgcgaagatgtccaccagggt | SEQ ID NO: 87 |
| M4-FOR: | accctggtggacatcttcgcggagtaccctgatgagatc | SEQ ID NO: 88 |
| M5-BAK: | ctcgatctcatcagggtacgcctggaagatgtccaccag | SEQ ID NO: 89 |
| M5-FOR: | ctggtggacatcttccaggcgtaccctgatgagatcgag | SEQ ID NO: 90 |
| M7-BAK: | ctgcatggtgatgttggatttctcagtgggcacacactc | SEQ ID NO: 91 |
| M7-FOR: | gagtgtgtgcccactgagaaatccaacatcaccatgcag | SEQ ID NO: 92 |
| M8-BAK: | catttgttgtgctgggtgaagctcatctctcctatgtgctggcct | SEQ ID NO: 93 |

TABLE 12-continued

Synthetic oligonucleotides used to produce human VEGF$_{121}$ mutants

| | | |
|---|---|---|
| M8-FOR: | aggccagcacataggagagatgagcttcacccagcacaacaaatg | SEQ ID NO: 94 |
| M9-BAK: | cagggtactcctggaagatgtccaccagacgctcgattggatggc | SEQ ID NO: 95 |
| M9-FOR: | gccatccaatcgagcgtctggtggacatcttccaggagtaccctg | SEQ ID NO: 96 |
| M10-BAK: | attgcagcagccccgcacgccatcaggggcacacagga | SEQ ID NO: 97 |
| M10-FOR: | tcctgtgtgcccctgatggcgtgcgggggctgctgcaat | SEQ ID NO: 98 |
| M11-BAK: | ggtctgcattcacaacggtgttgctgtaggaagctcatctctcct | SEQ ID NO: 99 |
| M11-FOR: | aggagagatgagcttcctacagcacaaccgttgtgaatgcagacc | SEQ ID NO: 100 |
| M13-BAK: | ctcgtcattgcagcagcccgcgcatcgcatcaggggcac | SEQ ID NO: 101 |
| M13-FOR: | gtgcccctgatgcgatgcgcgggctgctgcaatgacgag | SEQ ID NO: 102 |
| M14-FOR: | tatcagcgcagctactgccgcccaatcgagaccctggtg | SEQ ID NO: 103 |
| M14-BAK: | caccagggtctcgattgggcggcagtagctgcgctgata | SEQ ID NO: 104 |
| M15-FOR: | ctggagtgtgtgcccactagcgagtccaacatcaccatg | SEQ ID NO: 105 |
| M15-BAK: | catggtgatgttggactcgctagtgggcacacactccag | SEQ ID NO: 106 |
| M16-FOR: | cggatcaaacctcaccaaagccagcacataggagagatg | SEQ ID NO: 107 |
| M16-BAK: | catctctcctatgtgctggctttggtgaggtttgatccg | SEQ ID NO: 108 |
| M17-FOR: | atgagcttcctacagcacagcaaatgtgaatgcagacca | SEQ ID NO: 109 |
| M17-BAK: | tggtctgcattcacatttgctgtgctgtaggaagctcat | SEQ ID NO: 110 |
| M18-FOR: | cagaatcatcacgaagtgatcaagttcatggatgtctat | SEQ ID NO: 111 |
| M18-BAK: | atagacatccatgaacttgatcacttcgtgatgattctg | SEQ ID NO: 112 |
| M19-FOR: | ggctgctgcaatgacgaggcactggagtgtgtgcccact | SEQ ID NO: 113 |
| M19-BAK: | agtgggcacacactccagtgcctcgtcattgcagcagcc | SEQ ID NO: 114 |
| M20-FOR: | ggcctggagtgtgtgcccgcagaggagtccaacatcacc | SEQ ID NO: 115 |
| M20-BAK: | ggtgatgttggactcctctgcgggcacacactccaggcc | SEQ ID NO: 116 |
| M21-FOR: | gagtgtgtgcccactgaggcatccaacatcaccatgcag | SEQ ID NO: 117 |
| M21-BAK: | ctgcatggtgatgttggatgcctcagtgggcacacactc | SEQ ID NO: 118 |
| M22-FOR: | ctacagcacaacaaatgtgcatgcagaccaaagaaagat | SEQ ID NO: 119 |
| M22-BAK: | atctttctttggtctgcatgcacatttgttgtgctgtag | SEQ ID NO: 120 |
| M23-FOR: | cacaacaaatgtgaatgcgcaccaaagaaagatagagca | SEQ ID NO: 121 |
| M23-BAK: | tgctctatctttctttggtgcgcattcacatttgttgtg | SEQ ID NO: 122 |
| M24-FOR: | gatgtctatcagcgcagcgcatgccatccaatcgagacc | SEQ ID NO: 123 |
| M24-BAK: | ggtctcgattggatggcatgcgctgcgctgatagacatc | SEQ ID NO: 124 |
| M25-FOR: | aagttcatggatgtctatgcacgcagctactgccatcca | SEQ ID NO: 125 |
| M25-BAK: | tggatggcagtagctgcgtgcatagacatccatgaactt | SEQ ID NO: 126 |

A two-step PCR was performed to introduce mutations using the plasmid pVEGF (Ojalvo, A. G. et al. 2003. *Electronic J. Biotechnol.* 6, 208-222) containing human VEGF$_{121}$ as template, and the KOD DNA polymerase enzyme (Novagen). In the first step, complementary oligonucleotides to the ends (VEGF-FOR or VEGF-BACK) were used, paired by reaction with the corresponding (M-BACK or M-FOR), per mutant, in a reaction of 15 cycles, according to thermostable polymerase enzyme manufacturer's instructions. In the second PCR, a mixture of the two previous reactions from step 1 was used as template for each mutant. The oligonucleotides employed to introduce the mutation (M-BACK y M-FOR) were diluted 1:100, and used together with the complementary oligonucleotides to the ends (VEGF-FOR or VEGF-BACK). The DNA amplified fragments were purified independently using QIAquick columns (Qiagen) and then double digested with ApaL I and Not-I HF (NEB) during 4 hours. After purification of the reactions with QIAquick columns (Qiagen) and elution in water, digested DNA fragments were cloned in pHG-1m vector (Rojas, G. et al. 2004. *J. Immunol. Meth.* 293: 71-83), previously digested with the same enzymes, treated with phosphatase (NEB) during 1 hour and purified from agarose gel using the same columns. Cloned genes in pHG-1m vector are displayed on the surface of filamentous phages as Protein III fusions. A 1:5 vector: band ratio and T4 ligase (NEB) were used in the ligation reaction for 12 hours at 16° C. TOP 10 F1' cells (Invitrogen) were transformed independently with each ligation by mutant, plated in selective LB medium containing ampicillin and incubated for 24 hours at 37° C. Five colonies were selected from each mutant and grown in 5 ml cultures, in order to purify plasmid using the plasmid Miniprep kit (Qiagen). The DNA was sequenced and the existence of the desired mutations was verified. Sufficient material was obtained for phage expression studies.

TG1 *E. coli* electrocompetent cells were transformed independently with phagemids encoding to each mutant. Phagemids encoding to wild type (WT) VEGF and to a non-related (NR) protein were also included as controls in this experiment. Transformed cells were infected with M13K07 to produce phages. Phages were purified and used to evaluate in ELISA the recognition of each one by different anti-VEGF antibodies: Bevacizumab, rabbit polyclonal antibodies (pAb) and scFv L3H6 antibody fragment. Ninety-six well plates were coated with these antibodies, at 10 μg/mL, in PBS during 16 hours at 4° C. After blocking the plates with PBS-4% skimmed milk, mutants or wild type VEGF displayed on phage were added to the plates and incubated during 1 hour. Plates were washed with PBS-0.1% Tween 20 solution and bound phages were detected with an anti-M13 antibody, conjugated to peroxidase (Amersham-Pharmacia) during 1 hour. Plates were washing again and the reactions were developed with substrate solution. After 20 min, the reaction was stopped with 1M $H_2SO_4$ and the absorbance was measured at 492 nm in a microplate reader.

Figure 8:
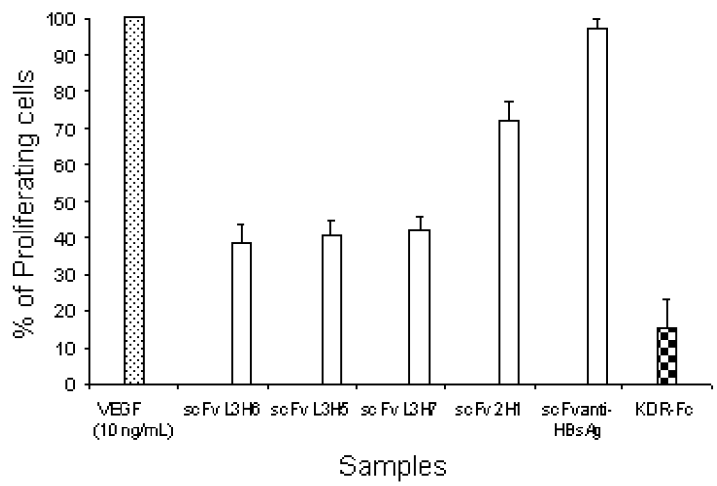
FIG. 8. Capacity of antibody fragments (A) scFv L3H6, scFv L3H5, and scFv L3H7, and bivalent recombinant antibodies (B) scFv$_2$-Fc L3H6, scFv$_2$-Fc L3H5 and scFv$_2$-Fc L3H7 to block the stimulating effect of human VEGF-A on the proliferation of human umbilical cord vein endothelial cells (HuVEC). The antibody fragment scFv 2H1 and the bivalent recombinant antibody scFv$_2$-Fc 2H1 8.2, were used as references. The graphic shows the proliferation relative values, with respect to the addition of VEGF and no antibodies (100%), when samples of: antibody fragments at 40 μg/mL (A), or bivalent molecules at 10 μg/mL (B) are added to the cells. Negative controls were an unrelated anti-HBsAg scFv and the anti-EGF receptor humanized antibody Nimotuzumab. As control of inhibition, soluble KDR-Fc was used. Each bar represents the mean value of the three replicas made by group, with its corresponding standard deviation.
Figure 8:
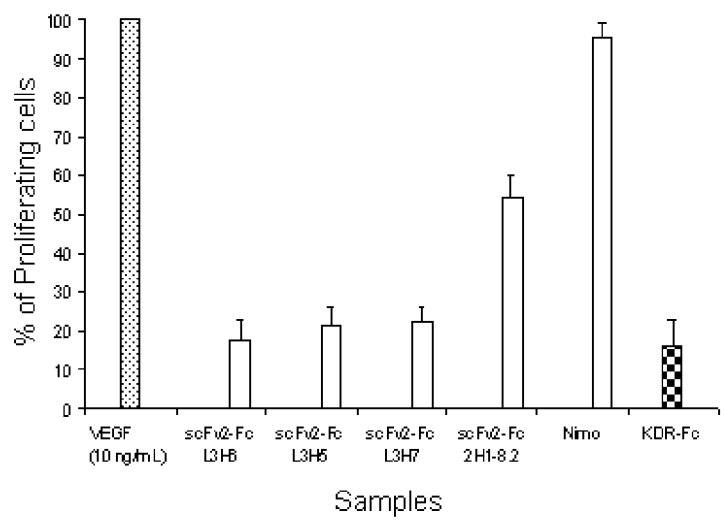

Table 13 shows the immunoreactivity expressed in average absorbance values from three wells for each anti-VEGF antibody, against different mutants, WT-VEGF or NR protein displayed on phage.

TABLE 13

Immunorreactivity expressed in absorbance values for each anti-VEGF antibody, against different mutants and WT-VEGF displayed on phage.

| Phage | Mutation | PAb | scFv L3H6 | Bev. |
|---|---|---|---|---|
| M1 | T31Y | 1.876 | 1.864 | 2.30 |
| M2 | R56E | 0.088 | 0.044 | 0.107 |
| M4 | Q37A | 2.13 | 1.914 | 2.415 |
| M5 | E38A | 1.43 | 1.935 | 1.700 |
| M7 | E73K | 0.879 | 1.912 | 1.599 |
| M8 | L97T | 1.768 | 2.264 | 2.486 |
| M9 | T31R | 2.30 | 1.957 | 2.438 |
| M10 | R56A | 0.163 | 0.043 | 0.180 |
| *M11* | K101R | 2.762 | *0.244* | 2.846 |
| M13 | G58A | 2.864 | 2.109 | 2.547 |
| M14 | H27R | 2.861 | 2.497 | 2.747 |

TABLE 13-continued

Immunorreactivity expressed in absorbance values for each anti-VEGF antibody, against different mutants and WT-VEGF displayed on phage.

| | | | | |
|---|---|---|---|---|
| M15 | E72S | 2.866 | 1.697 | 2.527 |
| M16 | G88S | 2.870 | 2.091 | 0.037 |
| M17 | N100S | 2.888 | 1.899 | 2.663 |
| M18 | V15I | 2.911 | 2.621 | 2.876 |
| M19 | G65A | 2.872 | 1.647 | 2.552 |
| M20 | T71A | 2.702 | 1.632 | 2.218 |
| M21 | E73A | 2.709 | 1.809 | 2.486 |
| *M22* | E103A | 2.819 | *0.078* | 2.409 |
| *M23* | R105A | 2.863 | *0.380* | 2.439 |
| *M24* | Y25A | 2.855 | *0.044* | 2.558 |
| M25 | Q22A | 2.850 | 1.859 | 2.702 |
| WT-VEGF | — | 2.694 | 2.504 | 2.668 |
| NR | — | 0.180 | 0.047 | 0.046 |

In Table 13 mutants M2 (R56E) and M10 (R56A) are highlighted in gray cells, which cause an impairment of the recognition by the three antibodies tested. It is known that this amino acid plays a vital role in structural integrity of human VEGF and in others members of the family such as PLGF and PDGF (Keyt, B. A. et al. 1996. *J. Biol. Chem.* 271: 5638-5646). These mutants were used as internal controls in the experiment, respect to the impairment of overall structure of the molecule. In the same Table 13 data corresponding to mutants: M11 (K101R), M22 (E103A), M23 (R105A) and M24 (Y25A) are highlighted in bold and italics. These mutations noticeably affects the recognition by scFv L3H6 antibody fragment, while the recognition by anti-VEGF polyclonal antibodies obtained in rabbits or by humanized therapeutic antibody Bevacizumab, used in the same experiment, was not affected.

These results indicate that the new functional epitope on human VEGF defined by the scFv L3H6 antibody fragment and by others recombinant antibodies derived from it (Fab L3H6 and $scFv_2$-Fc-L3H6); described in the present invention, precisely have as critical amino acids the residues K101, E103, R105 and Y25.

FIG. 7 shows a schematic representation of the surface residues on human VEGF-A homodimer obtained using PyMol software. This schematic highlights in dark gray in one of the two homodimers the amino acids K101, E103, R105 and Y25, which are critical for the antigen recognition by the new recombinant antibodies, described in the present invention.

Graphic representation of human VEGF-A homodimer obtained using PyMol software shows that the amino acids K101, E103, R105 and Y25 define a conformational cluster in an area of the molecule having a good solvent exposure.

Example 12

Evaluation of the In Vitro Anti-Proliferative Effect of Different Recombinant Antibodies that Recognize Human VEGF, in the Model of Human Umbilical Cord Vein Endothelial Cells (HuVEC), Stimulated with Human VEGF The in vitro anti-proliferative effects of molecules scFv L3H6, scFv L3H5, scFv L3H7, $scFv_2$-Fc L3H6, $scFv_2$-Fc L3H5 and scFv$_2$-Fc L3H7 was determined in a model of human umbilical cord vein endothelial cells (HuVEC), stimulated with human VEGF. The antibodies scFv 2H1 and scFv$_2$-Fc 2H1-8.2 (WO2008/052489 A1) were used as reference, and the scFv anti-HBsAg (Ayala, M. et al. 1995. *Biotechniques* 18: 832-842) and Nimotuzumab (Center for Molecular Immunology, Havana) as negative controls. As inhibition control, soluble KDR-Fc a 1 μg/mL (Sigma) was employed. Briefly, 3,000 HuVEC cells (PromoCell GmbH) were plated per well of a 96-well culture plate (Costar), previously coated with 1% Gelatine (Sigma), in RPMI 1640 medium supplemented with 1% (v/v) fetal bovine serum (Gibco) an grown at 37° C. in 5% $CO_2$ during 72 h hours. The cells were stimulated with only 10 ng/mL of human VEGF-A (Peprotech; growth control arbitrarily defined as 100%), or with 10 ng/mL of human VEGF-A and 40 μg/mL of the scFv fragments, or 10 μg/mL of the bivalent molecules. At the end of the experiment the cells were stained with 0.5% crystal violet in 20% methanol. The plates were washed with water and air-dried. The staining was eluted with a 1:1 solution of ethanol in 0.1M sodium citrate and the absorbance read in a plate reader at 562 nm. The value of absorbance of the basal cell proliferation was considered 100%. The absorbance data derived from the effect of each of the tested molecules were estimated as percentages, with respect to the maximum proliferation control. These proliferation values, with respect to 100%, are indicative of the capacity of a given molecule to inhibit the growth of HuVEC cells stimulated with human VEGF. As shown in FIG. 8A (for the molecules scFv L3H6, scFv L3H5 and scFv L3H7), and 8B (scFv$_2$-Fc L3H6, scFv$_2$-Fc L3H5 and scFv$_2$-Fc L3H7), the recombinant antibodies object of this invention inhibit the proliferation of HuVEC cells at the employed doses. The inhibition produced by each type of recombinant antibody (scFv or divalent molecule) is superior to that produced at equal dose by the antibody fragment scFv 2H1 or the divalent molecule scFv$_2$-Fc 2H1 8.2. In general, the divalent molecules are more efficient in blocking the access of VEGF to cell receptors and, in consequence, inhibit the proliferation of HuVEC cells at lower doses.

Example 13

Figure 9:
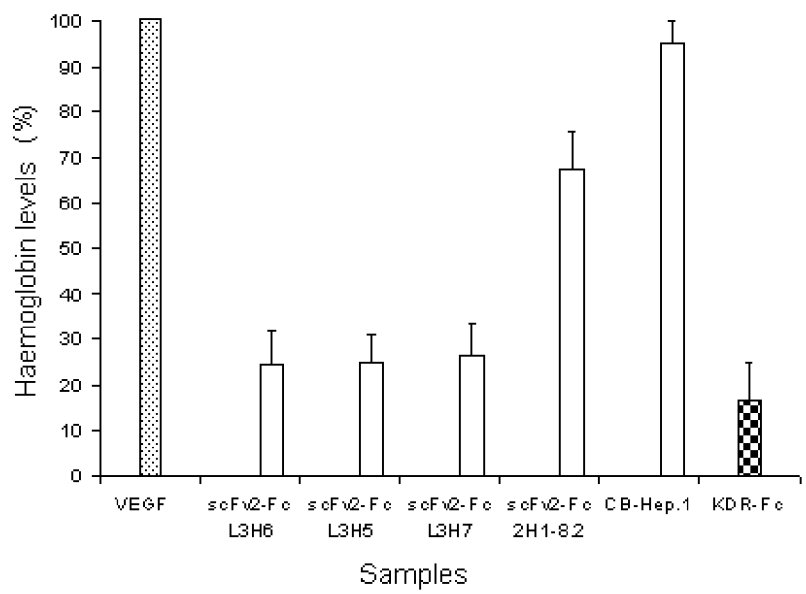
FIG. 9. Capacity of the bivalent recombinant antibodies scFv$_2$-Fc L3H6, scFv$_2$-Fc L3H5 and scFv$_2$-Fc L3H7 to interfere with the angiogenesis stimulating effect of human VEGF-A contained in Matrigel subcutaneous pellets, in C57Bl/6 mice. An unrelated anti-HBsAg monoclonal antibody was used as negative control. As control of inhibition, soluble KDR-Fc was employed. The bivalent molecule scFv$_2$-Fc 2H1 8.2 was used as reference. At the end of the experiment, the contents of the Matrigel pellet are processed for hemoglobin to assess the relative amount of new blood vessels. The graphic present the relative hemoglobin concentration values (100%), with respect to the addition of VEGF and no antibodies. Each bar represents the mean value for the animals included in each group, with its corresponding standard deviation.

Evaluation of the In Vivo Anti-Angiogenic Effect of Different Recombinant Antibodies that Recognize Human VEGF, in the Subcutaneous Matrigel Pellet Model in Mice The in vivo anti-angiogenic effect of bivalent molecules scFv$_2$-Fc L3H6, scFv$_2$-Fc L3H5 and scFv$_2$-Fc L3H7 was studied in the experimental model described by Passaniti et al. (Passaniti A et al. 1992. *Lab Invest.* 67:519-28). For comparison, the divalent antibody-type molecule scFv$_2$-Fc 2H1 8.2 (WO2008/052489 A1) was used. In this model, angiogenesis is induced through the subcutaneous inoculation of C57Bl/6 mice (CENPALAB, Habana) with an extract of proteins of the extracellular matrix (Matrigel, Becton Dickinson) in the presence of pro-angiogenic factors. The animals were divided in groups of 10 and injected subcutaneously in the abdominal region with 500 μL of Matrigel containing 200 ng of human VEGF (Peprotech), 100 μg of the molecules to be tested, including an unrelated antibody (CB-Hep.1, anti-HBsAg, Heber Biotec, Havana), or 10 μg of KDR-Fc (Sigma), as inhibition control. After six days the animals were sacrificed, the Matrigel pellets extracted, and the hemoglobin contents of each determined by the Drabkin method using the Drabkin's reagent kit (Sigma) according to the manufacturer's instructions. Molecules scFv$_2$-Fc L3H6, scFv$_2$-Fc L3H5 and scFv$_2$-Fc L3H7 2 inhibit significantly (p<0.001) the vascularization induced by human VEGF in the Matrigel pellets, correlating this with the lowering of hemoglobin contents. The inhibition values achieved are 3 times higher that those produced by the recombinant antibody scFv$_2$-Fc 2H1 8.2, as can be seen in FIG. 9.

Example 14

Evaluation of the In Vivo Anti-Tumor Effect of Recombinant Antibodies scFv$_2$-Fc L3H6, scFv$_2$-Fc L3H5 and scFv$_2$-Fc L3H7 in Nude Mice Xenotransplanted with A673 Human Tumor Rhabdomiosarcoma Cells Angiogenesis induced by the tumor and some tumor stroma cells is essential for tumor growth and dissemination. The main mediator of this pro-angiogenic effect is the VEGF produced by these cell elements. Because of this, a model used for the assay of anti-angiogenic substances is that of the inhibition of tumor growth in animals. Because the new antibodies described in this patent preferably identify human VEGF, the tumor growth model in mice is done inoculating human tumor cells to isogenic athymic mice (nude mice; nu/nu). In the experiment, we used 5 groups of 5 nu/nu athymic mice of the BALB/c strain (CENPALAB, Havana), with 8-10 weeks of age. The treatment groups were distributed among the recombinant antibodies scFv$_2$-Fc L3H6, scFv$_2$-Fc L3H5 and scFv$_2$-Fc L3H7, the recombinant molecule scFv$_2$-Fc 2H1-8.2 (WO2008/052489 A1) as reference, and the anti HBsAg CB-Hep.1 murine monoclonal antibody (Heber Biotec, Habana) as negative control, all at a dose of 2.5 mg/kg in PBS pH 7.2. Mice were injected subcutaneously with $1.5 \times 10^7$ human A673 tumor cells (ATCC, CRL 1598) in the right dorsal zone. This high cell inoculum, together with the used treatment dose, was employed to rapidly demonstrate differences in the anti-tumor efficacy of the different tested antibodies. When the tumors achieved volumes of 200 mm$^3$ mice were randomized in 5 groups of 5, and the treatment started as indicated for each experimental group. The administrations were done intraperitoneally, in a volume of 200 μL, every 2 days during 3 weeks. The follow up of tumor growth was done with measurements of the highest (length), and lowest (width) tumor diameters, using a digital caliper. The tumor volumes were calculated as: tumor volume (mm$^3$)=0.52×length (mm)× width$^2$ (mm). Tumor volumes along the observation period were compared using the one way ANOVA stadigraph and a Bonferroni post-test. After the established treatment period, the animals were sacrificed and the tumors were surgically removed and histologically analyzed using Hematoxiline and Eosine.

Figure 10:
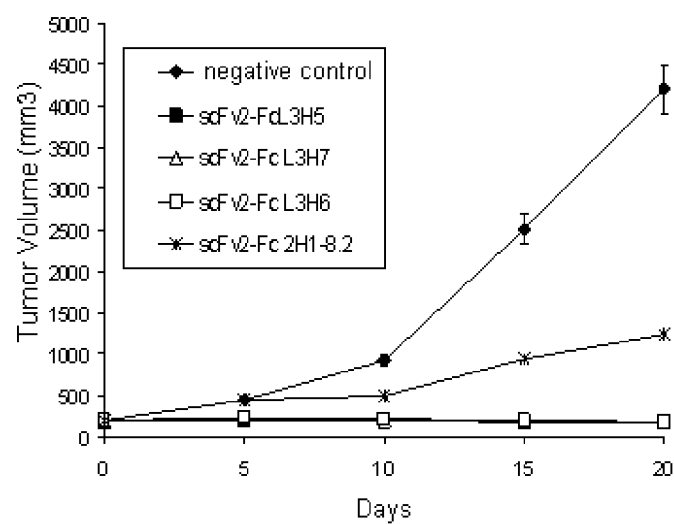
FIG. 10. Effect of the intraperitoneal injection of the bivalent molecules scFv$_2$-Fc L3H6, scFv$_2$-Fc L3H5, scFv$_2$-Fc L3H7 and scFv$_2$-Fc 2H1 8.2 at the 2.5 mg/kg of weight dose, on the growth of subcutaneous tumors derived from the inoculation of the human tumor cell line A673 to nude mice. Dots in the curves are the mean tumor values estimated for the 5 animals per group. As negative control, the unrelated CB-Hep.1 monoclonal antibody was used, at the same dose.

As shown in FIG. 10, all animals inoculated with scFv$_2$-Fc L3H6, scFv$_2$-Fc L3H5 and scFv$_2$-Fc L3H7 showed an almost total control of tumor growth, with respect to the negative control. The figure also shows that the new recombinant antibodies that are object of this invention were superior in performance with respect to the recombinant antibody scFv$_2$-Fc 2H1 8.2. The histological analysis showed that the tumors of animals treated with scFv$_2$-Fc L3H6, scFv$_2$-Fc L3H5 and scFv$_2$-Fc L3H7 had a significant reduction in vascular density, a reduction in the diameter of blood vessels, an increase in tumor cell apoptosis, and a reduction in mitotic figures.

Example 15

Capacity of the $^{131}$I-Radiolabelled scFv L3H6 Fragment to Lodge Selectively in the Tumor Area in Nude Mice Inoculated with Human Tumor Cells of the Rhabdomiosarcoma Line A673

To determine the capacity of the scFv L3H6 fragment to lodge in the area corresponding with tumor growth of A673 cells, this fragment, and a negative control (a murine anti-Hepatitis B surface antigen scFv; scFv-Hep.1; Ayala, M. et al. 1995. Biotechniques 18: 832-842) were labeled with $^{131}$I (Amersham, UK) using the Iodogen procedure (Fraker P J, Speck J C Jr. 1978. *Biochem Biophys Res Comm* 80:849-857) for final specific activities of 1.51 MBq/5 µg and 1.55 MBq/5 µg, respectively.

The radiolabelled products were analyzed in thin layer chromatography to detect incorporation into protein, reporting values of 93 and 95% of radioactivity, respectively. The capacity of the radiolabelled products to detect their corresponding antigens (human VEGF and HBsAg) was studied in a system where polystyrene immunotubes were coated with isoform 121 of human recombinant VEGF (5 µg/mL; Peprotech), or recombinant HBsAg (5 µg/mL; Heber Biotec, Havana), that were then blocked, and placed in contact with samples of the radiolabelled fragments of the corresponding specificity, adjusted to the amounts that could be theoretically captured by the solid phase. After incubations and washings we determined that the solid phase was capable of binding 87.3% and 84.5% of radioactivity, for the scFv L3H6 and the scFv-Hep.1, respectively, showing that the radiolabelling procedure did not change importantly the biological activity of the fragments.

To study the biodistribution we used 30 nu/nu mice. The animals were inoculated subcutaneously with 5×10$^6$ human tumor cells of the A673 culture line in the right dorsal zone. When the tumors achieved volumes of around 300 mm$^3$ the animals were randomized in 6 groups of 5 animals and treatment started. Mice were injected by the tail vein with the radiolabelled product (15 with scFv L3H6 and 15 with scFv Hep.1), and sacrificed in groups of five, for each product, after 24, 48, and 72 hours. Tumor, spleen, liver, kidney, intestine, muscle, bone marrow and blood were removed by surgery or sampled. The accumulation of radioactivity was expressed as percentage of the injected dose per gram of tissue. Calibration was done using a standard sample of the injected dose. Radioactivity was measured using a scintillation gamma counter.

Table 14 shows the tumor:blood radioactivity ratio, calculated from the measurements made in these tissues. The experiment shows that between 24 and 72 hours, the scFv L3H6 fragment is preferentially localized in tumor tissue, different from the unspecific scFv Hep.1 fragment. No specific deposit of radiolabelled scFv L3H6 was found in other tissues different from the tumor; after 48 hours of the injection.

TABLE 14

Tumor:blood radioactivity ratio of nude mice transplanted with the A673 human tumor cells, that express human VEGF.

| Molecule | 24 hours | 48 hours | 72 hours |
|---|---|---|---|
| scFv L3H6 | 25.5 | 32.0 | 46.5 |
| scFv-Hep.1 | 0.4 | 1.0 | 0.7 |

Each ratio was calculated from the mean values derived from the tissues recovered from 5 mice. These results suggest that scFv L3H6 can specifically localize anatomical areas where a large local concentration of human VEGF exists, and is therefore useful to specifically transport to this area different therapeutic products, as a radioactive isotope or eventually a drug or toxin.

Example 16

Prevention of Experimental Choroidal Neovascularization (CNV) in Non Human Primates Using the scFv L3H6 Fragment and the Bivalent Molecule scFv$_2$-Fc L3H6

As a model for experimental choroidal neovascularization (CNV) we employed that reported by Krzystolik et al. (Krzystolik M. G., et al. 2002. *Acta Ophthalmol*, 120:338-346). Six cynomolgus monkeys (*Macaca fascicularis*, CENPALAB, Havana) were maintained and manipulated according to the Good Laboratory Animal Practice guidance of the institution. The animals were anesthetized for all procedures with intramuscular injections of ketamine hydrochlorate, acepromazine maleate, and atropine sulphate. Topical anesthesia with proparacaine hydrochlorate was also used. Anesthesia before enucleating and euthanasia was done with intravenous sodium pentobarbital. The CNV membranes were induced in the macula using argon laser burns, assuring the procedure produced a blister and a small hemorrhage, with a point of application between 50 and 100 µm. Photography and fluorescent angiography were used to detect and measure the extension and characteristics of the lesions. The eyes of the animals were checked in different days, before and after application of the fragment and placebo and the laser burn procedure, as well as at the end of the experiment, that ended with enucleating and animal sacrifice.

The animals were divided in two groups of 3, according to the molecule to be studied: the scFv L3H6 antibody fragment or the bivalent molecule of immunoglobulin type scFv$_2$-Fc L3H6. The right eye of each animal received 300 µg of scFv L3H6 or scFv$_2$-Fc L3H6, according to the group, in 50 µL of PBS through intravitreous injection, while the left eye was only injected with the vehicle. The eyes received 2 injections before laser treatment (days 0 and 14). On day 21, all eyes received the laser treatment for the induction of CNV. The injection was repeated in each eye in day 2 with the specific product or vehicle. Three weeks after laser induction (day 42), the animals received intravitreous injections, this time all with the scFv L3H6 fragment or the scFv$_2$-Fc L3H6 molecule, according to the group, to end with a final similar injection on day 56.

In the phase I of treatment (before day 42), the studies showed a reduction in the onset of grade 4 lesions in the eyes where scFv L3H6 or scFv$_2$-Fc L3H6 were administered, in comparison with the respective control eyes, all of which suggests that the molecules help in the prevention of CNV. In the second phase of treatment, when all eyes received scFv L3H6 or scFv$_2$-Fc L3H6, we detected a reduction in grade 4 lesions that suggests that the fragment and the bivalent molecule are also beneficial for established lesions.

INCORPORATION OF SEQUENCE LISTING

Incorporated herein by reference in its entirety is the Sequence Listing for the above-identified Application. The Sequence Listing is disclosed on a computer-readable text file titled "Second_Revised_SequenceListing_976-83PC-TUS.txt", created on Aug. 15, 2016. The sequence.txt file is 70.1 KB in size.

The invention claimed is:

1. A recombinant antibody comprising a heavy chain variable and a light chain variable wherein: i) the heavy chain variable region encoded by a nucleotide sequence is selected from the group consisting of SEQ ID NO: 1, SEQ ID NO: 2 and SEQ ID NO: 3, and the light chain variable region is encoded by the nucleotide sequence SEQ ID NO: 7, or ii) the heavy chain variable region comprises an amino acid selected from the group consisting of SEQ ID NO: 4, SEQ ID NO: 5 and SEQ ID NO: 6, and the light chain variable region comprises with the amino acid sequence of SEQ ID NO: 8.

2. The recombinant antibody according to claim 1 wherein the antibody binds to K101, E103, R105 and Y25 on human Vascular Endothelial Growth Factor A (VEGF-A).

3. The recombinant antibody according to claim 2 wherein: i) the heavy chain variable region is encoded by the nucleotide sequence SEQ ID NO: 1 and the light chain variable region is encoded by the nucleotide sequence SEQ ID NO: 7, or ii) the heavy chain variable region comprises the amino acid sequence SEQ ID NO: 4, and the light chain variable region comprises the amino acid sequence of SEQ ID NO: 8.

4. The recombinant antibody according to claim 1 wherein the antibody interferes with the in vitro stimulatory effects, and the in vivo pro-antigenic effects of the different isoforms of human VEGF-A.

5. The recombinant antibody according to claim 1 wherein the antibody is single chain Fv (scFv) fragment.

6. The recombinant antibody according to claim 5 wherein the scFv antibody: i) is encoded by a nucleotide sequence selected from the group consisting of SEQ ID NO: 9, SEQ ID NO: 11 and SEQ ID NO: 13; or ii) comprises an amino acid sequence selected from the group consisting of SEQ ID NO: 10, SEQ ID NO: 12 and SEQ ID NO: 14.

7. The recombinant antibody according to claim 1 wherein the antibody is Fab fragment.

8. The recombinant antibody according to claim 7 wherein the Fab fragment comprises a heavy chain variable region and a light chain variable region wherein the heavy and light chain are: i) encoded by pairs of nucleotide sequences selected from the group consisting of SEQ ID NO: 15 and SEQ ID NO: 16, SEQ ID NO: 19 and SEQ ID NO: 20, or SEQ ID NO: 23 and SEQ ID NO: 24 or ii) wherein the heavy chain variable region and the light chain variable region are pairs of amino acid sequences selected from the group consisting of SEQ ID NO: 17 and SEQ ID NO: 18, SEQ ID NO: 21 and SEQ ID NO: 22, or SEQ ID NO: 25 and SEQ ID NO: 26.

9. A recombinant antibody wherein the antibody: i) is encoded by a nucleotide sequence selected from the group consisting of SEQ ID NO: 27, SEQ ID NO: 29 and SEQ ID NO: 31; or ii) the antibody comprises an amino acid sequence selected from the group consisting of SEQ ID NO: 28, SEQ ID NO: 30 and SEQ ID NO: 32.

10. A conjugate antibody comprising any one of the recombinant antibody according to claim 1, wherein the antibody is conjugated with a radioactive isotope, a chemical agent, or a biological agent.

11. The recombinant antibody according to claim 1 wherein the antibody is produced in recombinant bacteria or in mammalian cells.

12. A vector that encodes for the recombinant antibody according to claim 1, wherein said vector is capable of integrating into host cells.

13. A pharmaceutical composition comprising the recombinant antibody of claim 1.

14. The pharmaceutical composition according to claim 13 further comprising a controlled release agent.

15. A method for treating eye disease that evolve with choroidal neovascularization (CNV) as age-related macular degeneration in a human subject in need thereof, said method comprising administering to said subject an antibody encoded by the nucleotide sequence of SEQ ID NO: 9, SEQ ID NO: 11, SEQ ID NO: 13, SEQ ID NO: 27, SEQ ID NO: 29 or SEQ ID NO: 31 or the antibody comprising an amino acid sequence of SEQ ID NO: 10, SEQ ID NO: 12, SEQ ID NO: 14, SEQ ID NO: 28, SEQ ID NO: 30 or SEQ ID NO: 32.

16. A method for in vivo diagnosis of malignant tumors and their metastases in a human subject in need thereof, said method comprising administering to said subject an antibody encoded by the nucleotide sequence of SEQ ID NO: 9, SEQ ID NO: 11 or SEQ ID NO: 13 or the antibody comprising an amino acid sequence of SEQ ID NO: 10, SEQ ID NO: 12 or SEQ ID NO: 14.

17. The method according to claim 15, wherein said eye disease is selected from the group consisting of age-related macular degeneration in its wet form, neovascular glaucoma, and diabetic and newborn retinopathies.

* * * * *

SEQUENCE LISTING

<160> NUMBER OF SEQ ID NOS: 126

<210> SEQ ID NO 1
<211> LENGTH: 354
<212> TYPE: DNA
<213> ORGANISM: Artificial Sequence
<220> FEATURE:
<223> OTHER INFORMATION: Synthetic Sequence

<400> SEQUENCE: 1

```
cagcaggtcc agctggtgca gtctggagca gaggtgaaaa agccggggga gtctctgaag    60
atctcctgta agggttctgg atacagcttt accagctact ggatcggctg ggtgcgccag   120
atgcccggga aaggcctgga gtggatgggg atcatctatc ctggtgactc tgataccaga   180
tacagcccgt ccttccaagg ccaggtcacc atctcagccg acaagtccat cagcaccgcc   240
tacctgcagt ggagcagcct gaaggcctcg gacaccgcca tgtattactg tgcgagacag   300
ggtactcata accgcaaaat ctggggccaa gggacaatgg tcaccgtctc ttcg         354
```

<210> SEQ ID NO 2
<211> LENGTH: 354
<212> TYPE: DNA
<213> ORGANISM: Artificial Sequence
<220> FEATURE:
<223> OTHER INFORMATION: Synthetic Sequence

<400> SEQUENCE: 2

```
cagcaggtcc agctggtgca gtctggagca gaggtgaaaa agccggggga gtctctgaag    60
atctcctgta agggttctgg atacagcttt accagctact ggatcggctg ggtgcgccag   120
atgcccggga aaggcctgga gtggatgggg atcatctatc ctggtgactc tgataccaga   180
tacagcccgt ccttccaagg ccaggtcacc atctcagccg acaagtccat cagcaccgcc   240
tacctgcagt ggagcagcct gaaggcctcg gacaccgcca tgtattactg tgcgagactg   300
gttcatcgtt accgcgcaat ctggggccaa gggacaatgg tcaccgtctc ttcg         354
```

<210> SEQ ID NO 3
<211> LENGTH: 354
<212> TYPE: DNA
<213> ORGANISM: Artificial Sequence
<220> FEATURE:
<223> OTHER INFORMATION: Synthetic Sequence

<400> SEQUENCE: 3

```
cagcaggtcc agctggtgca gtctggagca gaggtgaaaa agccggggga gtctctgaag    60
atctcctgta agggttctgg atacagcttt accagctact ggatcggctg ggtgcgccag   120
atgcccggga aaggcctgga gtggatgggg atcatctatc ctggtgactc tgataccaga   180
tacagcccgt ccttccaagg ccaggtcacc atctcagccg acaagtccat cagcaccgcc   240
tacctgcagt ggagcagcct gaaggcctcg gacaccgcca tgtattactg tgcgagaccg   300
tatgctactg acaccagaat ctggggccaa gggacaatgg tcaccgtctc ttcg         354
```

<210> SEQ ID NO 4
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 4

Gln Gln Val Gln Leu Val Gln Ser Gly Ala Glu Val Lys Lys Pro Gly

```
                1               5                  10                  15
            Glu Ser Leu Lys Ile Ser Cys Lys Gly Ser Gly Tyr Ser Phe Thr Ser
                            20                  25                  30

Tyr Trp Ile Gly Trp Val Arg Gln Met Pro Gly Lys Gly Leu Glu Trp
                        35                  40                  45

Met Gly Ile Ile Tyr Pro Gly Asp Ser Asp Thr Arg Tyr Ser Pro Ser
                    50                  55                  60

Phe Gln Gly Gln Val Thr Ile Ser Ala Asp Lys Ser Ile Ser Thr Ala
             65                  70                  75                  80

Tyr Leu Gln Trp Ser Ser Leu Lys Ala Ser Asp Thr Ala Met Tyr Tyr
                            85                  90                  95

Cys Ala Arg Gln Gly Thr His Asn Arg Lys Ile Trp Gly Gln Gly Thr
                            100                 105                 110

Met Val Thr Val Ser Ser
                    115

<210> SEQ ID NO 5
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 5

Gln Gln Val Gln Leu Val Gln Ser Gly Ala Glu Val Lys Lys Pro Gly
             1               5                  10                  15

Glu Ser Leu Lys Ile Ser Cys Lys Gly Ser Gly Tyr Ser Phe Thr Ser
                            20                  25                  30

Tyr Trp Ile Gly Trp Val Arg Gln Met Pro Gly Lys Gly Leu Glu Trp
                        35                  40                  45

Met Gly Ile Ile Tyr Pro Gly Asp Ser Asp Thr Arg Tyr Ser Pro Ser
                    50                  55                  60

Phe Gln Gly Gln Val Thr Ile Ser Ala Asp Lys Ser Ile Ser Thr Ala
             65                  70                  75                  80

Tyr Leu Gln Trp Ser Ser Leu Lys Ala Ser Asp Thr Ala Met Tyr Tyr
                            85                  90                  95

Cys Ala Arg Leu Val His Arg Tyr Arg Ala Ile Trp Gly Gln Gly Thr
                            100                 105                 110

Met Val Thr Val Ser Ser
                    115

<210> SEQ ID NO 6
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 6

Gln Gln Val Gln Leu Val Gln Ser Gly Ala Glu Val Lys Lys Pro Gly
             1               5                  10                  15

Glu Ser Leu Lys Ile Ser Cys Lys Gly Ser Gly Tyr Ser Phe Thr Ser
                            20                  25                  30

Tyr Trp Ile Gly Trp Val Arg Gln Met Pro Gly Lys Gly Leu Glu Trp
                        35                  40                  45

Met Gly Ile Ile Tyr Pro Gly Asp Ser Asp Thr Arg Tyr Ser Pro Ser
                    50                  55                  60
```

Phe Gln Gly Gln Val Thr Ile Ser Ala Asp Lys Ser Ile Ser Thr Ala
 65                  70                  75                  80

Tyr Leu Gln Trp Ser Ser Leu Lys Ala Ser Asp Thr Ala Met Tyr Tyr
                 85                  90                  95

Cys Ala Arg Pro Tyr Ala Thr Asp Thr Arg Ile Trp Gly Gln Gly Thr
            100                 105                 110

Met Val Thr Val Ser Ser
            115

<210> SEQ ID NO 7
<211> LENGTH: 333
<212> TYPE: DNA
<213> ORGANISM: Artificial Sequence
<220> FEATURE:
<223> OTHER INFORMATION: Synthetic Sequence

<400> SEQUENCE: 7
caggctgtgg tgactcagga gccctcactg actgtgtccc caggagggac agtcactctc    60
acctgtgctt ccagcactgg agcagtcacc agtggtaact atccaaactg gttccagcag   120
agacctggac agccacccag ggcactgatt tatagtacaa gcaacaaaca ctcctggacc   180
cctgcccggt tctcaggctc cctccttggg ggcaaagctg ccctgaccct ttcgggtgcg   240
cagcctgagg atgaggctga gtattactgc cggttgtctt atgatcttgc tcgtccggtg   300
ttcggcggag ggaccaagct gaccgtccta ggt                                333

<210> SEQ ID NO 8
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 8

Gln Ala Val Val Thr Gln Glu Pro Ser Leu Thr Val Ser Pro Gly Gly
  1               5                  10                  15

Thr Val Thr Leu Thr Cys Ala Ser Ser Thr Gly Ala Val Thr Ser Gly
             20                  25                  30

Asn Tyr Pro Asn Trp Phe Gln Gln Arg Pro Gly Gln Pro Pro Arg Ala
         35                  40                  45

Leu Ile Tyr Ser Thr Ser Asn Lys His Ser Trp Thr Pro Ala Arg Phe
     50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Arg Leu Ser Tyr Asp Leu
                 85                  90                  95

Ala Arg Pro Val Phe Gly Gly Gly Thr Lys Leu Thr Val Leu Gly
            100                 105                 110

<210> SEQ ID NO 9
<211> LENGTH: 735
<212> TYPE: DNA
<213> ORGANISM: Artificial Sequence
<220> FEATURE:
<223> OTHER INFORMATION: Synthetic Sequence

<400> SEQUENCE: 9
cagcaggtcc agctggtgca gtctggagca gaggtgaaaa agccggggga gtctctgaag    60
atctcctgta agggttctgg atacagcttt accagctact ggatcggctg ggtgcgccag   120

```
atgcccggga aaggcctgga gtggatgggg atcatctatc ctggtgactc tgataccaga      180
tacagcccgt ccttccaagg ccaggtcacc atctcagccg acaagtccat cagcaccgcc      240
tacctgcagt ggagcagcct gaaggcctcg acaccgcca tgtattactg tgcgagacag      300
ggtactcata accgcaaaat ctggggccaa gggacaatgg tcaccgtctc ttcggcccct      360
caggccaaat cctcaggatc aggctccgaa tccaaagtcg accaggctgt ggtgactcag      420
gagccctcac tgactgtgtc cccaggaggg acagtcactc tcacctgtgc ttccagcact      480
ggagcagtca ccagtggtaa ctatccaaac tggttccagc agagacctgg acagccaccc      540
agggcactga tttatagtac aagcaacaaa cactcctgga cccctgcccg gttctcaggc      600
tccctccttg ggggcaaagc tgccctgacc ctttcgggtg cgcagcctga ggatgaggct      660
gagtattact gccggttgtc ttatgatctt gctcgtccgg tgttcggcgg agggaccaag      720
ctgaccgtcc taggt                                                      735
```

<210> SEQ ID NO 10
<211> LENGTH: 245
<212> TYPE: PRT
<213> ORGANISM: Artificial Sequence
<220> FEATURE:
<223> OTHER INFORMATION: Synthetic Sequence

<400> SEQUENCE: 10

```
Gln Gln Val Gln Leu Val Gln Ser Gly Ala Glu Val Lys Lys Pro Gly
  1               5                  10                  15

Glu Ser Leu Lys Ile Ser Cys Lys Gly Ser Gly Tyr Ser Phe Thr Ser
                 20                  25                  30

Tyr Trp Ile Gly Trp Val Arg Gln Met Pro Gly Lys Gly Leu Glu Trp
             35                  40                  45

Met Gly Ile Ile Tyr Pro Gly Asp Ser Asp Thr Arg Tyr Ser Pro Ser
         50                  55                  60

Phe Gln Gly Gln Val Thr Ile Ser Ala Asp Lys Ser Ile Ser Thr Ala
 65                  70                  75                  80

Tyr Leu Gln Trp Ser Ser Leu Lys Ala Ser Asp Thr Ala Met Tyr Tyr
                 85                  90                  95

Cys Ala Arg Gln Gly Thr His Asn Arg Lys Ile Trp Gly Gln Gly Thr
            100                 105                 110

Met Val Thr Val Ser Ser Ala Pro Gln Ala Lys Ser Ser Gly Ser Gly
            115                 120                 125

Ser Glu Ser Lys Val Asp Gln Ala Val Val Thr Gln Glu Pro Ser Leu
        130                 135                 140

Thr Val Ser Pro Gly Gly Thr Val Thr Leu Thr Cys Ala Ser Ser Thr
145                 150                 155                 160

Gly Ala Val Thr Ser Gly Asn Tyr Pro Asn Trp Phe Gln Gln Arg Pro
                165                 170                 175

Gly Gln Pro Pro Arg Ala Leu Ile Tyr Ser Thr Ser Asn Lys His Ser
            180                 185                 190

Trp Thr Pro Ala Arg Phe Ser Gly Ser Leu Leu Gly Gly Lys Ala Ala
        195                 200                 205

Leu Thr Leu Ser Gly Ala Gln Pro Glu Asp Glu Ala Glu Tyr Tyr Cys
    210                 215                 220

Arg Leu Ser Tyr Asp Leu Ala Arg Pro Val Phe Gly Gly Gly Thr Lys
225                 230                 235                 240

Leu Thr Val Leu Gly
            245
```

<210> SEQ ID NO 11
<211> LENGTH: 735
<212> TYPE: DNA
<213> ORGANISM: Artificial Sequence
<220> FEATURE:
<223> OTHER INFORMATION: Synthetic Sequence

<400> SEQUENCE: 11

```
cagcaggtcc agctggtgca gtctggagca gaggtgaaaa agccggggga gtctctgaag      60
atctcctgta agggttctgg atacagcttt accagctact ggatcggctg ggtgcgccag     120
atgcccggga aaggcctgga gtggatgggg atcatctatc ctggtgactc tgataccaga     180
tacagcccgt ccttccaagg ccaggtcacc atctcagccg acaagtccat cagcaccgcc     240
tacctgcagt ggagcagcct gaaggcctcg acaccgcca tgtattactg tgcgagactg      300
gttcatcgtt accgcgcaat ctggggccaa gggacaatgg tcaccgtctc ttcggcccct     360
caggccaaat cctcaggatc aggctccgaa tccaaagtcg accaggctgt ggtgactcag     420
gagccctcac tgactgtgtc cccaggaggg acagtcactc tcacctgtgc ttccagcact     480
ggagcagtca ccagtggtaa ctatccaaac tggttccagc agagacctgg acagccaccc     540
agggcactga tttatagtac aagcaacaaa cactcctgga cccctgcccg gttctcaggc     600
tccctccttg ggggcaaagc tgccctgacc ctttcgggtg cgcagcctga ggatgaggct     660
gagtattact gccggttgtc ttatgatctt gctcgtccgg tgttcggcgg agggaccaag     720
ctgaccgtcc taggt                                                       735
```

<210> SEQ ID NO 12
<211> LENGTH: 245
<212> TYPE: PRT
<213> ORGANISM: Artificial Sequence
<220> FEATURE:
<223> OTHER INFORMATION: Synthetic Sequence

<400> SEQUENCE: 12

```
Gln Gln Val Gln Leu Val Gln Ser Gly Ala Glu Val Lys Lys Pro Gly
  1               5                  10                  15

Glu Ser Leu Lys Ile Ser Cys Lys Gly Ser Gly Tyr Ser Phe Thr Ser
             20                  25                  30

Tyr Trp Ile Gly Trp Val Arg Gln Met Pro Gly Lys Gly Leu Glu Trp
         35                  40                  45

Met Gly Ile Ile Tyr Pro Gly Asp Ser Asp Thr Arg Tyr Ser Pro Ser
     50                  55                  60

Phe Gln Gly Gln Val Thr Ile Ser Ala Asp Lys Ser Ile Ser Thr Ala
 65                  70                  75                  80

Tyr Leu Gln Trp Ser Ser Leu Lys Ala Ser Asp Thr Ala Met Tyr Tyr
                 85                  90                  95

Cys Ala Arg Leu Val His Arg Tyr Arg Ala Ile Trp Gly Gln Gly Thr
            100                 105                 110

Met Val Thr Val Ser Ser Ala Pro Gln Ala Lys Ser Ser Gly Ser Gly
        115                 120                 125

Ser Glu Ser Lys Val Asp Gln Ala Val Val Thr Gln Glu Pro Ser Leu
    130                 135                 140

Thr Val Ser Pro Gly Gly Thr Val Thr Leu Thr Cys Ala Ser Ser Thr
145                 150                 155                 160

Gly Ala Val Thr Ser Gly Asn Tyr Pro Asn Trp Phe Gln Gln Arg Pro
                165                 170                 175
```

Gly Gln Pro Pro Arg Ala Leu Ile Tyr Ser Thr Ser Asn Lys His Ser
            180                 185                 190

Trp Thr Pro Ala Arg Phe Ser Gly Ser Leu Leu Gly Gly Lys Ala Ala
        195                 200                 205

Leu Thr Leu Ser Gly Ala Gln Pro Glu Asp Glu Ala Glu Tyr Tyr Cys
    210                 215                 220

Arg Leu Ser Tyr Asp Leu Ala Arg Pro Val Phe Gly Gly Gly Thr Lys
225                 230                 235                 240

Leu Thr Val Leu Gly
            245

<210> SEQ ID NO 13
<211> LENGTH: 735
<212> TYPE: DNA
<213> ORGANISM: Artificial Sequence
<220> FEATURE:
<223> OTHER INFORMATION: Synthetic Sequence

<400> SEQUENCE: 13

```
cagcaggtcc agctggtgca gtctggagca gaggtgaaaa agccggggga gtctctgaag      60
atctcctgta aggggttctgg atacagcttt accagctact ggatcggctg ggtgcgccag     120
atgcccggga aaggcctgga gtggatgggg atcatctatc ctggtgactc tgataccaga     180
tacagcccgt ccttccaagg ccaggtcacc atctcagccg acaagtccat cagcaccgcc     240
tacctgcagt ggagcagcct gaaggcctcg gacaccgcca tgtattactg cgagaccg      300
tatgctactg acaccagaat ctggggccaa gggacaatgg tcaccgtctc ttcggcccct     360
caggccaaat cctcaggatc aggctccgaa tccaaagtcg accaggctgt ggtgactcag     420
gagccctcac tgactgtgtc cccaggaggg acagtcactc tcacctgtgc ttccagcact     480
ggagcagtca ccagtggtaa ctatccaaac tggttccagc agagacctgg acagccaccc     540
agggcactga tttatagtac aagcaacaaa cactcctgga cccctgcccg gttctcaggc     600
tccctccttg ggggcaaagc tgccctgacc ctttcgggtg cgcagcctga ggatgaggct     660
gagtattact gccggttgtc ttatgatctt gctcgtccgg tgttcggcgg agggaccaag     720
ctgaccgtcc taggt                                                      735
```

<210> SEQ ID NO 14
<211> LENGTH: 245
<212> TYPE: PRT
<213> ORGANISM: Artificial Sequence
<220> FEATURE:
<223> OTHER INFORMATION: Synthetic Sequence

<400> SEQUENCE: 14

Gln Gln Val Gln Leu Val Gln Ser Gly Ala Glu Val Lys Lys Pro Gly
1               5                   10                  15

Glu Ser Leu Lys Ile Ser Cys Lys Gly Ser Gly Tyr Ser Phe Thr Ser
            20                  25                  30

Tyr Trp Ile Gly Trp Val Arg Gln Met Pro Gly Lys Gly Leu Glu Trp
        35                  40                  45

Met Gly Ile Ile Tyr Pro Gly Asp Ser Asp Thr Arg Tyr Ser Pro Ser
    50                  55                  60

Phe Gln Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
            85                  90                  95

```
Cys Ala Arg Pro Tyr Ala Thr Asp Thr Arg Ile Trp Gly Gln Gly Thr
                100                 105                 110
Met Val Thr Val Ser Ser Ala Pro Gln Ala Lys Ser Ser Gly Ser Gly
                115                 120                 125
Ser Glu Ser Lys Val Asp Gln Ala Val Val Thr Gln Glu Pro Ser Leu
            130                 135                 140
Thr Val Ser Pro Gly Gly Thr Val Thr Leu Thr Cys Ala Ser Ser Thr
145                 150                 155                 160
Gly Ala Val Thr Ser Gly Asn Tyr Pro Asn Trp Phe Gln Gln Arg Pro
                165                 170                 175
Gly Gln Pro Pro Arg Ala Leu Ile Tyr Ser Thr Ser Asn Lys His Ser
                180                 185                 190
Trp Thr Pro Ala Arg Phe Ser Gly Ser Leu Leu Gly Gly Lys Ala Ala
                195                 200                 205
Leu Thr Leu Ser Gly Ala Gln Pro Glu Asp Glu Ala Glu Tyr Tyr Cys
        210                 215                 220
Arg Leu Ser Tyr Asp Leu Ala Arg Pro Val Phe Gly Gly Gly Thr Lys
225                 230                 235                 240
Leu Thr Val Leu Gly
                245
```

<210> SEQ ID NO 15
<211> LENGTH: 648
<212> TYPE: DNA
<213> ORGANISM: Artificial Sequence
<220> FEATURE:
<223> OTHER INFORMATION: Synthetic Sequence

<400> SEQUENCE: 15

```
caggctgtgg tgactcagga gccctcactg actgtgtccc caggagggac agtcactctc    60
acctgtgctt ccagcactgg agcagtcacc agtggtaact atccaaactg gttccagcag   120
agacctggac agccacccag gcactgatt tatagtacaa gcaacaaaca ctcctggacc   180
cctgcccggt tctcaggctc cctccttggg ggcaaagctg ccctgaccct ttcgggtgcg   240
cagcctgagg atgaggctga gtattactgc cggttgtctt atgatcttgc tcgtccggtg   300
ttcggcggag ggaccaagct gaccgtccta ggtcagccca aggctgcccc ctcggtcact   360
ctgttcccac cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac acctccaaa caaagcaaca caagtacgc ggccagcagc   540
tacctgagcc tgacgcctga gcagtggaag tcccacaaaa gctacagctg ccaggtcacg   600
catgaaggga gcaccgtgga gaagacagtg gcccctacag aatgttca                648
```

<210> SEQ ID NO 16
<211> LENGTH: 663
<212> TYPE: DNA
<213> ORGANISM: Artificial Sequence
<220> FEATURE:
<223> OTHER INFORMATION: Synthetic Sequence

<400> SEQUENCE: 16

```
cagcaggtcc agctggtgca gtctggagca gaggtgaaaa agccggggga gtctctgaag    60
atctcctgta agggttctgg atacagcttt accagctact ggatcggctg ggtgcgccag   120
atgcccggga aaggcctgga gtggatgggg atcatctatc tggtgactc tgataccaga   180
```

```
tacagcccgt ccttccaagg ccaggtcact atctcagccg acaagtccat cagcaccgcc    240
tacctgcagt ggagcagcct gaaggcctcg gacaccgcca tgtattactg tgcgagacag    300
ggtactcata accgcaaaat ctggggccaa gggacaatgg tcaccgtctc aagcgcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtccacacc ttcccggctg tcctacagtc ctcaggactc    540
tactccctca gcagcgtagt gaccgtgccc tccagcagct gggcaccca gacctacatc    600 tgcaacgtga atcacaagcc cagcaacacc aaggtggaca agaaagttga gcccaaatct    660
tgt                                                                 663
```

<210> SEQ ID NO 17
<211> LENGTH: 216
<212> TYPE: PRT
<213> ORGANISM: Artificial Sequence
<220> FEATURE:
<223> OTHER INFORMATION: Synthetic Sequence

<400> SEQUENCE: 17

```
Gln Ala Val Val Thr Gln Glu Pro Ser Leu Thr Val Ser Pro Gly Gly
  1               5                  10                  15

Thr Val Thr Leu Thr Cys Ala Ser Ser Thr Gly Ala Val Thr Ser Gly
             20                  25                  30

Asn Tyr Pro Asn Trp Phe Gln Gln Arg Pro Gly Gln Pro Pro Arg Ala
         35                  40                  45

Leu Ile Tyr Ser Thr Ser Asn Lys His Ser Trp Thr Pro Ala Arg Phe
     50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Arg Leu Ser Tyr Asp Leu
                 85                  90                  95

Ala Arg Pro Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 18
<211> LENGTH: 221
<212> TYPE: PRT
<213> ORGANISM: Artificial Sequence
<220> FEATURE:
<223> OTHER INFORMATION: Synthetic Sequence

<400> SEQUENCE: 18

Gln Gln Val Gln Leu Val Gln Ser Gly Ala Glu Val Lys Lys Pro Gly
 1               5                  10                  15

Glu Ser Leu Lys Ile Ser Cys Lys Gly Ser Gly Tyr Ser Phe Thr Ser
            20                  25                  30

Tyr Trp Ile Gly Trp Val Arg Gln Met Pro Gly Lys Gly Leu Glu Trp
        35                  40                  45

Met Gly Ile Ile Tyr Pro Gly Asp Ser Asp Thr Arg Tyr Ser Pro Ser
    50                  55                  60

Phe Gln Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
                85                  90                  95

Cys Ala Arg Gln Gly Thr His Asn Arg Lys Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 19
<211> LENGTH: 648
<212> TYPE: DNA
<213> ORGANISM: Artificial Sequence
<220> FEATURE:
<223> OTHER INFORMATION: Synthetic Sequence

<400> SEQUENCE: 19
caggctgtgg tgactcagga gccctcactg actgtgtccc caggagggac agtcactctc        60
acctgtgctt ccagcactgg agcagtcacc agtggtaact atccaaactg gttccagcag       120
agacctggac agccacccag ggcactgatt tatagtacaa gcaacaaaca ctcctggacc       180
cctgcccggt tctcaggctc cctccttggg ggcaaagctg ccctgaccct tcgggtgcg       240 cagcctgagg atgaggctga gtattactgc cggttgtctt atgatcttgc tcgtccggtg       300
ttcggcggag ggaccaagct gaccgtccta ggtcagccca aggctgcccc ctcggtcact       360
ctgttcccac cctcctctga ggagcttcaa gccaacaagg ccacactggt gtgtctcata       420
agtgacttct acccgggagc cgtgacagtg gcctggaagg cagatagcag ccccgtcaag       480
gcgggagtgg agaccaccac acccctccaaa caaagcaaca caagtacgc ggccagcagc       540 tacctgagcc tgacgcctga gcagtggaag tcccacaaaa gctacagctg ccaggtcacg       600
catgaaggga gcaccgtgga agacagtg gcccctacag aatgttca       648

<210> SEQ ID NO 20
<211> LENGTH: 663
<212> TYPE: DNA

<213> ORGANISM: Artificial Sequence
<220> FEATURE:
<223> OTHER INFORMATION: Synthetic Sequence

<400> SEQUENCE: 20

```
cagcaggtcc agctggtgca gtctggagca gaggtgaaaa agccggggga gtctctgaag     60
atctcctgta agggttctgg atacagcttt accagctact ggatcggctg ggtgcgccag    120
atgcccggga aaggcctgga gtggatgggg atcatctatc ctggtgactc tgataccaga    180
tacagcccgt ccttccaagg ccaggtcacc atctcagccg acaagtccat cagcaccgcc    240
tacctgcagt ggagcagcct gaaggcctcg gacaccgcca tgtattactg tgcgagactg    300
gttcatcgtt accgcgcaat ctggggccaa gggacaatgg tcaccgtctc aagcgcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtccacacc ttcccggctg tcctacagtc ctcaggactc    540
tactccctca gcagcgtagt gaccgtgccc tccagcagct tgggcaccca gacctacatc    600
tgcaacgtga atcacaagcc cagcaacacc aaggtggaca agaaagttga gcccaaatct    660
tgt                                                                  663
```

<210> SEQ ID NO 21
<211> LENGTH: 216
<212> TYPE: PRT
<213> ORGANISM: Artificial Sequence
<220> FEATURE:
<223> OTHER INFORMATION: Synthetic Sequence

<400> SEQUENCE: 21

```
Gln Ala Val Val Thr Gln Glu Pro Ser Leu Thr Val Ser Pro Gly Gly
  1               5                  10                  15

Thr Val Thr Leu Thr Cys Ala Ser Ser Thr Gly Ala Val Thr Ser Gly
             20                  25                  30

Asn Tyr Pro Asn Trp Phe Gln Gln Arg Pro Gly Gln Pro Pro Arg Ala
         35                  40                  45

Leu Ile Tyr Ser Thr Ser Asn Lys His Ser Trp Thr Pro Ala Arg Phe
     50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Arg Leu Ser Tyr Asp Leu
                 85                  90                  95

Ala Arg Pro Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205
```

```
Thr Val Ala Pro Thr Glu Cys Ser
    210                 215

<210> SEQ ID NO 22
<211> LENGTH: 221
<212> TYPE: PRT
<213> ORGANISM: Artificial Sequence
<220> FEATURE:
<223> OTHER INFORMATION: Synthetic Sequence

<400> SEQUENCE: 22

Gln Gln Val Gln Leu Val Gln Ser Gly Ala Glu Val Lys Lys Pro Gly
  1               5                  10                  15

Glu Ser Leu Lys Ile Ser Cys Lys Gly Ser Gly Tyr Ser Phe Thr Ser
                 20                  25                  30

Tyr Trp Ile Gly Trp Val Arg Gln Met Pro Gly Lys Gly Leu Glu Trp
             35                  40                  45

Met Gly Ile Ile Tyr Pro Gly Asp Ser Asp Thr Arg Tyr Ser Pro Ser
 50                  55                  60

Phe Gln Gly Gln Val Thr Ile Ser Ala Asp Lys Ser Ile Ser Thr Ala
 65                  70                  75                  80

Tyr Leu Gln Trp Ser Ser Leu Lys Ala Ser Asp Thr Ala Met Tyr Tyr
                 85                  90                  95

Cys Ala Arg Leu Val His Arg Tyr Arg Ala Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 23
<211> LENGTH: 648
<212> TYPE: DNA
<213> ORGANISM: Artificial Sequence
<220> FEATURE:
<223> OTHER INFORMATION: Synthetic Sequence

<400> SEQUENCE: 23
caggctgtgg tgactcagga gccctcactg actgtgtccc caggagggac agtcactctc        60
acctgtgctt ccagcactgg agcagtcacc agtggtaact atccaaactg gttccagcag       120
agacctggac agccacccag ggcactgatt tatagtacaa gcaacaaaca ctcctggacc       180
cctgcccggt tctcaggctc cctccttggg ggcaaagctg ccctgaccct ttcgggtgcg       240
cagcctgagg atgaggctga gtattactgc cggttgtctt atgatcttgc tcgtccggtg       300
ttcggcggag ggaccaagct gaccgtccta ggtcagccca aggctgcccc ctcggtcact       360
ctgttcccac cctcctctga ggagcttcaa gccaacaagg ccacactggt gtgtctcata       420
```

```
agtgacttct acccgggagc cgtgacagtg gcctggaagg cagatagcag ccccgtcaag    480
gcgggagtgg agaccaccac accctccaaa caaagcaaca acaagtacgc ggccagcagc    540
tacctgagcc tgacgcctga gcagtggaag tcccacaaaa gctacagctg ccaggtcacg    600
catgaaggga gcaccgtgga gaagacagtg gcccctacag aatgttca                 648
```

<210> SEQ ID NO 24
<211> LENGTH: 663
<212> TYPE: DNA
<213> ORGANISM: Artificial Sequence
<220> FEATURE:
<223> OTHER INFORMATION: Synthetic Sequence

<400> SEQUENCE: 24

```
cagcaggtcc agctggtgca gtctggagca gaggtgaaaa agccggggga gtctctgaag    60
atctcctgta agggttctgg atacagcttt accagctact ggatcggctg ggtgcgccag    120
atgcccggga aggcctggag gtggatgggg atcatctatc ctggtgactc tgataccaga    180
tacagcccgt ccttccaagg ccaggtcacc atctcagccg acaagtccat cagcaccgcc    240
tacctgcagt ggagcagcct gaaggcctcg gacaccgcca tgtattactg tgcgagaccg    300
tatgctactg acaccagaat ctggggccaa gggacaatgg tcaccgtctc aagcgcctcc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtccacacc ttcccggctg tcctacagtc ctcaggactc    540
tactccctca gcagcgtagt gaccgtgccc tccagcagct tgggcaccca gacctacatc    600
tgcaacgtga atcacaagcc cagcaacacc aaggtggaca agaaagttga gcccaaatct    660
tgt                                                                  663
```

<210> SEQ ID NO 25
<211> LENGTH: 216
<212> TYPE: PRT
<213> ORGANISM: Artificial Sequence
<220> FEATURE:
<223> OTHER INFORMATION: Synthetic Sequence

<400> SEQUENCE: 25

```
Gln Ala Val Val Thr Gln Glu Pro Ser Leu Thr Val Ser Pro Gly Gly
  1               5                  10                  15

Thr Val Thr Leu Thr Cys Ala Ser Ser Thr Gly Ala Val Thr Ser Gly
                 20                  25                  30

Asn Tyr Pro Asn Trp Phe Gln Gln Arg Pro Gly Gln Pro Pro Arg Ala
             35                  40                  45

Leu Ile Tyr Ser Thr Ser Asn Lys His Ser Trp Thr Pro Ala Arg Phe
         50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Arg Leu Ser Tyr Asp Leu
                 85                  90                  95

Ala Arg Pro Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140
```

```
Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 26
<211> LENGTH: 221
<212> TYPE: PRT
<213> ORGANISM: Artificial Sequence
<220> FEATURE:
<223> OTHER INFORMATION: Synthetic Sequence

<400> SEQUENCE: 26

```
Gln Gln Val Gln Leu Val Gln Ser Gly Ala Glu Val Lys Lys Pro Gly
  1               5                  10                  15

Glu Ser Leu Lys Ile Ser Cys Lys Gly Ser Gly Tyr Ser Phe Thr Ser
             20                  25                  30

Tyr Trp Ile Gly Trp Val Arg Gln Met Pro Gly Lys Gly Leu Glu Trp
         35                  40                  45

Met Gly Ile Ile Tyr Pro Gly Asp Ser Asp Thr Arg Tyr Ser Pro Ser
     50                  55                  60

Phe Gln Gly Gln Val Thr Ile Ser Ala Asp Lys Ser Ile Ser Thr Ala
 65                  70                  75                  80

Tyr Leu Gln Trp Ser Ser Leu Lys Ala Ser Asp Thr Ala Met Tyr Tyr
                 85                  90                  95

Cys Ala Arg Pro Tyr Ala Thr Asp Thr Arg Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
210                 215                 220
```

<210> SEQ ID NO 27
<211> LENGTH: 1467
<212> TYPE: DNA
<213> ORGANISM: Artificial Sequence
<220> FEATURE:
<223> OTHER INFORMATION: Synthetic Sequence

<400> SEQUENCE: 27
caggtccagc tggtgcagtc tggagcagag gtgaaaaagc cggggagtc tctgaagatc    60

```
tcctgtaagg gttctggata cagctttacc agctactgga tcggctgggt gcgccagatg      120
cccgggaaag gcctggagtg gatggggatc atctatcctg gtgactctga taccagatac      180
agcccgtcct tccaaggcca ggtcaccatc tcagccgaca gtccatcagc accgcctac       240 ctgcagtgga gcagcctgaa ggcctcggac accgccatgt attactgtgc gagacagggt      300
actcataacc gcaaaatctg gggccaaggg acaatggtca ccgtctcttc ggcccctcag      360
gccaaatcct caggatcagg ctccgaatcc aaagtcgacc aggctgtggt gactcaggag      420
ccctcactga ctgtgtcccc aggagggaca gtcactctca cctgtgcttc cagcactgga      480
gcagtcacca gtggtaacta tccaaactgg ttccagcaga acctggaca gccacccagg       540 gcactgattt atagtacaag caacaaacac tcctggaccc ctgcccggtt ctcaggctcc      600
ctccttgggg gcaaagctgc cctgacccct tcgggtgcgc agcctgagga tgaggctgag      660
tattactgcc ggttgtctta tgatcttgct cgtccggtgt tcggcggagg gaccaagctg      720
accgtcctag gttctagagg cggaggtgga tcgggcggag gtggatcggc agagcccaaa      780
tcttgtgaca aaactcacac atgcccaccg tgcccagcac ctgaactcct ggggggaccg      840
tcagtcttcc tcttcccccc aaaacccaag gacaccctca tgatctcccg gacccctgag      900
gtcacatgcg tggtggtgga cgtgagccac gaagaccctg aggtcaagtt caactggtac      960
gtggacggcg tgaaggtgca taatgccaag acaaagccgc gggaggagca gtacaacagc      1020
acgtaccgtg tggtcagcgt cctcaccgtc ctgcaccagg actggctgaa tggcaaggag      1080
tacaagtgca aggtctccaa caaagccctc ccagccccca tcgagaaaac catctccaaa      1140
gccaaagggc agccccgaga accacaggtg tacaccctgc ccccatcccg ggatgagctg      1200
accaagaacc aggtcagcct gacctgcctg gtcaaaggct tctatcccag cgacatcgcc      1260
gtggagtggg agagcaatgg gcagccggag aacaactaca agaccacgcc tcccgtgctg      1320
gactccgacg gctccttctt cctctacagc aagctcaccg tggacaagag caggtggcag      1380
caggggaacg tcttctcatg ctccgtgatg catgaggctc tgcacaacca ctacacgcag      1440
aagagcctct ccctgtctcc gggtaaa                                          1467
```

<210> SEQ ID NO 28
<211> LENGTH: 489
<212> TYPE: PRT
<213> ORGANISM: Artificial Sequence
<220> FEATURE:
<223> OTHER INFORMATION: Synthetic Sequence

<400> SEQUENCE: 28

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Thr His Asn Arg Lys Ile Trp Gly Gln Gly Thr Met
            100                 105                 110
```

Val Thr Val Ser Ser Ala Pro Gln Ala Lys Ser Ser Gly Ser Gly Ser
            115                 120                 125

Glu Ser Lys Val Asp Gln Ala Val Val Thr Gln Glu Pro Ser Leu Thr
130                 135                 140

Val Ser Pro Gly Gly Thr Val Thr Leu Thr Cys Ala Ser Ser Thr Gly
145                 150                 155                 160

Ala Val Thr Ser Gly Asn Tyr Pro Asn Trp Phe Gln Gln Arg Pro Gly
                165                 170                 175

Gln Pro Pro Arg Ala Leu Ile Tyr Ser Thr Ser Asn Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Glu Asp Glu Ala Glu Tyr Tyr Cys Arg
210                 215                 220

Leu Ser Tyr Asp Leu Ala Arg Pro Val Phe Gly Gly Thr Lys Leu
225                 230                 235                 240

Thr Val Leu Gly Ser Arg Gly Gly Gly Ser Gly Gly Gly Gly Ser
                245                 250                 255

Ala Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Lys Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 29
<211> LENGTH: 1467
<212> TYPE: DNA
<213> ORGANISM: Artificial Sequence
<220> FEATURE:
<223> OTHER INFORMATION: Synthetic Sequence

<400> SEQUENCE: 29

```
caggtccagc tggtgcagtc tggagcagag gtgaaaaagc cggggagtc tctgaagatc      60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac     240
ctgcagtgga gcagcctgaa ggcctcggac accgccatgt attactgtgc gagactggtt    300
catcgttacc gcgcaatctg gggccaaggg acaatggtca ccgtctcttc ggcccctcag    360
gccaaatcct caggatcagg ctccgaatcc aaagtcgacc aggctgtggt gactcaggag    420
ccctcactga ctgtgtcccc aggagggaca gtcactctca cctgtgcttc agcactgga    480
gcagtcacca gtggtaacta tccaaactgg ttccagcaga gacctggaca gccacccagg    540
gcactgattt atagtacaag caacaaacac tcctggaccc ctgcccggtt ctcaggctcc    600
ctccttgggg gcaaagctgc cctgacccct tcgggtgcgc agcctgagga tgaggctgag    660
tattactgcc ggttgtctta tgatcttgct cgtccggtgt tcggcggagg gaccaagctg    720
accgtcctag gttctagagg cggaggtgga tcgggcggag gtggatcggc agagcccaaa    780
tcttgtgaca aaactcacac atgcccaccg tgcccagcac ctgaactcct ggggggaccg    840
tcagtcttcc tcttcccccc aaaacccaag gacaccctca tgatctcccg gacccctgag    900
gtcacatgcg tggtggtgga cgtgagccac gaagaccctg aggtcaagtt caactggtac    960
gtggacggcg tgaaggtgca taatgccaag acaaagccgc gggaggagca gtacaacagc   1020
acgtaccgtg tggtcagcgt cctcaccgtc ctgcaccagg actggctgaa tggcaaggag   1080
tacaagtgca aggtctccaa caaagccctc ccagccccca tcgagaaaac catctccaaa   1140
gccaaaggc agccccgaga accacaggtg tacaccctgc ccccatcccg ggatgagctg   1200
accaagaacc aggtcagcct gacctgcctg gtcaaaggct tctatcccag cgacatcgcc   1260
gtggagtggg agagcaatgg gcagccggag aacaactaca agaccacgcc tcccgtgctg   1320
gactccgacg gctccttctt cctctacagc aagctcaccg tggacaagag caggtggcag   1380
caggggaacg tcttctcatg ctccgtgatg catgaggctc tgcacaacca ctacacgcag   1440
aagagcctct ccctgtctcc gggtaaa                                       1467
```

<210> SEQ ID NO 30
<211> LENGTH: 489
<212> TYPE: PRT
<213> ORGANISM: Artificial Sequence
<220> FEATURE:
<223> OTHER INFORMATION: Synthetic Sequence

<400> SEQUENCE: 30

```
Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
```

```
                        85                  90                  95
Ala Arg Leu Val His Arg Tyr Arg Ala Ile Trp Gly Gln Gly Thr Met
            100                 105                 110
Val Thr Val Ser Ser Ala Pro Gln Ala Lys Ser Ser Gly Ser Gly Ser
            115                 120                 125
Glu Ser Lys Val Asp Gln Ala Val Val Thr Gln Glu Pro Ser Leu Thr
            130                 135                 140
Val Ser Pro Gly Gly Thr Val Thr Leu Thr Cys Ala Ser Ser Thr Gly
145                 150                 155                 160
Ala Val Thr Ser Gly Asn Tyr Pro Asn Trp Phe Gln Gln Arg Pro Gly
                165                 170                 175
Gln Pro Pro Arg Ala Leu Ile Tyr Ser Thr Asn Lys His Ser Trp
            180                 185                 190
Thr Pro Ala Arg Phe Ser Gly Ser Leu Leu Gly Gly Lys Ala Ala Leu
            195                 200                 205
Thr Leu Ser Gly Ala Gln Pro Glu Asp Glu Ala Glu Tyr Tyr Cys Arg
            210                 215                 220
Leu Ser Tyr Asp Leu Ala Arg Pro Val Phe Gly Gly Gly Thr Lys Leu
225                 230                 235                 240
Thr Val Leu Gly Ser Arg Gly Gly Gly Ser Gly Gly Gly Gly Ser
                245                 250                 255
Ala Glu Pro Lys Ser Cys Asp Lys Thr His Thr Cys Pro Pro Cys Pro
            260                 265                 270
Ala Pro Glu Leu Leu Gly Gly Pro Ser Val Phe Leu Phe Pro Pro Lys
            275                 280                 285
Pro Lys Asp Thr Leu Met Ile Ser Arg Thr Pro Glu Val Thr Cys Val
            290                 295                 300
Val Val Asp Val Ser His Glu Asp Pro Glu Val Lys Phe Asn Trp Tyr
305                 310                 315                 320
Val Asp Gly Val Lys Val His Asn Ala Lys Thr Lys Pro Arg Glu Glu
                325                 330                 335
Gln Tyr Asn Ser Thr Tyr Arg Val Val Ser Val Leu Thr Val Leu His
            340                 345                 350
Gln Asp Trp Leu Asn Gly Lys Glu Tyr Lys Cys Lys Val Ser Asn Lys
            355                 360                 365
Ala Leu Pro Ala Pro Ile Glu Lys Thr Ile Ser Lys Ala Lys Gly Gln
            370                 375                 380
Pro Arg Glu Pro Gln Val Tyr Thr Leu Pro Pro Ser Arg Asp Glu Leu
385                 390                 395                 400
Thr Lys Asn Gln Val Ser Leu Thr Cys Leu Val Lys Gly Phe Tyr Pro
                405                 410                 415
Ser Asp Ile Ala Val Glu Trp Glu Ser Asn Gly Gln Pro Glu Asn Asn
            420                 425                 430
Tyr Lys Thr Thr Pro Pro Val Leu Asp Ser Asp Gly Ser Phe Phe Leu
            435                 440                 445
Tyr Ser Lys Leu Thr Val Asp Lys Ser Arg Trp Gln Gln Gly Asn Val
            450                 455                 460
Phe Ser Cys Ser Val Met His Glu Ala Leu His Asn His Tyr Thr Gln
465                 470                 475                 480
Lys Ser Leu Ser Leu Ser Pro Gly Lys
                485

<210> SEQ ID NO 31
```

<211> LENGTH: 1467
<212> TYPE: DNA
<213> ORGANISM: Artificial Sequence
<220> FEATURE:
<223> OTHER INFORMATION: Synthetic Sequence

<400> SEQUENCE: 31

```
caggtccagc tggtgcagtc tggagcagag gtgaaaaagc cggggagtc tctgaagatc      60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac     240
ctgcagtgga gcagcctgaa ggcctcggac accgccatgt attactgtgc gagaccgtat    300
gctactgaca ccagaatctg gggccaaggg acaatggtca ccgtctcttc ggcccctcag    360
gccaaatcct caggatcagg ctccgaatcc aaagtcgacc aggctgtggt gactcaggag    420
ccctcactga ctgtgtcccc aggagggaca gtcactctca cctgtgcttc agcactgga    480
gcagtcacca gtggtaacta tccaaactgg ttccagcaga gacctggaca gccacccagg    540
gcactgattt atagtacaag caacaaacac tcctggaccc ctgcccggtt ctcaggctcc    600
ctccttgggg gcaaagctgc cctgacccct tcgggtgcgc agcctgagga tgaggctgag    660
tattactgcc ggttgtctta tgatcttgct cgtccggtgt tcggcggagg gaccaagctg    720
accgtcctag gttctagagg cggaggtgga tcgggcggag gtggatcggc agagcccaaa    780
tcttgtgaca aaactcacac atgcccaccg tgcccagcac ctgaactcct ggggggaccg    840
tcagtcttcc tcttcccccc aaaacccaag gacaccctca tgatctcccg gacccctgag    900
gtcacatgcg tggtggtgga cgtgagccac gaagaccctg aggtcaagtt caactggtac    960
gtggacggcg tgaaggtgca taatgccaag acaaagccgc gggaggagca gtacaacagc   1020
acgtaccgtg tggtcagcgt cctcaccgtc ctgcaccagg actggctgaa tggcaaggag   1080
tacaagtgca aggtctccaa caaagccctc ccagccccca tcgagaaaac catctccaaa   1140
gccaaagggc agccccgaga accacaggtg tacaccctgc ccccatcccg ggatgagctg   1200
accaagaacc aggtcagcct gacctgcctg gtcaaaggct tctatcccag cgacatcgcc   1260
gtggagtggg agagcaatgg gcagccggag aacaactaca agaccacgcc tcccgtgctg   1320
gactccgacg gctccttctt cctctacagc aagctcaccg tggacaagag caggtggcag   1380
caggggaacg tcttctcatg ctccgtgatg catgaggctc tgcacaacca ctacacgcag   1440
aagagcctct ccctgtctcc gggtaaa                                       1467
```

<210> SEQ ID NO 32
<211> LENGTH: 489
<212> TYPE: PRT
<213> ORGANISM: Artificial Sequence
<220> FEATURE:
<223> OTHER INFORMATION: Synthetic Sequence

<400> SEQUENCE: 32

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60
```

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Pro Tyr Ala Thr Asp Thr Arg Ile Trp Gly Gln Gly Thr Met
            100                 105                 110

Val Thr Val Ser Ser Ala Pro Gln Ala Lys Ser Ser Gly Ser Gly Ser
        115                 120                 125

Glu Ser Lys Val Asp Gln Ala Val Val Thr Gln Glu Pro Ser Leu Thr
130                 135                 140

Val Ser Pro Gly Gly Thr Val Thr Leu Thr Cys Ala Ser Ser Thr Gly
145                 150                 155                 160

Ala Val Thr Ser Gly Asn Tyr Pro Asn Trp Phe Gln Gln Arg Pro Gly
                165                 170                 175

Gln Pro Pro Arg Ala Leu Ile Tyr Ser Thr Ser Asn Lys His Ser Trp
            180                 185                 190

Thr Pro Ala Arg Phe Ser Gly Ser Leu Leu Gly Gly Lys Ala Ala Leu
        195                 200                 205

Thr Leu Ser Gly Ala Gln Pro Glu Asp Glu Ala Glu Tyr Tyr Cys Arg
210                 215                 220

Leu Ser Tyr Asp Leu Ala Arg Pro Val Phe Gly Gly Gly Thr Lys Leu
225                 230                 235                 240

Thr Val Leu Gly Ser Arg Gly Gly Gly Ser Gly Gly Gly Ser
                245                 250                 255

Ala Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Lys Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480
```

Lys Ser Leu Ser Leu Ser Pro Gly Lys
            485

<210> SEQ ID NO 33
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 33

Leu Val Val Arg Asp Thr Glu
 1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 34

Leu Leu Ser Tyr Ser Gly Ala Arg
 1               5

<210> SEQ ID NO 35
<211> LENGTH: 62
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (23)..(24)
<223> OTHER INFORMATION: n=T, C, A or G
<220> FEATURE:
<221> NAME/KEY: misc_feature
<222> LOCATION: (26)..(27)
<223> OTHER INFORMATION: n=T, C, A or G
<220> FEATURE:
<221> NAME/KEY: misc_feature
<222> LOCATION: (29)..(30)
<223> OTHER INFORMATION: n=T, C, A or G
<220> FEATURE:
<221> NAME/KEY: misc_feature
<222> LOCATION: (32)..(33)
<223> OTHER INFORMATION: n=T, C, A or G
<220> FEATURE:
<221> NAME/KEY: misc_feature
<222> LOCATION: (35)..(36)
<223> OTHER INFORMATION: n=T, C, A or G
<220> FEATURE:
<221> NAME/KEY: misc_feature
<222> LOCATION: (38)..(39)
<223> OTHER INFORMATION: n=T, C, A or G
<220> FEATURE:
<221> NAME/KEY: misc_feature
<222> LOCATION: (41)..(42)
<223> OTHER INFORMATION: n=T, C, A or G

<400> SEQUENCE: 35
cattgtccct tggccccaga ttnngnngnn annannannc nntctcgcac agtaatacat gg    62

<210> SEQ ID NO 36
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 36

```
gaccactcga gtgcacagca ggtccagctg                                          30
```

<210> SEQ ID NO 37
<211> LENGTH: 56
<212> TYPE: DNA
<213> ORGANISM: Artificial Sequence
<220> FEATURE:
<223> OTHER INFORMATION: Synthetic Sequence

<400> SEQUENCE: 37

```
caggtgcaca ggcctgaggg gccgaagaga cggtgaccat tgtcccttgg ccccag           56
```

<210> SEQ ID NO 38
<211> LENGTH: 65
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (22)..(23)
<223> OTHER INFORMATION: n=T, C, A or G
<220> FEATURE:
<221> NAME/KEY: misc_feature
<222> LOCATION: (25)..(26)
<223> OTHER INFORMATION: n=T, C, A or G
<220> FEATURE:
<221> NAME/KEY: misc_feature
<222> LOCATION: (28)..(29)
<223> OTHER INFORMATION: n=T, C, A or G
<220> FEATURE:
<221> NAME/KEY: misc_feature
<222> LOCATION: (31)..(32)
<223> OTHER INFORMATION: n=T, C, A or G
<220> FEATURE:
<221> NAME/KEY: misc_feature
<222> LOCATION: (34)..(35)
<223> OTHER INFORMATION: n=T, C, A or G
<220> FEATURE:
<221> NAME/KEY: misc_feature
<222> LOCATION: (37)..(38)
<223> OTHER INFORMATION: n=T, C, A or G
<220> FEATURE:
<221> NAME/KEY: misc_feature
<222> LOCATION: (40)..(41)
<223> OTHER INFORMATION: n=T, C, A or G
<220> FEATURE:
<221> NAME/KEY: misc_feature
<222> LOCATION: (43)..(44)
<223> OTHER INFORMATION: n=T, C, A or G

<400> SEQUENCE: 38

```
gtccctccgc cgaacaccgg annannanna nnannanncn ncnngcagta atactcagcc        60
tcatc                                                                    65
```

<210> SEQ ID NO 39
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 39

```
gaccactcga gtcgaccagg ctgtggtgac                                          30
```

<210> SEQ ID NO 40
<211> LENGTH: 55
<212> TYPE: DNA
<213> ORGANISM: Artificial Sequence
<220> FEATURE:
<223> OTHER INFORMATION: Synthetic Sequence

<400> SEQUENCE: 40
caggtgcaca gcggccgcac ctaggacggt cagcttggtc cctccgccga acacc       55

<210> SEQ ID NO 41
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 41

Gln Gly Thr His Asn Arg Lys
 1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 42

Leu Val His Arg Tyr Arg Ala
 1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 43

Pro Tyr Ala Thr Asp Thr Arg
 1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 44

Met Val Asn Arg Ile Pro Thr
 1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 45

Pro Ser Ala Arg Asp Ser Gln
 1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 46

Leu Thr Asp Pro Gly His Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 47

Arg Ser Ser Arg Asn Ala Leu
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 48

Leu Thr Pro Thr Ala Thr Lys
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 49

Leu Ala Asn Gly Gly Asn Lys
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 50

Arg Val Ser Pro Asp Thr Leu
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 51

Ala Ile Arg Gly Arg Gly Glu
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 52

Leu Leu His Ser His Gly Lys
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 53

Val Asn His Gly Tyr Ser Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 54

Leu Ala Val Arg Asn Pro Ala
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 55

Ser Ala Ala Ser Gly Asn Ala
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 56

Trp Arg Phe Arg Asp Asp Pro
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 57

Leu Phe Asp Thr Asn Asn Leu
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 58

Pro Gly Asp Asn Asp Thr Leu

```
                    1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 59

Met Thr Ala Pro Asn Ile Gln
 1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 60

Leu Leu Ser Tyr Ser Gly Ala Arg
 1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 61

Arg Leu Ser Tyr Ala Leu Ala Arg
 1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 62

Arg Leu Ser Tyr Ser Leu Ala Arg
 1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 63

Arg Leu Ser Tyr Asn Leu Ala Arg
 1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 64

Ala Leu Ser Tyr Asn Phe Thr Arg
 1               5
```

```
<210> SEQ ID NO 65
<211> LENGTH: 8
<212> TYPE: PRT
<213> ORGANISM: Artificial Sequence
<220> FEATURE:
<223> OTHER INFORMATION: Synthetric Sequence

<400> SEQUENCE: 65

Arg Leu Tyr Thr Ser Asp Tyr Ser
 1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 66

Leu Leu Ser Tyr Asp Arg Val Arg
 1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 67

Leu Leu Ser Tyr Asp Arg Thr Arg
 1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 68

Arg Leu Tyr Thr Ala Ala Tyr His
 1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 69

Leu Leu Ser Tyr Asp Phe Thr Arg
 1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 70

Leu Leu Ala Tyr Pro Leu Thr Arg
 1               5
```

```
<210> SEQ ID NO 71
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 71

Leu Leu Ser Tyr Pro Phe Val Arg
 1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 72

Leu Leu Ser Pro Asp Asn His Arg
 1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 73

Ala Leu Ser His Asp Phe Ser Arg
 1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 74

Arg Leu Ser Tyr Pro Leu Ala Arg
 1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 75

Arg Leu Ser Tyr Glu Leu Ala Arg
 1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 76

Arg Leu Ser Tyr Asp Leu Ala Arg
 1               5
```

<210> SEQ ID NO 77
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 77
ctattctccc atggcacag                                                19

<210> SEQ ID NO 78
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 78
ttctgtatga ggttttgc                                                 18

<210> SEQ ID NO 79
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 79
acagggctta aggaggtgca gctggtgcag tctgg                              35

<210> SEQ ID NO 80
<211> LENGTH: 36
<212> TYPE: DNA
<213> ORGANISM: Artificial Sequence
<220> FEATURE:
<223> OTHER INFORMATION: Synthetic Sequence

<400> SEQUENCE: 80
tgttgttcta gaacctagga cggtgacctt ggtccc                             36

<210> SEQ ID NO 81
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 81
tctcacagtg cacaggcacc catggcagaa ggaggagggc                         40

<210> SEQ ID NO 82
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 82
tatttaaagc ggccgcccgc ctcggcttgt cacattttc t                        41

<210> SEQ ID NO 83
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 83
ctggaagatg tccaccagat actcgattgg atggcagta                          39

<210> SEQ ID NO 84
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 84
tactgccatc caatcgagta tctggtggac atcttccag                          39

<210> SEQ ID NO 85
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 85
attgcagcag cccccgcatt ccatcagggg cacacagga                          39

<210> SEQ ID NO 86
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 86
tcctgtgtgc ccctgatgga atgcgggggc tgctgcaat                          39

<210> SEQ ID NO 87
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 87
gatctcatca gggtactccg cgaagatgtc caccaggt                           39

<210> SEQ ID NO 88
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 88
accctggtgg acatcttcgc ggagtaccct gatgagatc                          39

<210> SEQ ID NO 89
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 89
ctcgatctca tcagggtacg cctggaagat gtccaccag                          39

<210> SEQ ID NO 90
<211> LENGTH: 38

```
<212> TYPE: DNA
<213> ORGANISM: Artificial Sequence
<220> FEATURE:
<223> OTHER INFORMATION: Synthetic Sequence

<400> SEQUENCE: 90
ctggtggaca tcttccaggc gtaccctgat gagatcga                              38

<210> SEQ ID NO 91
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 91
ctgcatggtg atgttggatt tctcagtggg cacacactc                             39

<210> SEQ ID NO 92
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 92
gagtgtgtgc ccactgagaa atccaacatc accatgcag                             39

<210> SEQ ID NO 93
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 93
catttgttgt gctgggtgaa gctcatctct cctatgtgct ggcct                      45

<210> SEQ ID NO 94
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 94
aggccagcac ataggagaga tgagcttcac ccagcacaac aaatg                      45

<210> SEQ ID NO 95
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 95
cagggtactc ctggaagatg tccaccagac gctcgattgg atggc                      45

<210> SEQ ID NO 96
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 96
```
gccatccaat cgagcgtctg gtggacatct tccaggagta ccctg         45

<210> SEQ ID NO 97
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 97
attgcagcag cccccgcacg ccatcagggg cacacagga               39

<210> SEQ ID NO 98
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 98
tcctgtgtgc ccctgatggc gtgcggggc tgctgcaat                39

<210> SEQ ID NO 99
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 99
ggtctgcatt cacaacggtg ttgctgtagg aagctcatct ctcct        45

<210> SEQ ID NO 100
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 100
aggagagatg agcttcctac agcacaaccg ttgtgaatgc agacc        45

<210> SEQ ID NO 101
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 101
ctcgtcattg cagcagcccg cgcatcgcat caggggcac               39

<210> SEQ ID NO 102
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 102
gtgcccctga tgcgatgcgc gggctgctgc aatgacgag               39

<210> SEQ ID NO 103
<211> LENGTH: 39
<212> TYPE: DNA
<213> ORGANISM: Artificial Sequence

```
<220> FEATURE:
<223> OTHER INFORMATION: Synthetic Sequence

<400> SEQUENCE: 103
tatcagcgca gctactgccg cccaatcgag accctggtg                              39

<210> SEQ ID NO 104
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 104
caccagggtc tcgattgggc ggcagtagct gcgctgata                              39

<210> SEQ ID NO 105
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 105
ctggagtgtg tgcccactag cgagtccaac atcaccatg                              39

<210> SEQ ID NO 106
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 106
catggtgatg ttggactcgc tagtgggcac acactccag                              39

<210> SEQ ID NO 107
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 107
cggatcaaac ctcaccaaag ccagcacata ggagagatg                              39

<210> SEQ ID NO 108
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 108
catctctcct atgtgctggc tttggtgagg tttgatccg                              39

<210> SEQ ID NO 109
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 109
atgagcttcc tacagcacag caaatgtgaa tgcagacca                              39
```

<210> SEQ ID NO 110
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 110
tggtctgcat tcacatttgc tgtgctgtag gaagctcat                              39

<210> SEQ ID NO 111
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 111
cagaatcatc acgaagtgat caagttcatg gatgtctat                              39

<210> SEQ ID NO 112
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 112
atagacatcc atgaacttga tcacttcgtg atgattctg                              39

<210> SEQ ID NO 113
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 113
ggctgctgca atgacgaggc actggagtgt gtgcccact                              39

<210> SEQ ID NO 114
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 114
agtgggcaca cactccagtg cctcgtcatt gcagcagcc                              39

<210> SEQ ID NO 115
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 115
ggcctggagt gtgtgcccgc agaggagtcc aacatcacc                              39

<210> SEQ ID NO 116
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 116
ggtgatgttg gactcctctg cgggcacaca ctccaggcc					39

<210> SEQ ID NO 117
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 117
gagtgtgtgc ccactgaggc atccaacatc accatgcag					39

<210> SEQ ID NO 118
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 118
ctgcatggtg atgttggatg cctcagtggg cacacactc					39

<210> SEQ ID NO 119
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 119
ctacagcaca acaaatgtgc atgcagacca aagaaagat					39

<210> SEQ ID NO 120
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 120
atctttcttt ggtctgcatg cacatttgtt gtgctgtag					39

<210> SEQ ID NO 121
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 121
cacaacaaat gtgaatgcgc accaaagaaa gatagagca					39

<210> SEQ ID NO 122
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 122
tgctctatct ttctttggtg cgcattcaca tttgttgtg					39

<210> SEQ ID NO 123

```
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 123
gatgtctatc agcgcagcgc atgccatcca atcgagacc                              39

<210> SEQ ID NO 124
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 124
ggtctcgatt ggatggcatg cgctgcgctg atagacatc                              39

<210> SEQ ID NO 125
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 125
aagttcatgg atgtctatgc acgcagctac tgccatcca                              39

<210> SEQ ID NO 126
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 126
tggatggcag tagctgcgtg catagacatc catgaactt                              39
```